(12) United States Patent
Burk et al.

(10) Patent No.: US 11,319,320 B2
(45) Date of Patent: May 3, 2022

(54) PIM KINASE INHIBITOR COMPOSITIONS, METHODS, AND USES THEREOF

(71) Applicant: Snap Bio, Inc., San Diego, CA (US)

(72) Inventors: Mark J. Burk, San Diego, CA (US); Brandon Chen, San Diego, CA (US); Jingyi Li, San Diego, CA (US); Shawn Bachan, San Diego, CA (US)

(73) Assignee: SNAP BIO, INC., San Diego, CA (US)

( * ) Notice: Subject to any disclaimer, the term of this patent is extended or adjusted under 35 U.S.C. 154(b) by 0 days.

(21) Appl. No.: 16/761,715

(22) PCT Filed: Nov. 5, 2018

(86) PCT No.: PCT/US2018/059160
§ 371 (c)(1),
(2) Date: May 5, 2020

(87) PCT Pub. No.: WO2019/090205
PCT Pub. Date: May 9, 2019

(65) Prior Publication Data
US 2020/0331914 A1    Oct. 22, 2020

Related U.S. Application Data

(60) Provisional application No. 62/581,917, filed on Nov. 6, 2017.

(51) Int. Cl.
*C07D 471/22* (2006.01)
*C07D 487/14* (2006.01)
*C07D 487/22* (2006.01)

(52) U.S. Cl.
CPC ......... *C07D 471/22* (2013.01); *C07D 487/14* (2013.01); *C07D 487/22* (2013.01)

(58) Field of Classification Search
CPC .................................................. C07D 471/22
USPC ...................................................... 514/232.8
See application file for complete search history.

(56) References Cited

U.S. PATENT DOCUMENTS

| | | | |
|---|---|---|---|
| 5,438,050 A | | 8/1995 | Kleinschroth et al. |
| 5,629,304 A | | 5/1997 | Murakata et al. |
| 5,883,114 A | * | 3/1999 | Kleinschroth ....... C07D 487/14 514/410 |
| 5,945,440 A | | 8/1999 | Kleinschroth et al. |
| 2004/0152721 A1 | | 8/2004 | Prudhomme et al. |

FOREIGN PATENT DOCUMENTS

| | | |
|---|---|---|
| CN | 106146475 A | 11/2016 |
| DE | 4217963 A1 * | 12/1993 |
| WO | 9402488 | 2/1994 |
| WO | 9807433 A1 | 2/1998 |
| WO | 2017031399 A1 | 2/2017 |
| WO | 2019/000224 A1 * | 11/2019 |
| WO | 2020223306 A1 | 11/2020 |

OTHER PUBLICATIONS

Wang et al., Chem. & Biodiversity (2017) vol. 14(3), published online Oct. 1, 2016.*
Slater et al., Bioorg. & Med. Chem. Letters (2001), vol. 11(15), pp. 1993-1995.*
Ashton et al., J. Chromatography. B: Biomed. Sci. & Applications. (1996), vol. 677(1), pp. 194-198.*
International Search Report for International Application No. PCT/US2018/059160, dated Mar. 7, 2019, 16 pages.
Written Opinion for International Application No. PCT/US2018/059160, dated Mar. 7, 2019, 13 pages.
Anizon (2010) "Fighting Tumor Cell Survival: Advances in the Design and Evaluation of Pim Inhibitors", Current Medicinal Chemistry, 17(34):4114-4133.
Guoxin Zhu et al. (2003) "Synthesis, structure-activity relationship, and biological studies of indolocarbazoles as potent cyclin DI-CDK4 inhibitors", Journal of Medicinal Chemistry, American Chemical Society, 46(11):2027-2030.
Potharaju Raju et al. (2015) "Synthetic Studies on Indolocarbazoles: A Facile Synthesis of Staurosporinone Analogues : Facile Synthesis of Staurosporinone Analogues", European Journal of Organic Chemistry, 2015(32):7131-7145.
Slater et al. (1991) "Indolocarbazoles: Potent, Selective Inhibitors of Human Cytomegalovirus Replication", Bioorganic & Medicinal Chemistry, Pergamon, GB, 7(6):1067-1074.
Sungjong Lee et al. (2017) "Total Syntheses of Arcyriaflavin A and Calothrixin B Using 2,2'-Bisindole-3-acetic Acid Derivative as a Common Intermediate", Organic Letters, 19(11):2785-2788.
Onaka et al. (2003) "Characterization of the Biosynthetic Gene Cluster of Rebeccamycinfrom Lechevalieria Aerocolonigenes ATCC 39243", Biosci. Biotech. Biochem., 67(1):127-138.
Slater et al. (2001) "Synthesis of N-Alkyl Substituted Indolocarbazoles as Potent Inhibitors of Human Cytomegalovirus Replication", Bioorganic & Medicinal Chemistry Letters, 11(15):1993-1995.
Shotaro Hoshino et al. (2014) "Arcyriaflavin E, a new cytotoxic indolocarbazole alkaloid isolated by combined-culture of mycolic acid-containing bacteria and *Streptomyces cinnamoneus* NBRC 13823", The Journal of Antibiotics, 68(5):342-344.
Sanchez-Martinez et al., (2003) "Aryl [a]pyrrolo[3,4-c]carbazoles as selective cyclin DI-CDK4 inhibitors", Bioorganic & Medicinal Chemistry Letters, Pergamon, Amsterdam, NL, 13(21):3835-3839.
Lefoix et al. (2008) "Novel 5-azaindolocarbazoles as cytotoxic agents and Chkl inhibitors", Bioorganic & Medicinal Chemistry, Pergamon, GB,16(9):5303-5321.

(Continued)

*Primary Examiner* — Taofiq A Solola
(74) *Attorney, Agent, or Firm* — Kagan Binder, PLLC

(57) ABSTRACT

This application relates to compounds of formulae (I) and (II) and compositions thereof useful as inhibitors of PIM kinases. Also provided are methods of synthesis and methods of use of PIM inhibitors in treating individuals suffering from cancerous malignancies.

14 Claims, 22 Drawing Sheets

Specification includes a Sequence Listing.

(56) References Cited

OTHER PUBLICATIONS

Sanchez et a. (2005) "Combinatorialbiosynthesis of antitumor indolocarbazole compounds", Proceedings of the National Academy of Sciences of the United States of America, National Academy of Sciences, 102(2):461-466.

Balu et al. (2004) "Design and Synthesis of a Fluoroindolocarbazole Series as Selective Topoisomerase I Active Agents. Discovery of Water-Soluble 3,9-Difluoro-12,13-dihydro-13-[6-amino-.be ta.-D-glucopyranosyl]-5H,I 3H-benzo [b]-thienyl[2,3-a]pyrrolo[3,4-c]carbazole-5,7 (6H)-dione (BMS-251873) with Curative Antitumor Act", Journal of Medicinal Chemistry, American Chemical Society, 47(7):1609-1612.

Bullock et al. (2005) "Structural basis of inhibitor specificity of the human protooncogene proviral insertion site in Moloney Murine Leukemia Virus (PIM-1) Kinase", Journal of Medicinal Chemistry, American Chemical Society, 48(24):7604-7614.

Drygin et al. (2012) "Potential Use of Selective and Nonselective Pim Kinase Inhibitors for Cancer Therapy: Mini perspective", Journal of Medicinal Chemistry, 55(19):8199-8208.

\* cited by examiner

PIM KINASE INHIBITOR COMPOSITIONS, METHODS, AND USES THEREOF

CROSS-REFERENCE TO RELATED APPLICATION

This application claims priority to International Patent Application No. PCT/US2018/059160, filed Nov. 5, 2018, which claims the benefit of priority of U.S. provisional application No. 62/581,917, filed on Nov. 6, 2017, the entire contents of which are incorporated herein by reference in their entirety.

REFERENCE TO THE SEQUENCE LISTING

The entire contents of the ASCII text file entitled "SNA0003WO_Sequence_Listing.txt," created on Oct. 31, 2018 and having a size of 33 kilobytes is incorporated herein by reference in its entirety.

BACKGROUND

The search for new therapeutic agents has been greatly aided in recent years by a better understanding of the structure of enzymes and other biomolecules associated with diseases. One important class of enzymes that has been the subject of extensive study over the past twenty years is protein kinases.

Protein kinases constitute a large family of structurally related enzymes that are responsible for catalyzing the phosphorylation of specific amino acid residues in proteins and thereby controlling a variety of signal transduction processes within the cell in response to external stimuli (Ubersax, J. A., Ferrell, J. E., Nat. Rev. Mol. Cell Biol., 2007, 8, 530-541; Shchemelinin, I. et al., Folia Biol., 2006, 52, 81-101). Protein kinases are thought to have evolved from a common ancestral gene due to the conservation of their structure and catalytic function (Manning, G., et al., Science, 2002, 298, 1912-1934). There are at least 518 kinases in the human body and almost all kinases contain a similarly structured ATP-binding pocket and catalytic domain containing 250-400 amino acids. Kinases are categorized into families according to the substrates they phosphorylate (e.g., the hydroxyl group of protein-tyrosine residues, protein-serine/threonine residues, or lipids).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above (Roskoski, R. Jr., Pharmacol. Res., 2015, 100, 1-23; Fleuren, E. D. G., et al., Nat. Rev. Cancer, 2016, 16, 83-98). These diseases include, but are not limited to, cancer, autoimmune diseases, inflammatory diseases, bone diseases, metabolic diseases, neurological and neurodegenerative diseases, cacardiovascular diseases, allergies and asthma, Alzheimer's disease, and hormone-related diseases. Accordingly, there remains a need to find new safe and efficacious protein kinase inhibitors that are useful as therapeutic agents.

Cancer is a disease that derives from cells and tissues that overcome inherent cell growth checkpoints and regulators, thus leading to transformation into a malignant state of uncontrolled proliferation. As indicated above, kinases play a central role in regulating and transducing signals from the cell surface to the nucleus in order to elicit a response to extracellular stimuli. Aberrant kinase-mediated signaling, such as that propogated by overactive or abnormally abundant kinases, is often associated with cell growth, proliferation, migration, and survival, which are known to be key drivers of cancer pathology. Many types of cancer are known, and include the following:

Endodermal cancers are serious malignancies of tissues that derive from inner embryonic endoderm layer, which includes the stomach, liver, colon, gallbladder, prostate, and pancreas. Several of these cancers typically have a poor prognosis when advanced beyond Stage II upon diagnosis. For example, it is estimated that 41,000 adults in the United States will be diagnosed with primary liver cancer and 29,000 deaths will occur from this disease in 2017. The incidence of liver cancer has tripled since 1980 and it is now the 5th most common cause of cancer death among men and the general 5-year survival rate is only 18%. Similarly, 28,000 adults in the United States will be diagnosed with stomach cancer and 10,960 deaths (6,720 men and 4,240 women) will occur from this disease will occur in 2017. The general 5-year survival rate for people with stomach cancer is 30%. Also, an estimated 53,000 adults in the United States will be diagnosed with pancreatic cancer and 41,780 deaths will occur from this disease in 2017. Pancreatic ductal adenocarcinoma makes up the vast majority (90%) of all pancreatic malignancies and remains a disease with very poor prognosis and high morbidity. Pancreatic cancer is the fourth leading cause of cancer death in the US and prognosis is poor because pancreatic cancer is difficult to diagnose, with an estimated 1-year survival rate of 29%, and a 5-year survival rate of just 7%. Survival rates decrease further if the cancer is not diagnosed early and there is an important need for new therapeutics that enable more effective treatment of endodermal cancers at all stages (For endodermal cancer statistics, see the websites: www.cancer.net and www.cancer.org).

The PIM (proviral integration site for Moloney murine leukemia virus) kinases are a family of three constitutively active proto-oncogenic serine/threonine kinases, PIM1, PIM2, and PIM3, which have been shown to regulate signaling associated with several important normal biological processes, including cell survival, proliferation, differentiation, and apoptosis. However, when these processes become disrupted or hyperactivated, they manifest the hallmarks of cancer. The PIM kinases promote cell survival and downregulate cell apoptosis and, accordingly, have been shown to be involved directly in signaling mechanisms associated with tumorigenesis. Importantly, PIM1 and PIM3 kinases have been found to be widely and aberrantly expressed, particularly in endodermal cancers of the human colon, stomach, liver, prostate, and pancreas. Inhibition of PIM 1 and/or PIM3, for example with targeted short hairpin shRNA, was shown to significantly increase levels of apoptosis and reduce proliferation of endodermal cancer cell lines and of endodermal tumors in mice (See: Li Y Y., et al., Cancer Res., 2006, 66(13), 6741-6747; Zheng H C, et al., J. Cancer Res. Clin. Oncol., 2008, 134(4), 481-488; Fujii C, et al., Int. J. Cancer, 2005, 114(2), 209-218; Popivanova B. K., et al., Cancer Sci., 2007, 98(3), 321-328; Qu, Y., et al., Med. Sci. Monit., 2016, 22, 4254-4260; Xu, J., et al., J. Exp. Clin. Can. Res., 2016, 35 (133), 1-12, DOI 10.1186/s13046-016-0406-z.). In addition, PIM1 and/or PIM3 overexpression has been shown to be involved in other malignancies, such as cancer of the ovaries (Zhuang, H., et al., Asian Pac. J. Cancer Prev., 2015, 16(8), 3325-3331) and in glioblastomas (Quan, J., et al., Cell. Mol. Biol., 2015, 61(1), 42-50).

Due to the aforementioned poor prognosis and limited therapeutic options associated with endodermal and other cancers that overexpress PIM1 and/or PIM3, development of selective inhibitors of PIM1 and/or PIM3 kinase represents a novel strategy for specifically treating cancers, especially those of the stomach, liver, colon, prostate, esophagus, pancreas, and other endodermal organs, with drugs, either alone or in combination with other therapeutic agents, that exhibit higher efficacy, lower toxicity, and lower susceptibility to resistance relative to existing treatment modalities.

SUMMARY

This disclosure provides potent and selective inhibitors of the family of three protein kinases referred to as PIM (Proviral Integration site of Moloney murine leukemia virus), PIM inhibitor compositions of general Formulas (I)-(II) set out below, pharmaceutical formulations, methods for their preparation, and uses thereof, including uses aimed at specifically targeting endodermal cancers through selective inhibition of PIM3.

Described herein are compounds, compositions, and methods for treating an individual suffering with cancers of the endodermal organs, including the cecum, intestine, stomach, thymus, liver, pancreas, lungs, esophagus, gallbladder, thyroid, lungs, and prostate, and which are manifested in a variety of forms, such as by way of example, esophageal adenocarcinoma, squamous cell carcinoma, nasopharyngeal carcinoma, gastric adenocarcinoma, pancreatic ductal adenocarcinoma, hepatocellular carcinoma, gallbladder adenocarcinoma, prostatic adenocarcinoma, colorectal adenocarcinoma, gastrointestinal stromal tumors (GIST), and gastrointestinal carcinoid tumors or the like, by administering to an individual a pharmaceutical composition comprising a therapeutically effective amount of an inhibitor of the PIM kinases, as described herein. Compounds of the invention can inhibit PIM reversibly by competitively binding potently and selectively to the ATP-binding pocket of the kinase. Certain compounds of the inventions can be used to selectively inhibit PIM3, and to a lesser degree PIM1 and PIM2, and specifically target cancers that overexpress the PIM3 kinase as a means of survival, growth, and proliferation leading to cancer pathology and disease progression. Other compounds of the invention inhibit PIM1 and PIM3, and to a lesser degree PIM2, and therefore are useful for diseases that overexpress these kinases. Yet other compounds of the invention target all three PIM kinases (PIM1-3) with approximately the same degree of potency and are useful for treating diseases where all three PIM kinases are involved in disease.

During the course of our research, we unexpectedly discovered during a broad kinase screening initiative that the natural products acryriaflavin A and K252a (See: Nakano, H. and Omura, S., J. Antibiot., 2009, 62, 17-26) have high affinity for the kinase PIM3. For example, when the affinity of arcyriaflavin A was analyzed against 450 kinases using the kinase screening platform KINOMEscan® (DiscoverX, Inc., San Diego, Calif.), we discovered that this molecule bound tightly to PIM3 with a $K_d$ of 2 nM and had an order of magnitude lower affinity for both PIM1 ($K_d$=21 nM) and PIM2 ($K_d$=19 nM). Relative to arcyriaflavin A, K252a was shown to have a slightly reduced binding affinity for PIM3 ($K_d$ ca. 10 nM), and even lower for PIM1 and PIM2. Biochemical assays performed in the presence of ATP (Reaction Biology Corporation, Malvern, Pa.) confirmed potent inhibition of PIM3 by arcyriaflavin A with $IC_{50}$=0.13 nM.

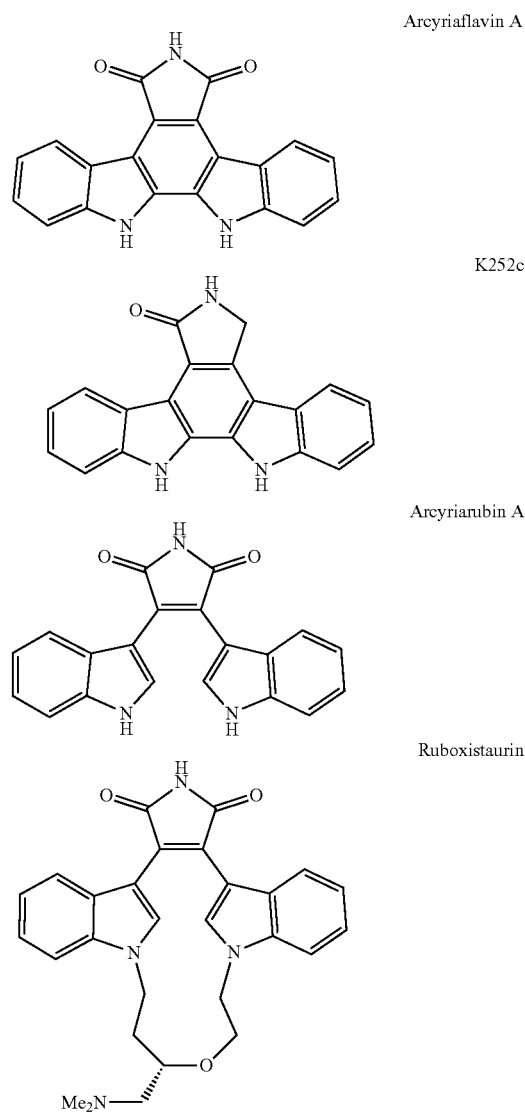

Similarly, a broad screen of kinases against a panel of known kinase inhibitors unexpectedly revealed that ruboxistaurin (See: Jirousek, M. R., et al., J. Med. Chem., 1996, 39, 2664-2671), a drug that was clinically developed as a potent PKC inhibitor for diabetic retinopathy and neuropathy, was also a potent and selective inhibitor of PIM3 (See: Karaman, M. W., et al., Nat. Biotechnol., 2008, 26, 127-132; Davis, M. I., et al., Nat. Biotech., 2011, 11, 1046-1051). Ruboxistaurin (LY333531) is a dialkylated macrocyclic analog of the known natural product arcyriarubin A. These results suggested that further optimization of these lead molecules would enable the development of potent and selective inhibitors of PIM3 as novel treatments for patients afflicted with serious endodermal cancers.

In one aspect of this invention is a compound having the structure of Formula (I) or a pharmaceutically acceptable salt, solvate, hydrate, N-oxide, prodrug, stereoisomer, enantiomer, mixture of enantiomers, mixture of diastereomers, isotopic variants, and metabolites thereof; wherein Formula (I) is as defined in the Detailed Description below.

In another embodiment of the invention are compounds having the structure of Formula (II) or a pharmaceutically acceptable salt, solvate, hydrate, N-oxide, prodrug, stereoisomer, enantiomer, mixture of enantiomers, mixture of diastereomers, isotopic variants, and metabolites thereof, which are examples representing kinase inhibitors, wherein Formula (II) is as defined in the Detailed Description below.

Also provided herein are pharmaceutical compositions comprising a compound disclosed herein, e.g., a compound of Formulas (I) and (II), including a stereoisomer, enantiomer, mixture of enantiomers, mixture of diastereomers, or isotopic variant thereof; or a pharmaceutically acceptable salt, solvate, hydrate, or prodrug thereof; and one or more pharmaceutically acceptable excipients.

Further provided herein is a method of treating, preventing, or ameliorating one or more symptoms of a disorder, disease, or condition involving PIM3 expression in a subject, comprising administering to the subject a therapeutically effective amount of a compound disclosed herein, e.g., a compound of Formulas (I) or (II), including a stereoisomer, enantiomer, mixture of enantiomers, mixture of diastereomers, or isotopic variant thereof; or a pharmaceutically acceptable salt, solvate, hydrate, or prodrug thereof.

Also provided herein is a method of treating, preventing, or ameliorating one or more symptoms of a disorder, disease, or condition in a subject, including cancers of endodermal organs such as the stomach, liver, colon, pancreas, prostate, and gallbladder, as well as other cancers involving PIM3 expression, comprising administering to the subject a therapeutically effective amount of a compound disclosed herein, e.g., a compound of Formulas (I) or (II), including a stereoisomer, enantiomer, mixture of enantiomers, mixture of diastereomers, or isotopic variant thereof; or a pharmaceutically acceptable salt, solvate, hydrate, or prodrug thereof.

Additionally provided herein is a method of modulating PIM3 kinase activity, comprising contacting a PIM3 kinase in vitro or in vivo with a therapeutically effective amount of a compound disclosed herein, e.g., a compound of Formulas (I) or (II), including a stereoisomer, enantiomer, mixture of enantiomers, mixture of diastereomers, or isotopic variant thereof; or a pharmaceutically acceptable salt, solvate, hydrate, or prodrug thereof.

Also provided herein is a method of treating, preventing, or ameliorating one or more symptoms of a PIM3 kinase-mediated disorder, disease, or condition in a subject, comprising administering to the subject a therapeutically effective amount of a compound disclosed herein, e.g., a compound of Formulas (I) or (II), including a stereoisomer enantiomer, mixture of enantiomers, mixture of diastereomers, or isotopic variant thereof; or a pharmaceutically acceptable salt, solvate, hydrate, or prodrug thereof, wherein the compound partially or completely inhibits PIM3 activity and displays increased potency against PIM3 kinase and/or increased selectivity for inhibiting PIM3 kinase relative to PIM1 kinase, PIM2 kinases and other kinases known to be present in the human body.

DETAILED DESCRIPTION

Figure 1A:
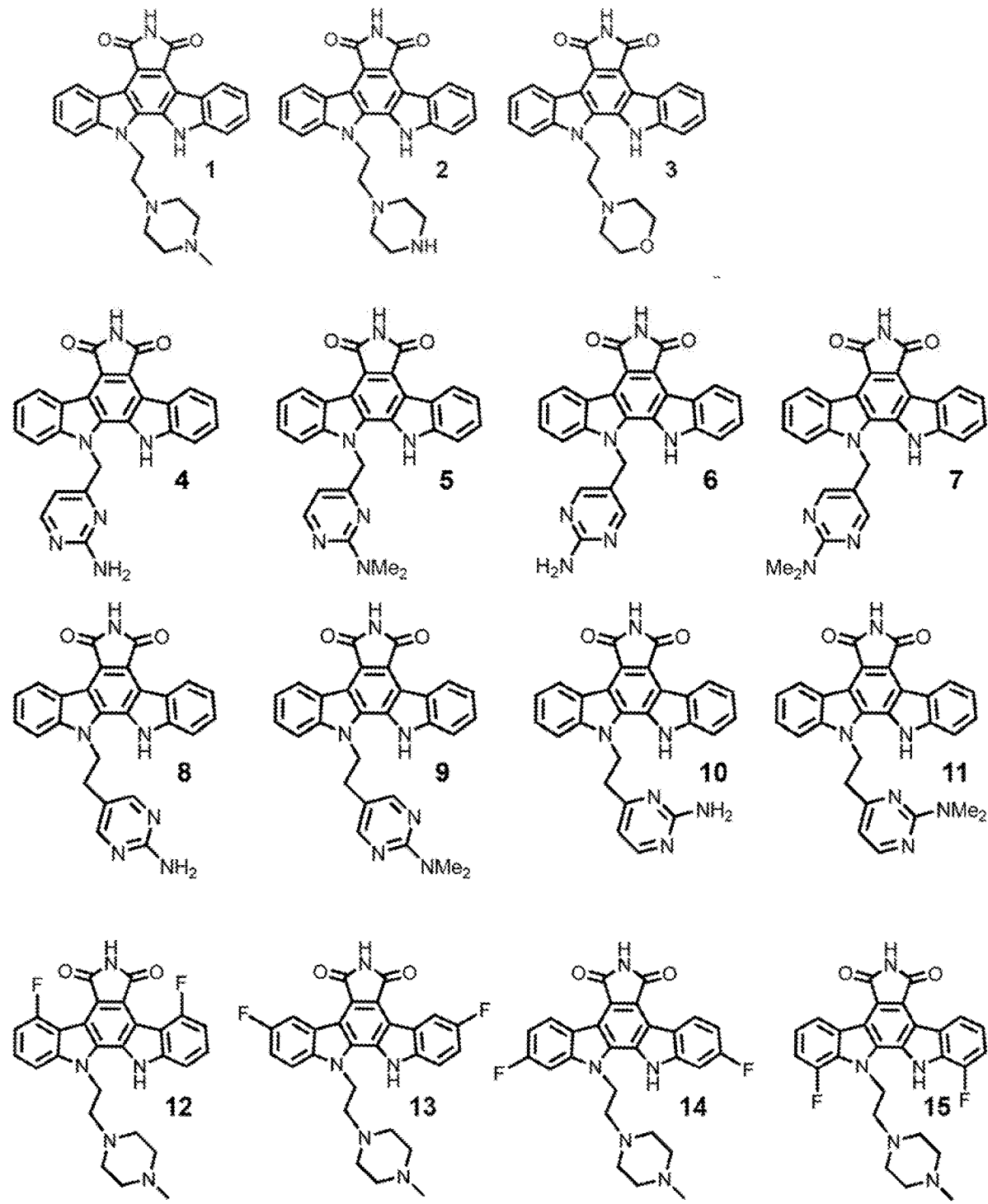
FIGS. 1A-1S represents embodiments of the various 1-307 compounds.
Figure 1B:
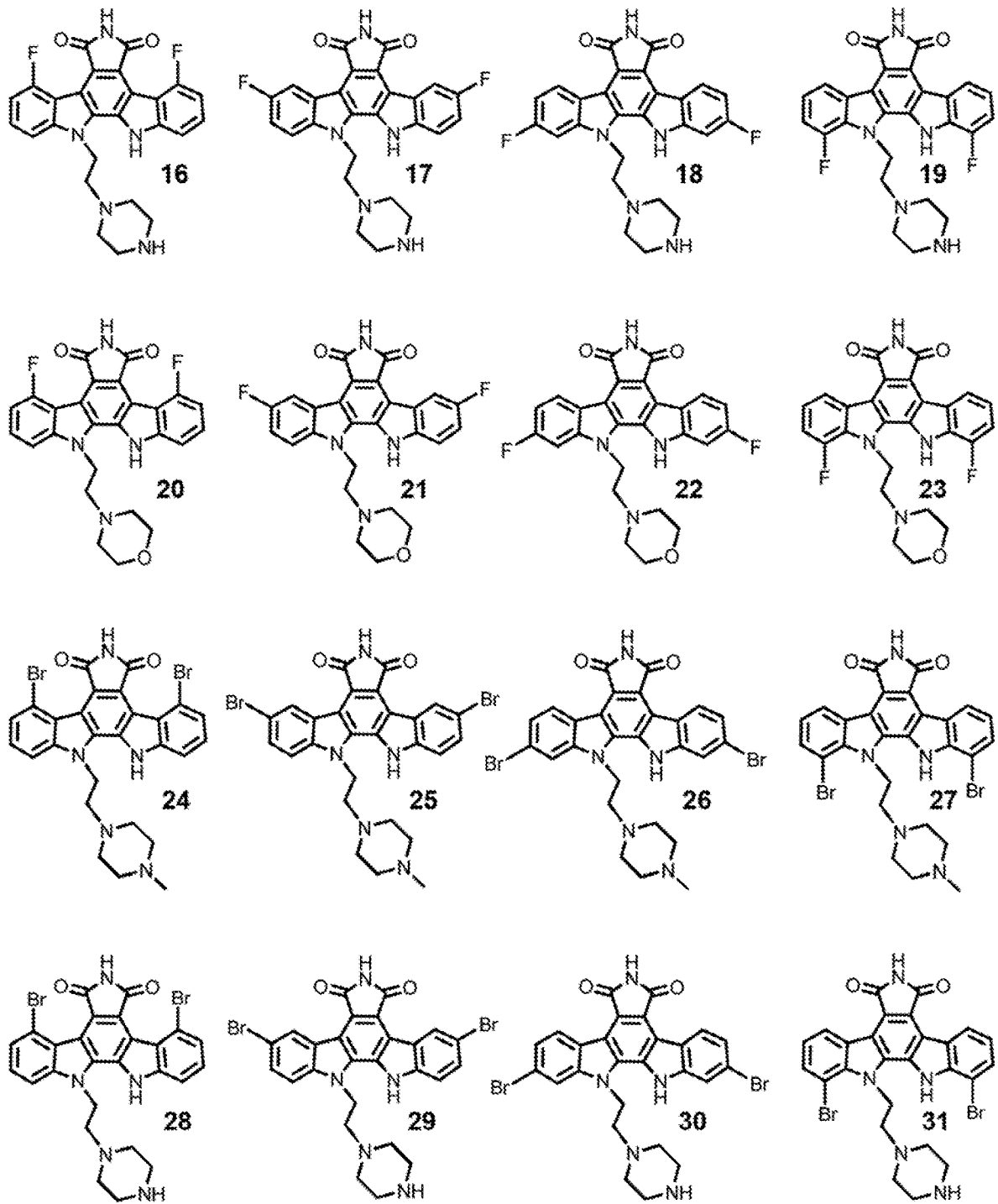
Figure 1C:
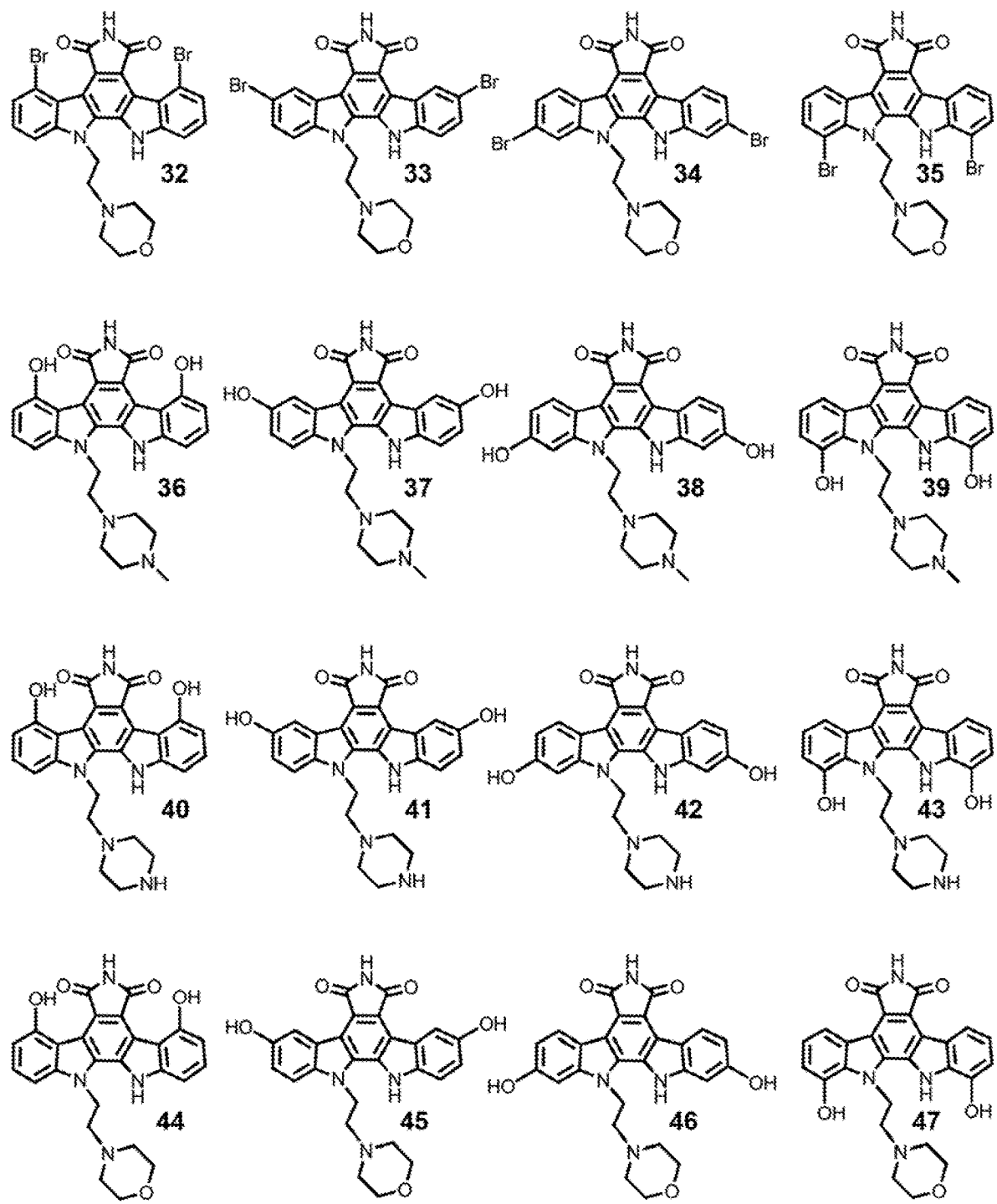
Figure 1D:
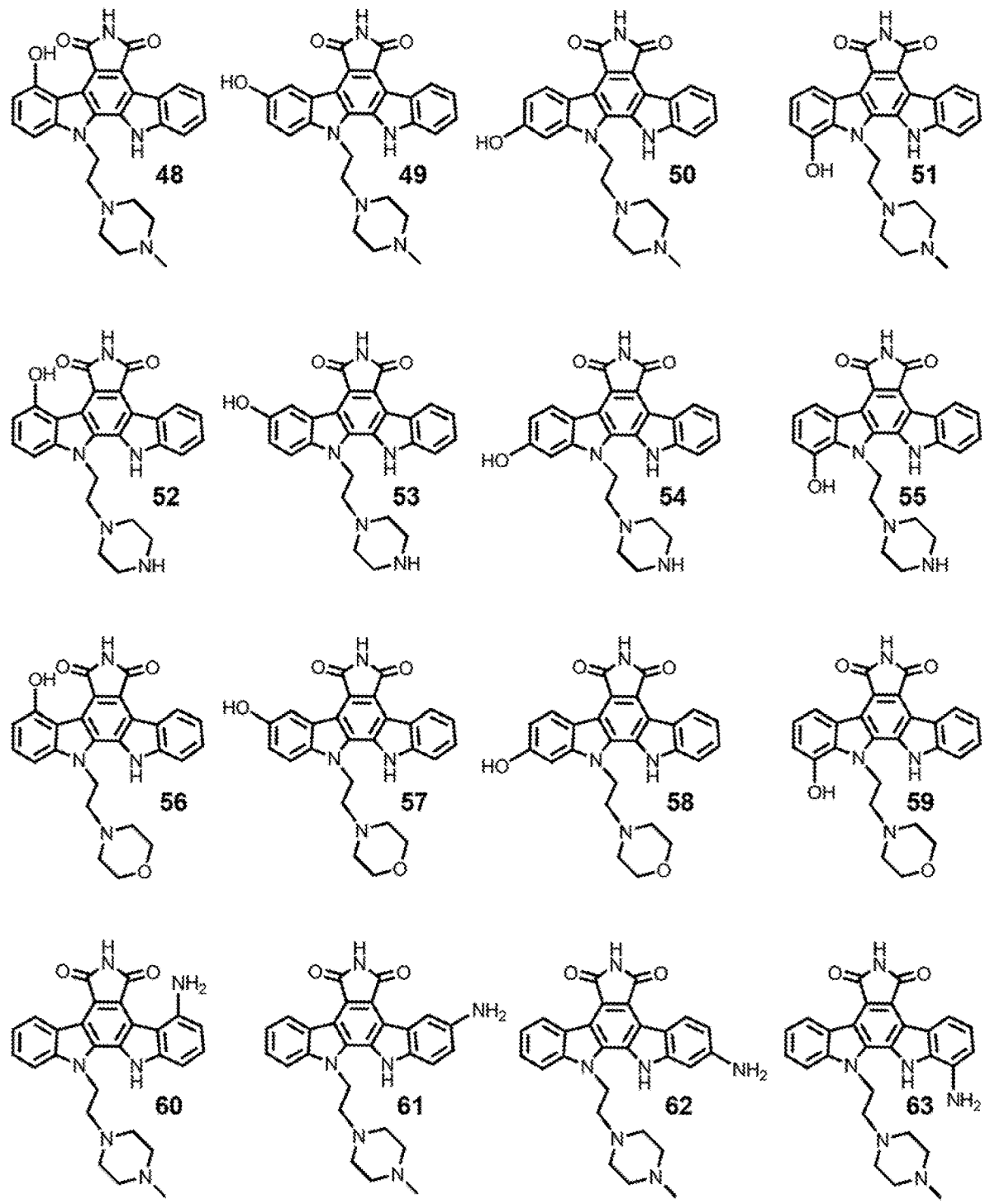
Figure 1E:
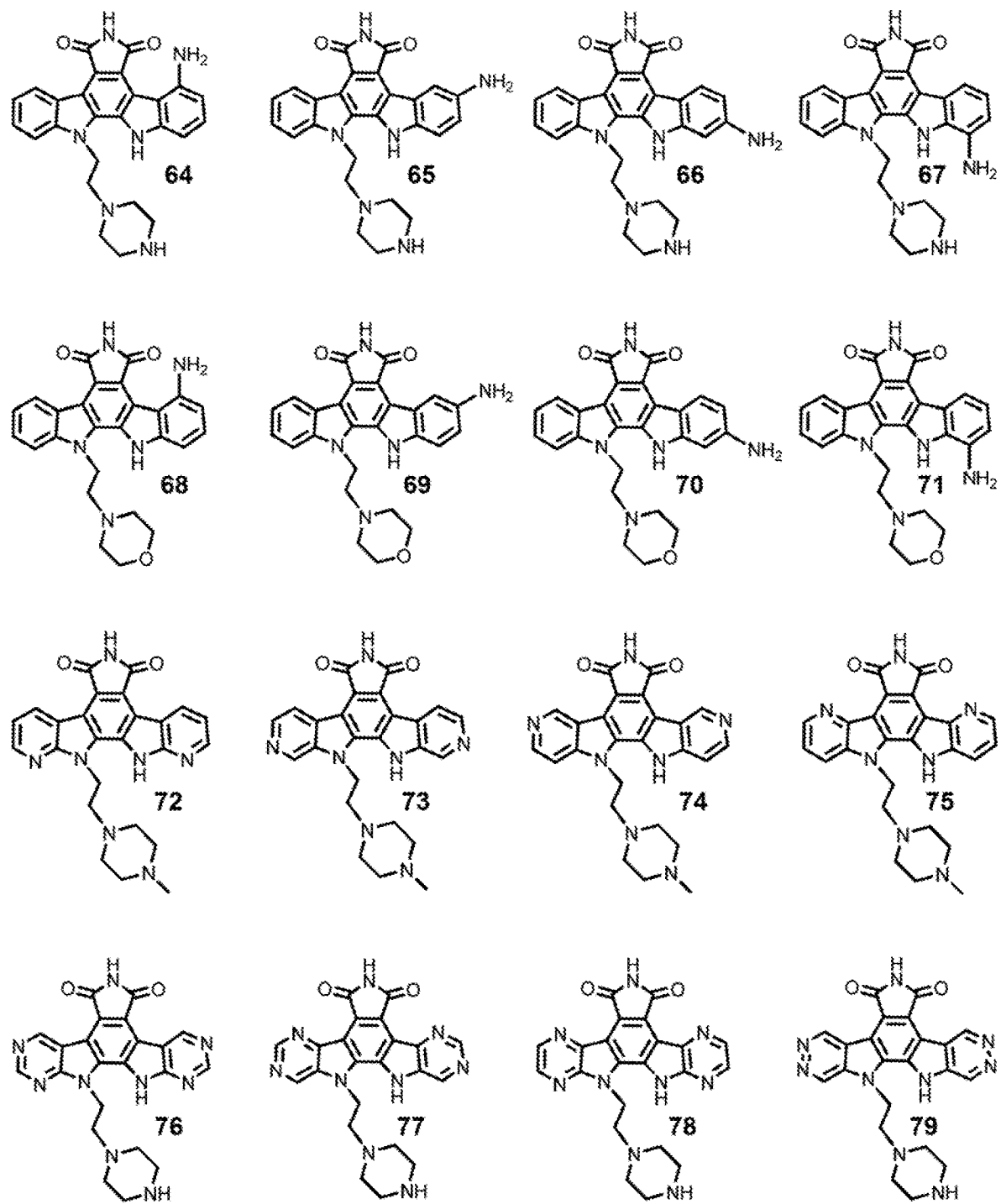
Figure 1F:
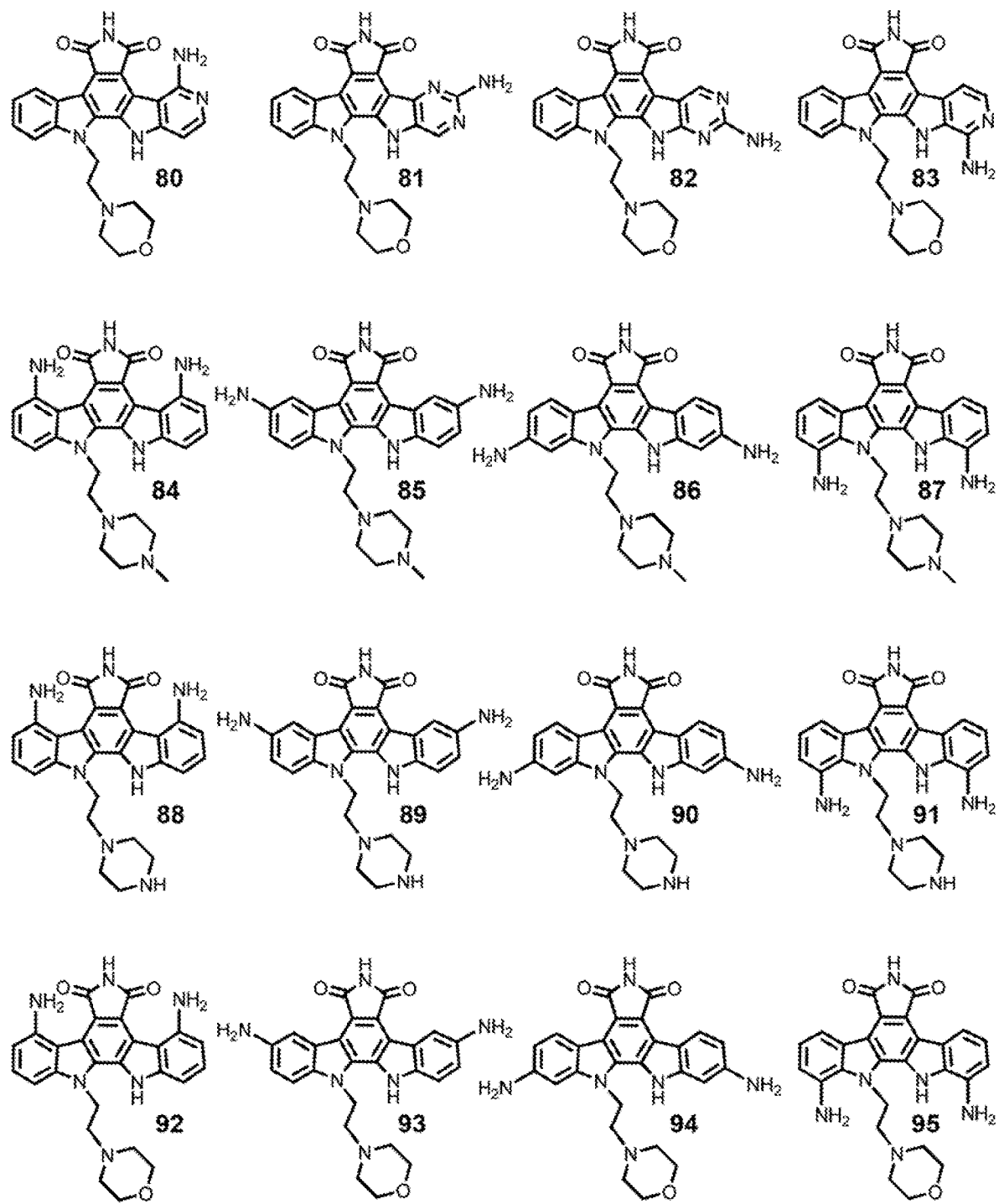
Figure 1G:
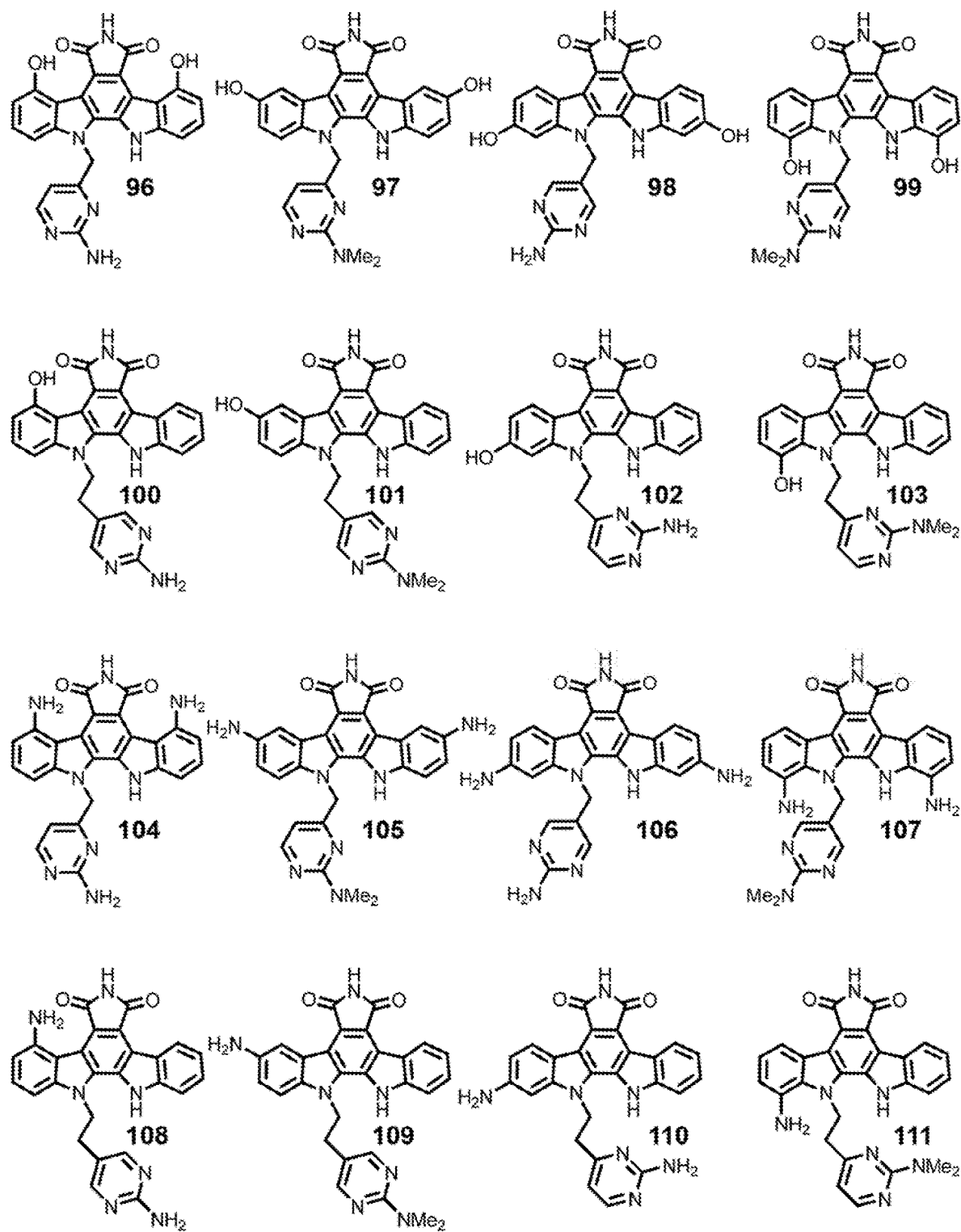
Figure 1H:
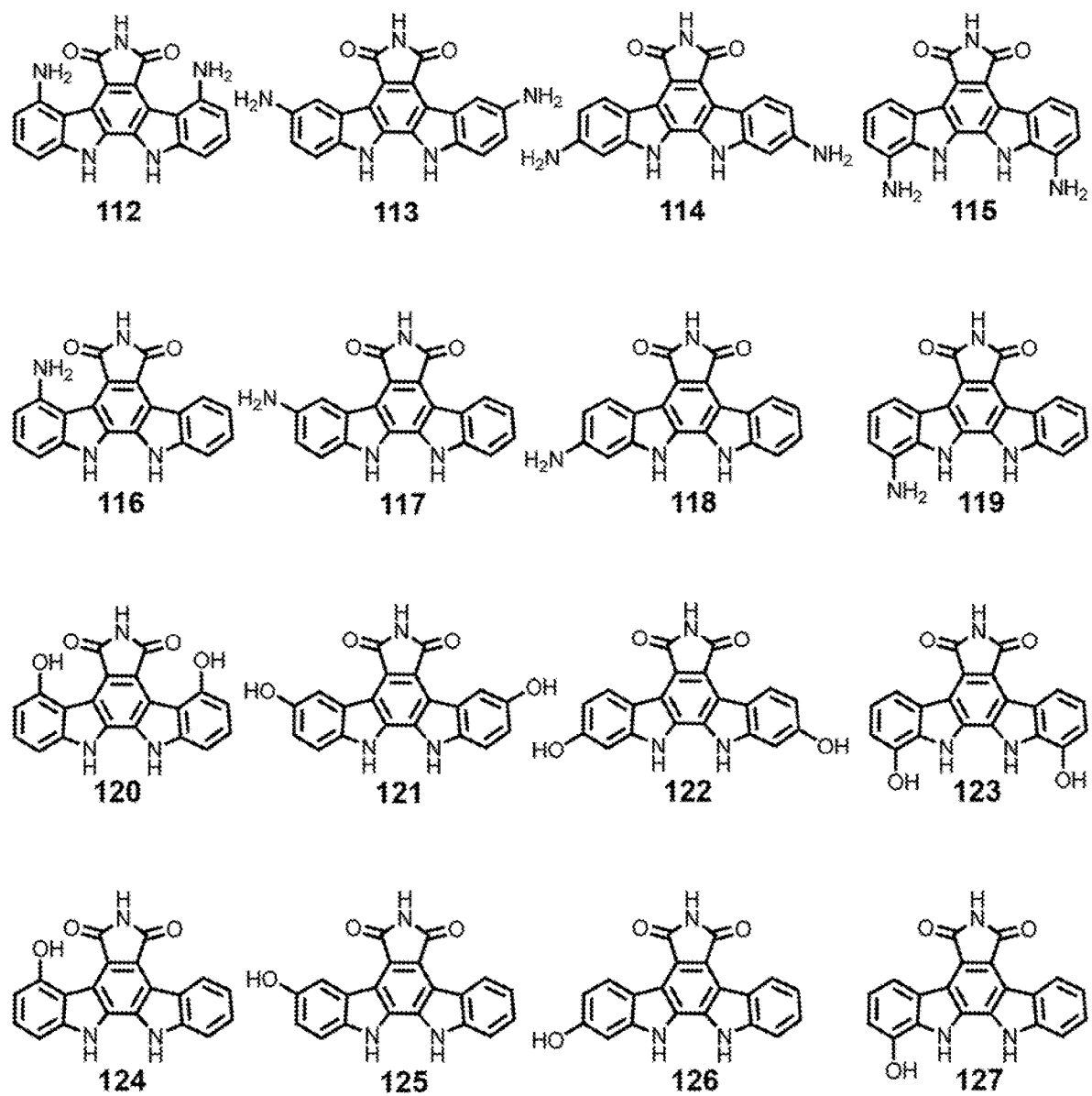
Figure 1I:
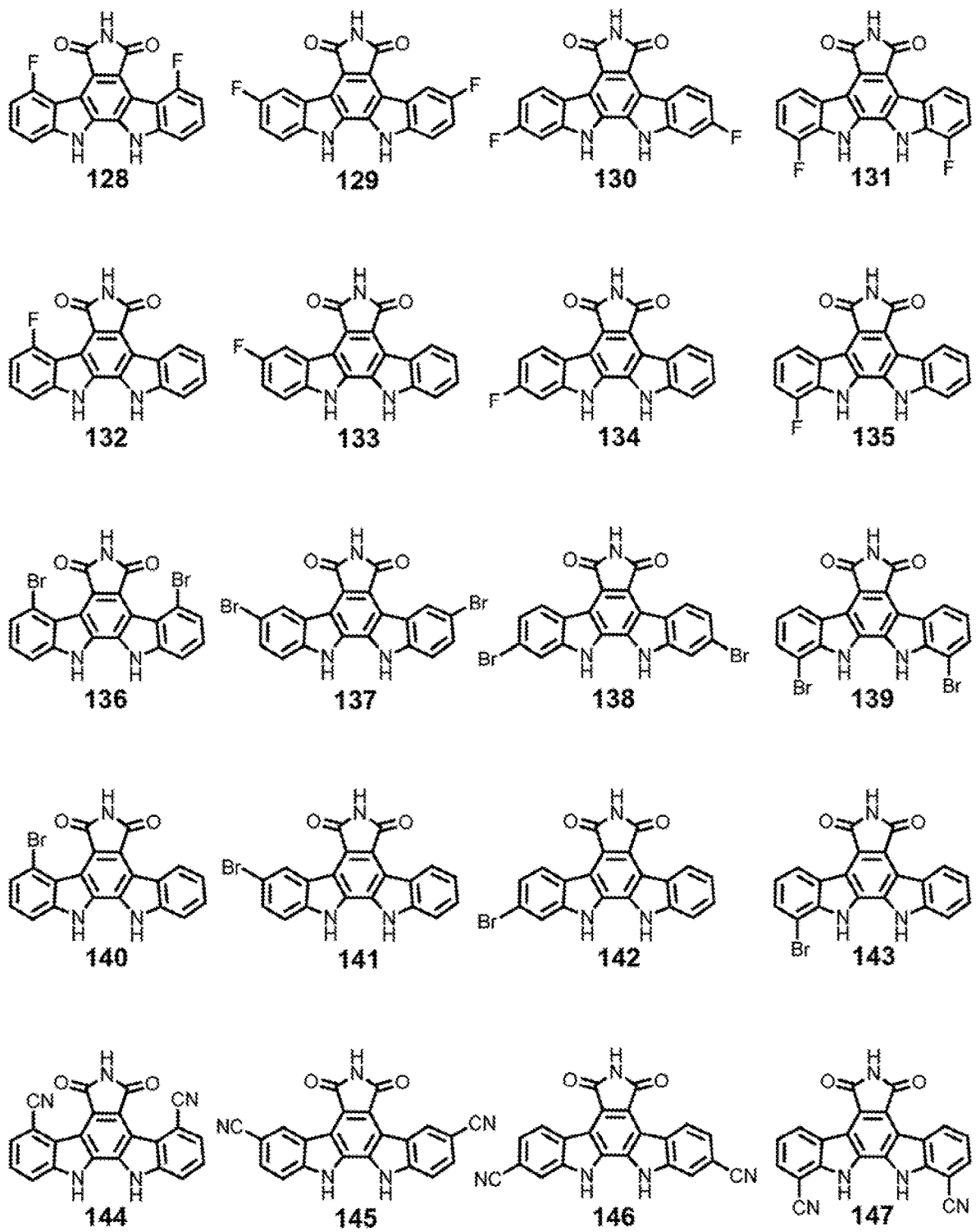
Figure 1J:
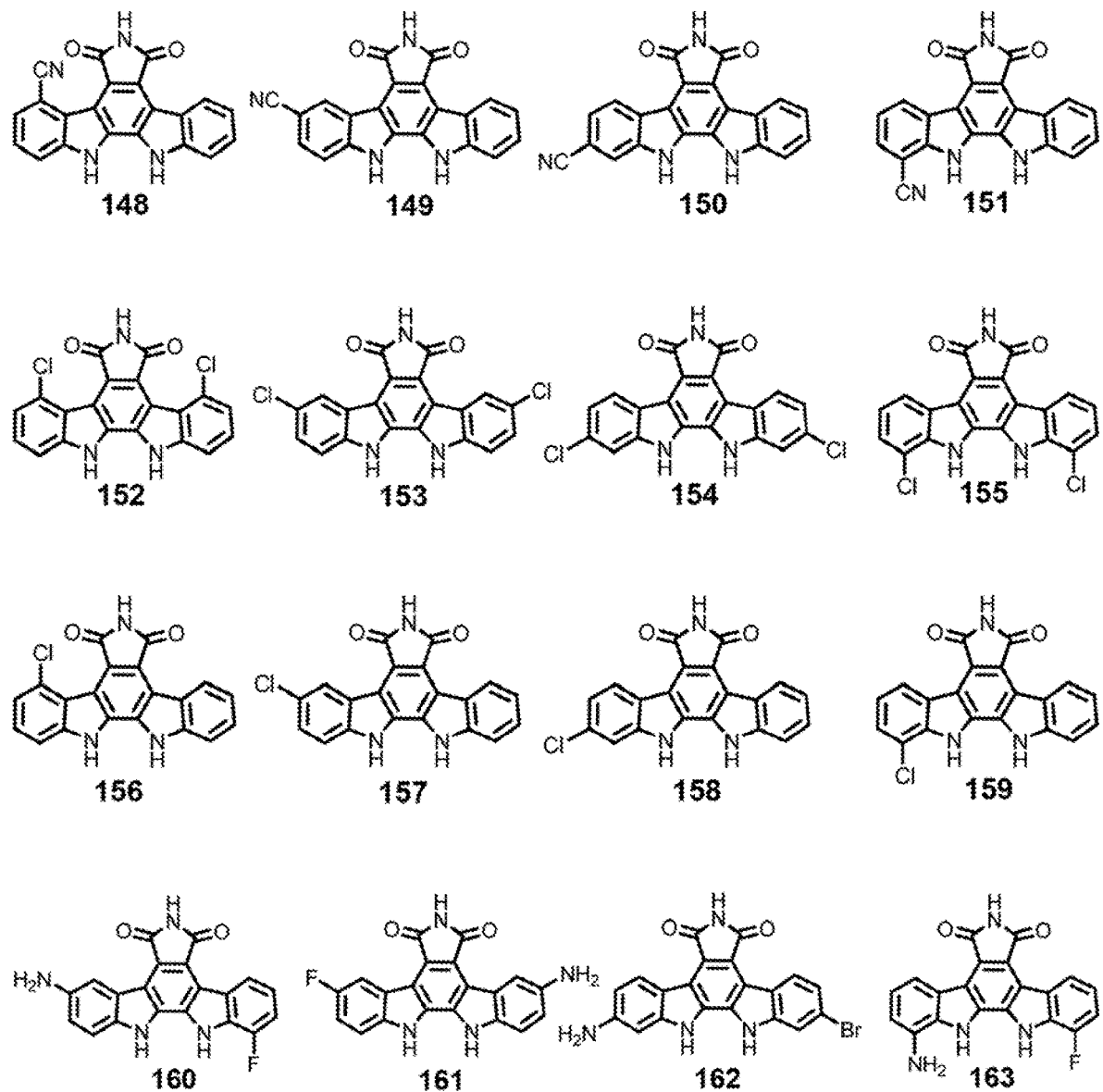
Figure 1K:
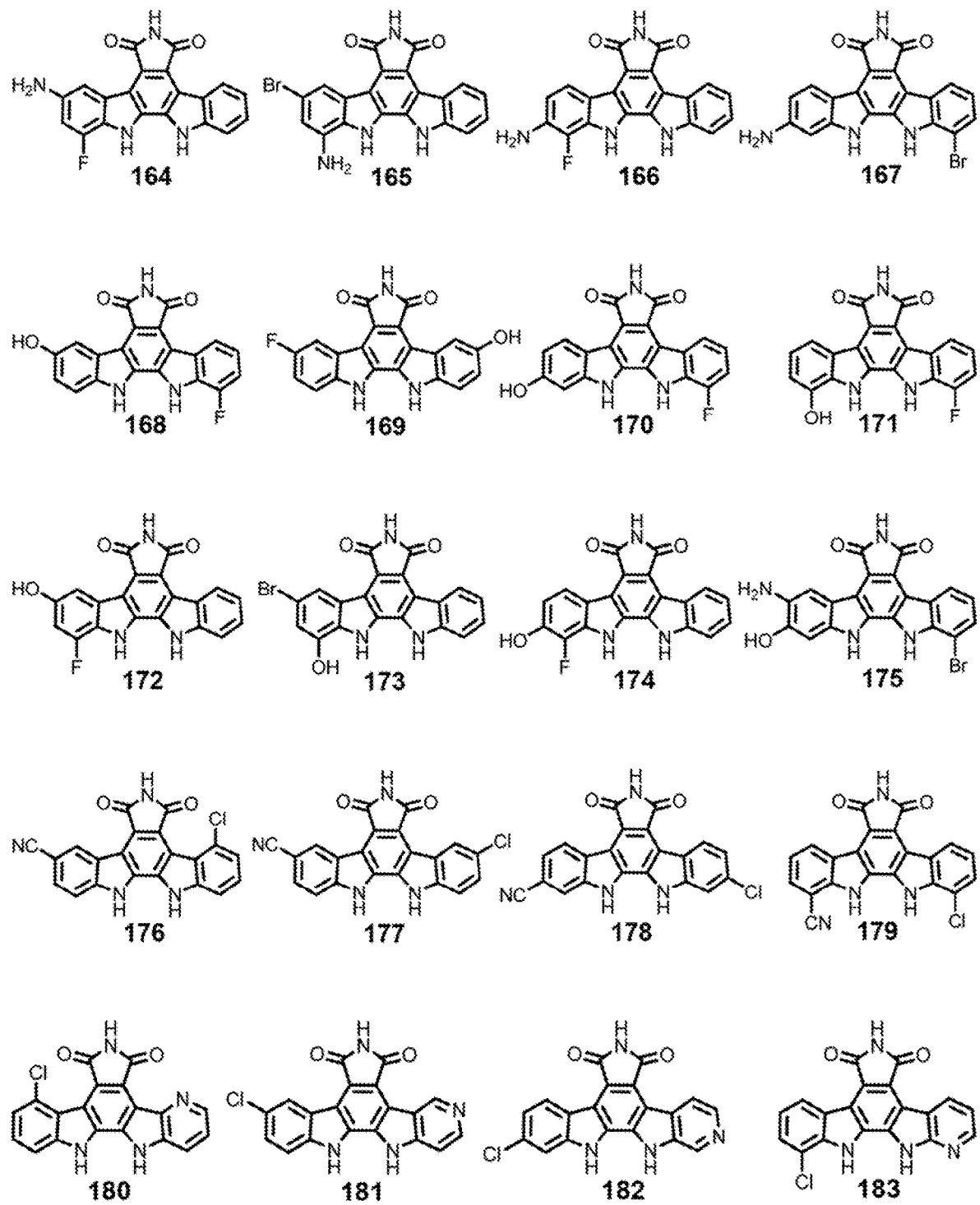
Figure 1L:
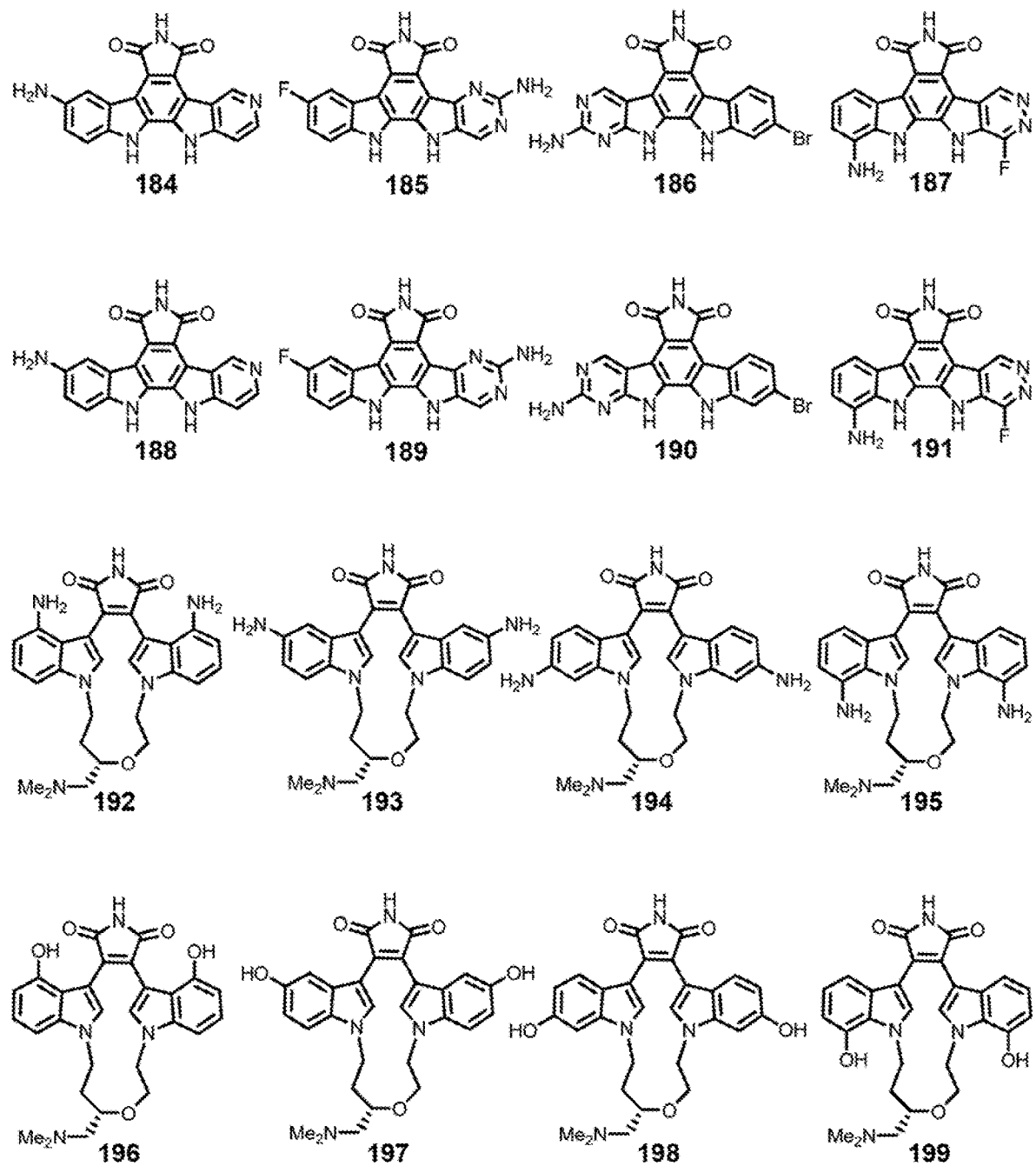
Figure 1M:
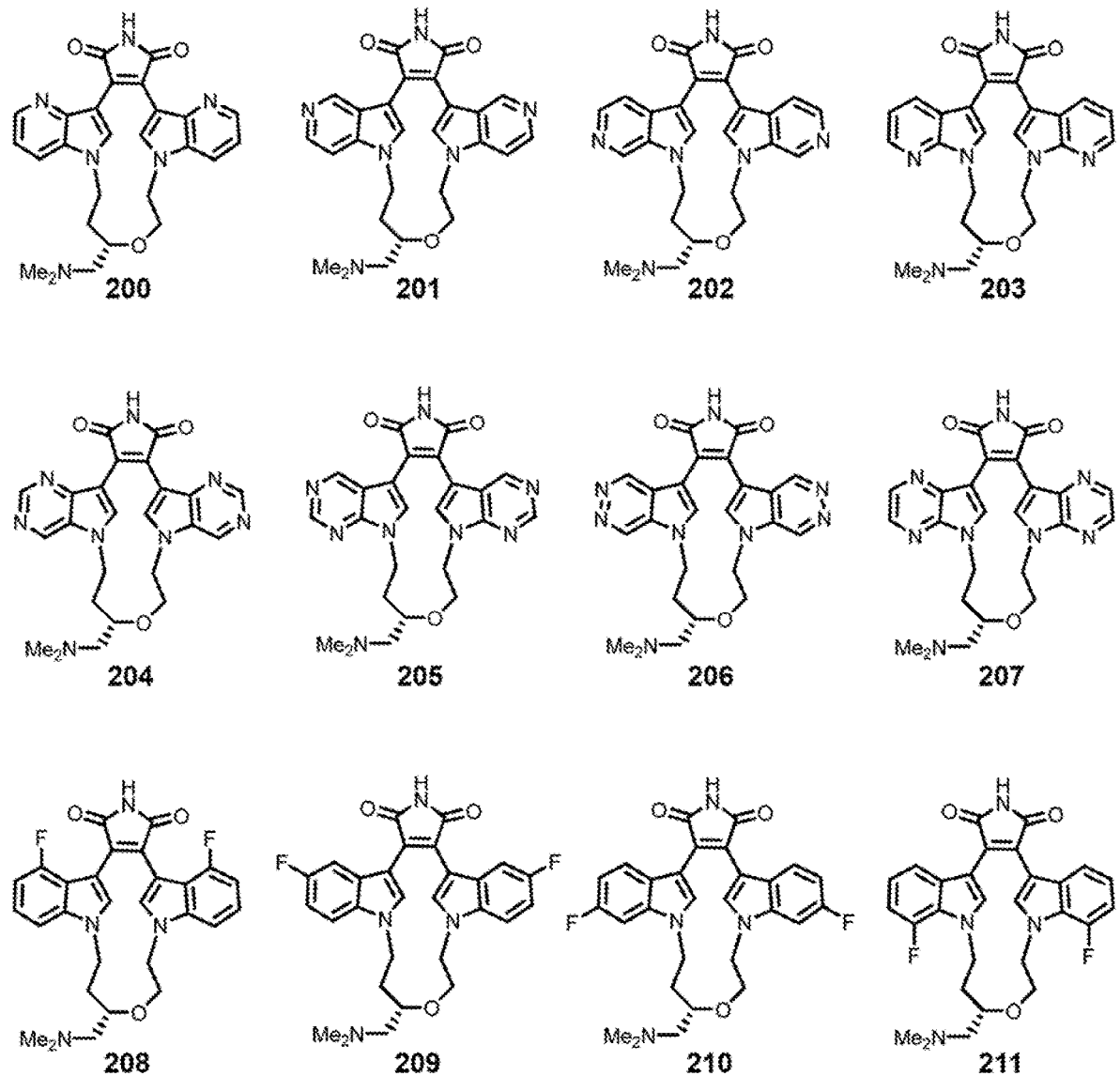
Figure 1N:
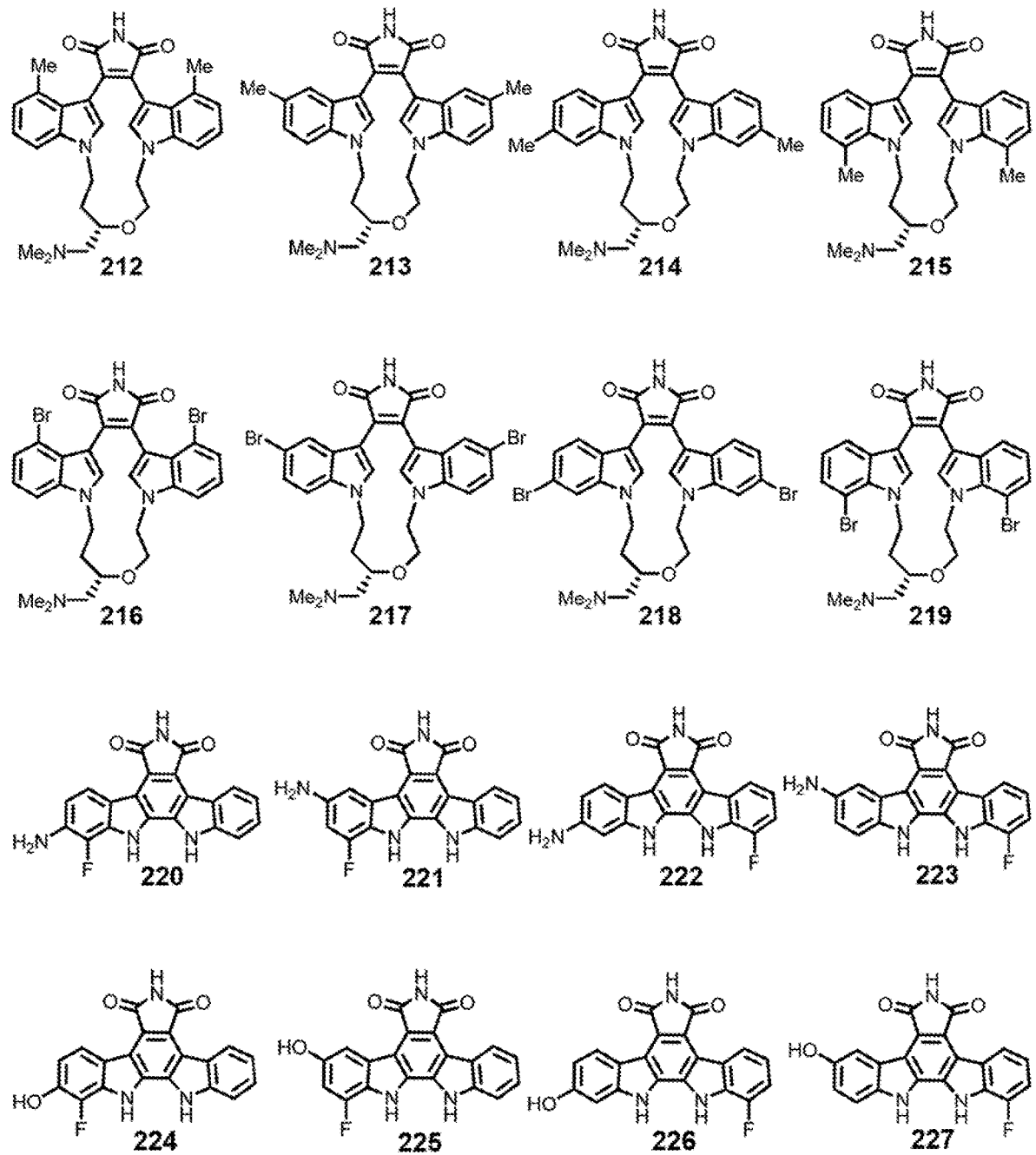
Figure 1O:
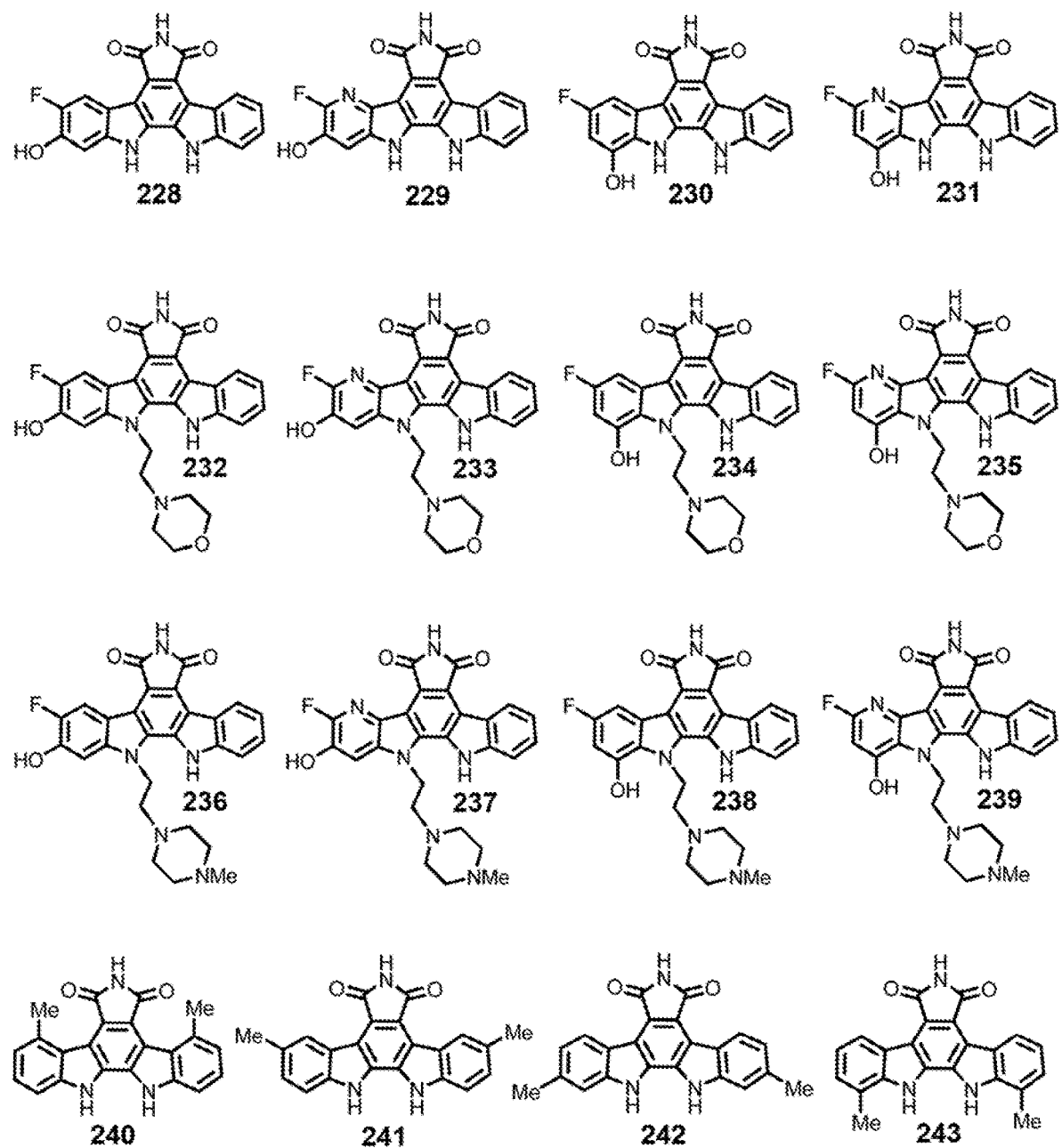
Figure 1P:
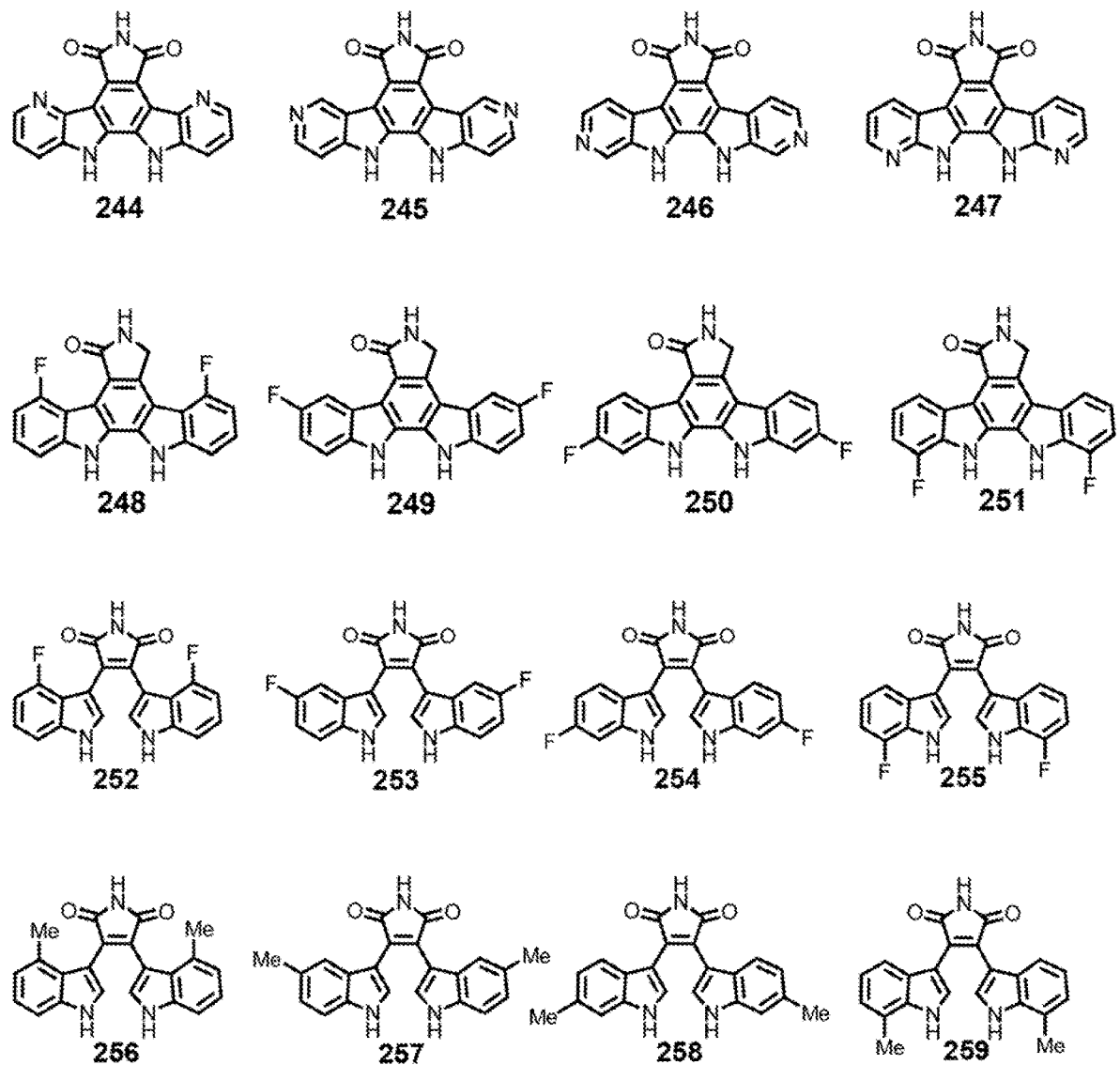
Figure 1Q:
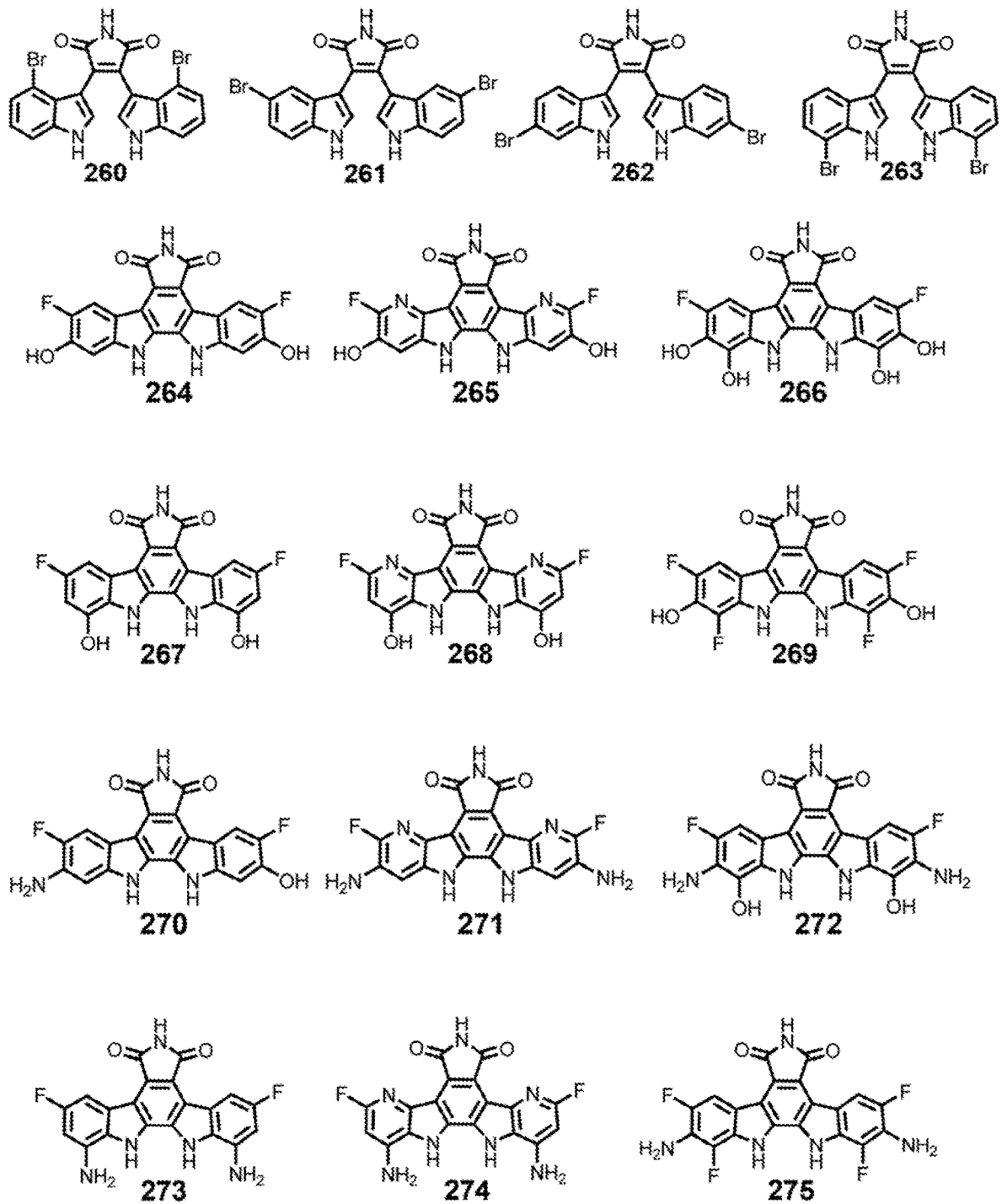
Figure 1R:
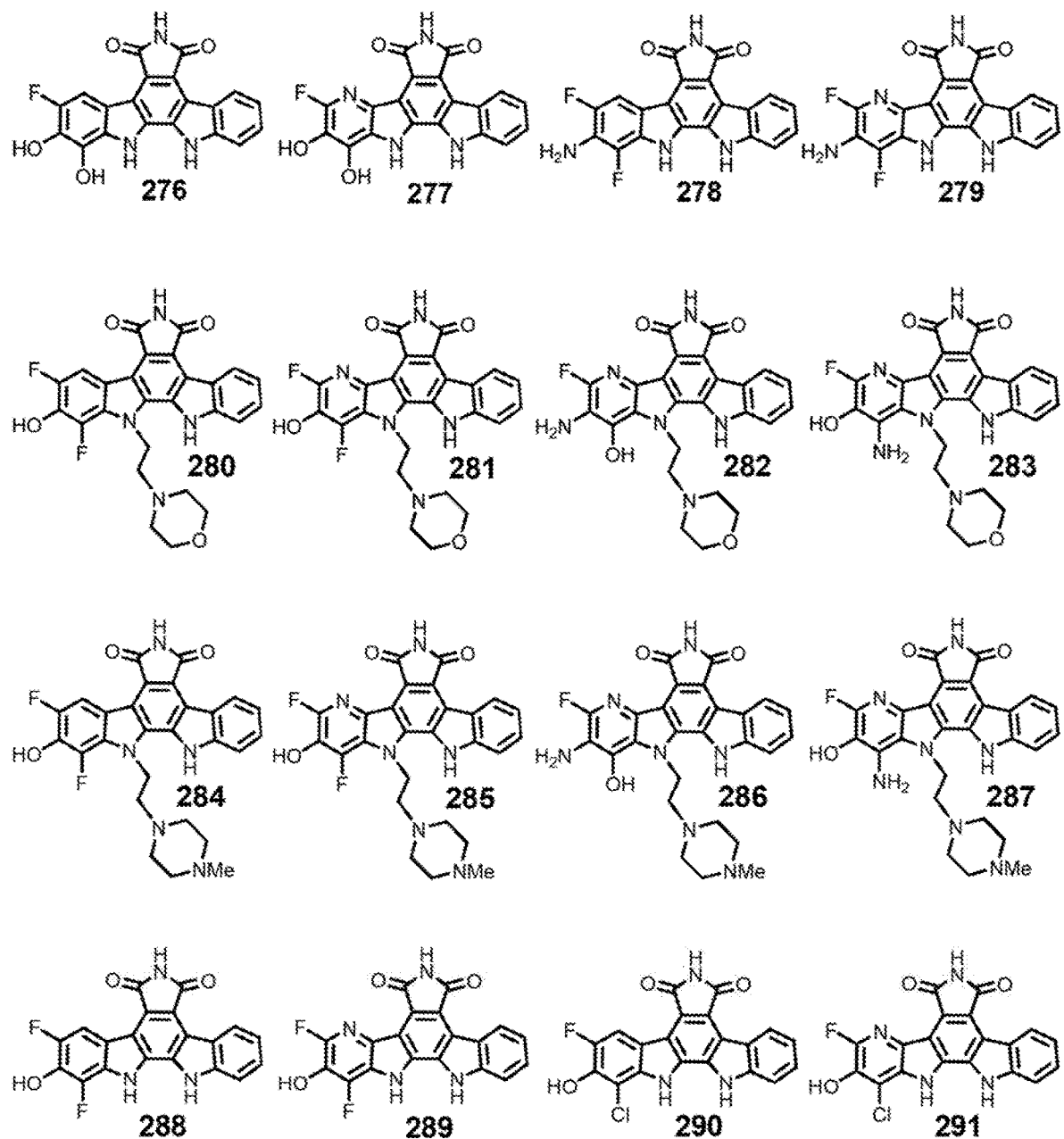
Figure 1S:
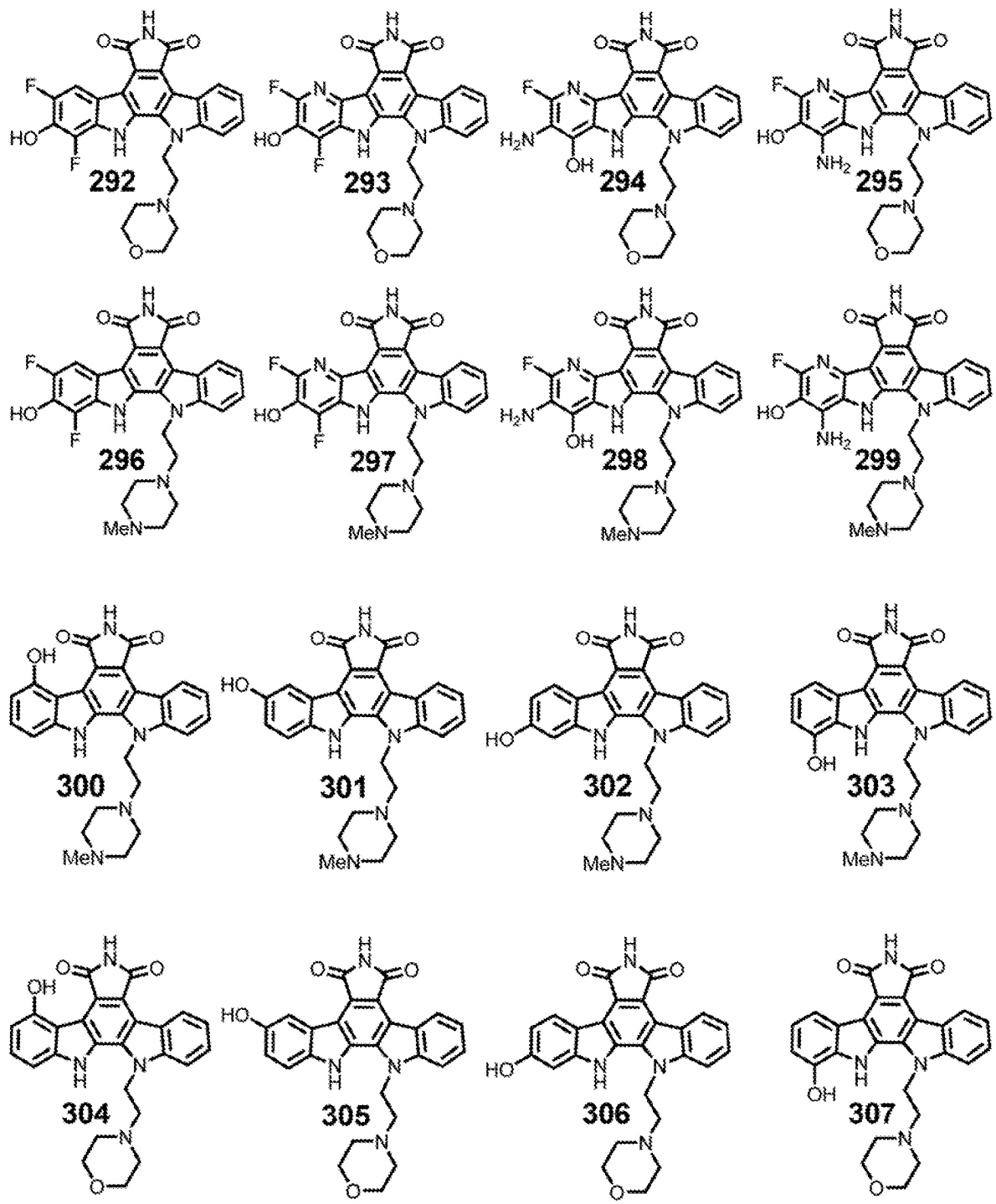

The novel features of the invention are set forth specifically in the appended claims. A better understanding of the features and advantages of the present invention will be obtained by reference to the following detailed description that sets forth illustrative embodiments, in which the principles of the invention are utilized. To facilitate a full understanding of the disclosure set forth herein, a number of terms are defined below.

Generally, the nomenclature used herein and the laboratory procedures in organic chemistry, medicinal chemistry, molecular biology, microbiology, biochemistry, enzymology, computational biology, computational chemistry, and pharmacology described herein are those well-known and commonly employed in the art. Unless defined otherwise, all technical and scientific terms used herein generally have the same meaning as commonly understood by one of ordinary skill in the art to which this disclosure belongs. Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 6$^{th}$ Ed., Ed.: Smith, M. B. and March, J., John Wiley & Sons, New York: 2007, the entire contents of which are hereby incorporated by reference.

Provided herein are compounds and methods for the treatment of certain forms of cancer by administration of selective inhibitors of PIM kinases to subjects in need thereof. In certain embodiments, the subject has been diagnosed with or is suspected of suffering from a cancer that is found to be associated with the overexpression or hyperactivity PIM kinases. Cancers of the endodermal organs, such as the stomach, liver, colon, pancreas and gallbladder, represent examples of cancers where PIM1 and/or PIM3 involvement has been demonstrated, and thus are candidates for treatment with an efficacious PIM1 and/or PIM3 inhibitor.

In some instances, provided herein are methods for treating cancerous conditions characterized by, for example, abnormal fatigue, pain, persistent lumps, bleeding, stiffness, dizziness, anemia, susceptibility to infection, persistent cough or itching, headaces, sudden weight loss, nonhealing sores, and fever. Cancerous malignancies can affect almost any part of the body, including the heart, brain, nerves, muscles, skin, eyes, joints, lungs, pancreas, prostate, reproductive organs, kidneys, glands, lymphatic system, immune system, gastrointestinal system, circulatory system and blood vessels.

Over 14 million new cancer cases were diagnosed and 8.2 million cancer-related deaths occurred globally in 2012, representing 0.12% of the world population (See: Global Cancer Facts & Figures, 3rd Edition, American Cancer Society; Atlanta, Ga., 2015). Projections indicate that these numbers will grow by up to 40% by 2030, indicating the critical need to develop new, more effective methods to treat this pernicious and pervasive disease and its multifarious indications.

PIM Kinases

The PIM kinases are a family of three constitutively active proto-oncogenic serine/threonine kinases, PIM1, PIM2, and PIM3, which were first identified in a series of retroviral insertional mutagenesis studies in c-Myc-induced murine lymphomas and named for the genomic site, Proviral Integration site of Moloney murine leukemia virus (See, for example: Cuypers, H. T., Cell, 1984, 37, 141-150; Mikkers, H., Nat. Genet., 2000, 32, 153-159). The PIM-1 gene encodes two proteins of 34 and 44 kDa due to the use of an alternative translation initiation at an upstream CUG codon. PIM-2 encodes for three isoforms (34, 38 and 40 kDa) and PIM3 is produced as a single 34 kDa protein (See: Brault, L., et al., Haematologica, 2010, 95, 1004-1015; Nawijn, M. C., Nat. Rev. Cancer, 2011, 11, 23-34). The PIM kinases are highly homologous at the amino acid level and in their kinase domains. The PIM-1 protein sequence is 61% identical to PIM-2 and 71% identical to PIM-3 and all PIM family members share a high level of conservation in the ATP-binding pocket. Consistent with this high level of homology, PIM kinases have been shown to exhibit some overlapping functions through both the in vitro identification of conserved substrate-binding sequences and in vivo redundancy, when examining cytokine-mediated cell growth and differentiation in knockout models (See: Bullock A N, et al., J. Biol. Chem., 2005, 280(50), 41675-41682). The PIM kinases differ in their normal tissue distribution. PIM-1 is expressed at higher levels in hematopoietic cells, whereas PIM-2 is more prevalent in brain and lymphoid cells and PIM-3 is more highly expressed under normal conditions in kidney, breast and brain cells (See: Eichmann A, et al., Oncogene, 2000, 19(9), 1215-1224).

Expression levels of PIM kinase mRNA and protein are regulated by intercellular and intracellular signaling molecules, including various growth factors, cytokines, chemokines and hormones, especially those of hematopoietic origin, such as IL-2, -3, -5, and -7, granulocyte-macrophage colony stimulating factor (GM-CSF), interferon gamma (IFN-γ), and erythropoietin. These molecules interact with their receptors, and activate downstream signaling pathways, including those involving JAK/STAT, PKC and NF-κB (See: Lilly, M., et al., Oncogene, 1999, 18, 4022-4031). The transcription factors STAT3/5 and NF-κB upregulate PIM transcript levels, which in turn upregulate PIM kinase protein levels.

In contrast to the majority of other kinases, PIM kinases are constitutively active enzymes that do not require post-translational modifications to induce their kinase activity. As they are short lived proteins (<5 min), their activity is largely regulated by protein stability, for example, through ubiquitylation and proteasomal degradation. (See: Shay K. P., et al., Mol. Cancer Res., 2005, 3:170-181).

The PIM kinases are also unusual in the structure of their kinase domains, where the hinge region of the ATP-binding pocket contains a proline residue not found in other kinases. This results in a molecular recognition motif that is unique among the kinase family as they are the only kinases that cannot form the canonical bidentate hydrogen bonds with ATP and ATP-competitive inhibitors due to the proline residue which resides at the position of the typical hydrogen-bond donor (See: Qian, K. C., et al., J. Biol. Chem., 2005, 280, 6130-6137; Kumar, A., et al., J. Mol. Biol., 2005, 348, 183-193; Jacobs, M. D., J. Biol. Chem., 2005, 280, 13728-13734).

PIM kinases regulate multiple pathways through its downstream substrates, including histone H3 and c-Myc which are co-activators of transcription, whereas 4E-BP1 and Bad are deactivated through phosphorylation to promote translation and cell survival processes. PIM kinases activate cdc25A/C, while repressing p21 and p27, to regulate cell cycle, and they also facilitate the formation of ABCB1 and ABCG2 efflux pumps which generate drug resistance. PIM kinases have been demonstrated to inhibit apoptosis by inducing antiapoptotic Bcl-2 expression or inactivating the pro-apoptotic protein BAD through phosphorylation on Ser112, Ser136, and Ser155, which leads to sequestration by the protein 14-3-3 (See, for example: Lilly, M., et al., Oncogene, 1999, 18, 4022-4031; Fox, C. J., Genes Dev., 2003, 17, 1841-1854; Yan, B., J. Biol. Chem., 2003, 278, 45358-45367, Macdonald, A., BMC Cell Biol., 2006, 7, 1). PIM-1/PIM-2/PIM-3 triple knockout mice are viable, but they are significantly smaller than their wild-type counterparts, clearly due to reduced cell proliferation (Mikkers, H., et al., Mol. Cell. Biol. 2004, 24, 6104-6115). Knockdown experiments by RNA interference or dominant-negative acting mutants suggested that PIM kinases are important for maintenance of a transformed phenotype.

The PIM kinases have been shown to be involved in regulating several important biological process including cell survival, proliferation, differentiation, and apoptosis. The PIM kinases support in vitro and in vivo tumor cell growth and survival through modification of a number of common as well as isoform-specific substrates, including several cell cycle regulators and apoptosis mediators. However, when these processes involving PIM kinases become disrupted or hyperactivated, they express the hallmarks of cancer and PIM kinases are notably involved in signaling mechanisms associated with tumorigenesis. For example, the PIM kinases share substrates such as BAD, p21, p27, and c-Myc and are favorable partners for Myc-induced tumorigenesis (See: Nawijn, M. C., Nat. Rev. Cancer, 2011, 11, 23-34). BAD phosphorylation on Ser112 and Ser136 induces 14-3-3 protein binding and seems to be required for phosphorylation on Ser155 (See: Danial, N. N., Oncogene, 2008, 27 (Suppl. 1), S53-S70; Zha, J., et al., Cell, 1996, 87, 619-628). Ser155 phosphorylation is the rate-limiting step for dissociation from BCL-2 and BCL-2-like 1 (BCLX; also known as BCL2L1) allowing these survival factors to inactivate BAX and BAK, resulting in an increased threshold for the induction of apoptosis. Moreover, Ser155 phosphorylation induces GCK binding by BAD, resulting in increased rates of glycolysis required by proliferating cancer cells. Consequently, Ser155 phosphorylation has been proposed to constitute a molecular switch between the pro-apoptotic and metabolic activities of BAD (See: Danial, N. N. et al., Nature, 2003, 424, 952-956). In addition, PIM kinases have been found to phosphorylate the insultin receptor substrates 1 and 2, at Ser1101 and Ser1149, respectively, which significantly decreases the half-life of IRS and leads to insulin resistance (See: Song, J. H., et al., Oncotarget, 2016, 7(15), 20152-20165).

Mechanistic studies have shown that high expression levels of PIM kinases are associated with hematologic and epithelial cancers in humans. The expression levels of individual PIM members vary among tumor types and numerous lines of evidence denote PIM kinases as proto-oncogenes (See: Brault, L., et al., Haematologica, 2010, 95, 1004-1015; Nawijn, M. C., Nat. Rev. Cancer, 2011, 11, 23-34). Pim-1 is up-regulated in B-cell non-Hodgkin's lymphoma, and this is generally correlated with poor prognosis. In addition, overexpression of Pim-1 is also noted in acute myeloid leukemia (AML) and nonhematologic cancers such as prostate. PIM1 is mainly overexpressed in acute myeloid leukemia and PIM2 plays a major role in multiple myeloma. PIM-1 and PIM-2 have been found to be overexpressed in solid tumors such as prostate cancer and a variety of human hematopoietic malignancies such as leukemia and lymphoma. PIM-3 is overexpressed in a range of endodermal cancer tissues and has been shown to promote the growth of Ewing's family tumor cell lines (See: Blanco-Aparicio, C., et al., Biochem. Pharmacol., 2013, 85, 629-643).

Importantly, PIM kinases often are abnormally expressed in malignant lesions, but not in the normal tissues and therefore represent attractive therapeutic targets (See, for example: Li Y Y., et al., Cancer Res., 2006, 66(13), 6741-6747; Zheng H C, et al., J. Cancer Res. Clin. Oncol., 2008, 134(4), 481-488; Pagano M A., et al., Mol. Cell. Biochem., 2005, 274(1-2), 23-29; Fujii C, et al., Int. J. Cancer, 2005, 114(2), 209-218).

PIM3 Kinase

PIM3 kinase has been found to be aberrantly expressed specifically in endodermal cancers of the human colon, stomach, liver, prostate, and pancreas, and inhibition of PIM3, for example with targeted shRNA, was shown to significantly increase levels of apoptosis and reduce proliferation (See: Li Y Y., et al., Cancer Res., 2006, 66(13), 6741-6747; Zheng H C, et al., J. Cancer Res. Clin. Oncol., 2008, 134(4), 481-488; Fujii C, et al., Int. J. Cancer, 2005, 114(2), 209-218; Popivanova B. K., et al., Cancer Sci., 2007, 98(3), 321-328; Qu, Y., et al., Med. Sci. Monit., 2016, 22, 4254-4260). In addition, PIM3 overexpression has been shown to be involved in other malignancies, such as cancer of the ovaries (Zhuang, H., et al., Asian Pac. J. Cancer Prev., 2015, 16(8), 3325-3331) and in glioblastomas (Quan, J., et al., Cell. Mol. Biol., 2015, 61(1), 42-50). Importantly, inhibition of PIM3 by a PIM1/3 inhibitor was shown to inhibit the growth of a range of pancreatic cancer cell lines, whereas a PIM1 selective inhibitor did not reduce growth of the same cell lines, demonstrating the dependence of pancreatic cancer growth an PIM3 kinase activity (See: Nakano, H., et al., Bioorg. & Med. Chem. Lett., 2015, 25, 5687-5693).

Endodermal cancers have been reported to be strongly dependent on PIM1 and/or PIM3 activity for survival and proliferation (See: Mukaida, N., et al., Cancer Sci., 2011; 102, 1437-1442; Li, Y. Y., et al., World J Gastroenterol., 2014; 20, 9392-9404.). Inhibition studies with a selective PIM3 inhibitor was able to show that PIM3, but not PIM1 or PIM2, positively regulates the IL-6/STAT3 pathway (Chang, M., et al., Mol. Cancer Ther. 2010, 9(9), 2478-87). The STAT3 pathway is upregulated in a variety of different cancers, and particularly prostate cancer.

Toxicity is important to consider when developing a new therapeutic agent. Data has shown that a deficiency of the PIM3 gene does not result in apparent phenotypic changes in mice, suggesting that PIM3 may be physiologically dispensable in normal tissues. Moreover, unlike another survival kinase, namely Akt kinase, PIM kinases are not localized downstream of the insulin receptor signaling pathway and therefore inhibition of the PIM kinases appears to have few effects on normal metabolism (Amaravadi R, and Thompson C B., J. Clin. Invest., 2005; 115: 2618-2624). Thus, targeting PIM represents a novel approach for developing safer and more effective drugs for treating solid tumors in which PIM kinases, and particularly PIM1 and/or PIM3, are aberrantly expressed.

PIM Inhibitors

The proto-oncogenic nature of the PIM kinases and direct validation of their involvement in the pathology of numerous cancers has inspired interest in developing inhibitors for the PIM kinases. In general, most efforts to date have focused on inhibitors that are selective for PIM1 or are pan-PIM inhibitors (inhibit all PIM kinases), with only a few examples demonstrating PIM3 selective inhibitors. Designing selective inhibitors has been challenging as all PIMs share high homology and the unique feature of being the only kinases with a proline in the hinge, which results in only one hydrogen bond interaction with ATP or an inhibitor (See: Qian, K. C., et al., J. Biol. Chem., 2005, 280, 6130-6137). Also as the ATP Km for PIM2 is 10-100× lower than that for PIM1 and PIM3, cell active pan PIM inhibitors have been more challenging to identify than PIM1 or PIM1/3 inhibitors. Example are provided below.

PIM1 and Pan PIM Inhibitors

SuperGen/Astex Pharmaceuticals has described imidazo [1,2-b]pyridazine and pyrazolo[1,5-a]pyrimidine derivatives as PIM1 selective inhibitors for leukemia and prostate cancer, including SGI-1776, which failed in Phase 1 trials due to high hERG-mediated cardiotoxicity, and the PIM/3 inhibitor SGI-9481 (Chen, L. S., et al., Blood. 2009; 114: 4150-4157; Bearss D J, et al., PCT Patent Application No. WO 2008058126A2). Novartis reported a series of potent pan-PIM inhibitors, including LGB321 and the aminocyclohexyl pyridylcarboxamide PIM447 (LGH447), which is in Phase I clinical trials for refractory multiple myeloma and other hematological malignancies (See: Burger, M. T., et al., ACS Med. Chem. Lett., 2013, 4, 1193-1197; Burger, M. T., et al., J. Med. Chem., 2015, 58, 8373-8386; Burger, M., et al., US Patent Application No. 2010/0216839; Burger, M., et al., US Patent Application No. 2014/0228363; Burger, M., et al., US Patent Application No. 2015/0336960). Cyclene reported a series of different PIM inhibitors, including the dual CK2/PIM1 inhibitor CX-4595 which was in Phase I trials for refractory multiple myeloma and other cancers, and the pan-PIM inhibitor CX-6258 (See: Chua, P. C., et al., U.S. Pat. No. 8,168,651B2; Siddiqui-Jain A., et al., Cancer Res., 2010, 70(24), 10288-10298; Pierre F., et al., Bioorg. Med. Chem. Lett., 2011, 21(22), 6687-6692; Haddach, M., et al., ACS Med. Chem. Lett., 2012, 3, 135-139). AstraZeneca has developed highly potent pan-PIM inhibitors, including AZD-1208, which is in Phase I trials for acute myeloid leukemia (See: Dakin, L. A., et al., Bioorg. Med. Chem. Lett., 2012, 22, 4599-4604; Keeton E. K., et al., Blood, 2014, 123(6), 905-913; Dakin, L., et al., PCT Patent Application No. WO 2010/001169 A2; Dakin, L., et al., U.S. Pat. No. 8,901,307 B2). AZD-1208 apparently has experienced challenges in the clinic due to unexpectedly high CYP3A4-mediated clearance and associated lack of efficacy (See: Cortes, J., et al., Proceedings: AACR 107th Annual Meeting 2016; New Orleans, La., DOI: 10.1158/1538-7445.AM2016-CT147). Abbott reported potent pan-PIM inhibitors based on a series of pyrimidin-4-one compounds (See: Tao, Z.-F., et al., J. Med. Chem., 2009, 52, 6621-6636).

Biogen Idec has designed potent pyrrolopyrimidine-based PIM1/3 inhibitors (See: Ishchenko, A., et al., Bioorg. Med. Chem. Lett., 2015, 25, 474-480). Genetech/Roche have discovered a range of PIM inhibitors, including a series of pan-PIM inhibitors based on pyrazolo[1,5-a]pyrimidines (GNE-652) with picomolar potency (See: Wang, X., et al., Bioorg. Med. Chem. Lett., 2013, 23, 3149-3153; Wang, X., US Patent Application No. 2014/0128376 A1; Wang, X., U.S. Pat. No. 9,573,943 B2; Do, S., et al., U.S. Pat. No. 9,434,725 B2). Incyte has reported aromatic carboxamide-based PIM inhibitors (See: Li, Y.-L., et al., U.S. Pat. No. 9,676,750 B2). Jikai Biosciences has described pan-PIM inhibitors (See: Ge, J., U.S. Pat. No. 9,452,995 B2). Nerviano Medical Sciences has reported potent pyrrolo[1,2-a]pyrazinones inhibitors of PIM1 and 2 (See: Casuscelli, F., et al., Bioorg. Med. Chem., 2013, 21, 7364-7380). Finally a team from Japan has described potent inhibitors of PIM1/3 (See: Nakano, H., et al., Bioorg. Med. Chem. Lett., 2015 25, 5687-5693; Nakano, H., et al., ACS Med. Chem. Lett., 2017, 8, 504-509; Nagano, T., et al, US Patent Application No. US2017/0145005).

PIM3 Selective Inhibitors

To our knowledge, there are few reports describing kinase inhibitors that selectively inhibit PIM3 relative to the other PIM isoforms. The inhibitor M-110 was reported to display a 50× preference for PIM3 over PIM1 and PIM2, but was based on the hydrozone functionality which is a metabolically unstable group in vivo (See: Chang, M., et al., Mol. Cancer Ther. 2010, 9(9), 2478-2487). The other example of a PIM3 selective inhibitor is ruboxistaurin, which originally was developed clinically as a protein kinase C beta inhibitor, but subsequently also was shown to bind PIM3 ($K_d$ 12 nM) with 23× and 140× selectivity over PIM1 and PIM2, respectively (See: Karaman, M. W., et al., Nat. Biotechnol., 2008, 26, 127-132; Jirousek, M. R., et al., J. Med. Chem., 1996, 39, 2664-2671). The ability to readily modify the structure of the indole and macrocyclic rings of ruboxistaurin may enable further enhancement of PIM3 selectivity and simultaneously reduce activity against PKC kinases, thus representing an opportunity to develop highly selective PIM3 inhibitors for treating cancer.

Described herein are inhibitors of the PIM kinases, with certain compounds exhibiting selective inhibition of PIM3. Highly selective PIM3 inhibitors are useful for specifically treating cancers that express and/or depend on the activity of this kinase for its pathological growth and proliferation. Endodermal cancers, including malignancies of the stomach, colon, liver, pancreas, prostate, and gallbladder, have been shown to overexpress PIM3 and inhibition of PIM3 has been demonstrated to inhibit growth of these cancers. Also described herein are pharmaceutical compositions comprising PIM inhibitors (e.g., PIM inhibitor compounds described herein) for reversing or reducing one or more of the negative symptoms associated with cancerous malignancies, including endodermal cancers. Also described herein are pharmaceutical compositions comprising PIM inhibitors (e.g., PIM inhibitor compounds described herein) for halting or delaying the progression of negative symptoms associated with cancerous malignancies, including endodermal cancers. Described herein is the use of a PIM inhibitor for manufacture of a medicament for treatment of one or more symptoms of cancer.

In some embodiments, the PIM inhibitors described herein inhibit all PIM kinases with approximately equal potency. In certain embodiments, a PIM inhibitor described herein reduces or inhibits the activity of one or more of PIM kinases while largely not affecting the activity of the others.

In some embodiments, a PIM inhibitor described herein substantially reduces or inhibits the kinase activity of PIM3. In some embodiments, a PIM inhibitor described herein is a substantially complete inhibitor of the PIM3 kinase. As used herein, "substantially complete inhibition" means, for example, >95% inhibition of PIM3. In other embodiments, "substantially complete inhibition" means, for example, >90% inhibition of PIM3. In some other embodiments, "substantially complete inhibition" means, for example, >80% inhibition of PIM3. In some embodiments, a PIM3 inhibitor described herein is a partial inhibitor of PIM3. As used herein, "partial inhibition" means, for example, between about 40% to about 60% inhibition of PIM3. In other embodiments, "partial inhibition" means, for example, between about 50% to about 70% inhibition of PIM3. As used herein, where a PIM3 inhibitor substantially inhibits or partially inhibits the activity of PIM3 while largely not affecting the activity of PIM1 and/or PIM2, it means, for example, less than about 10% inhibition of PIM1 and/or PIM2 when PIM1 and/or PIM2 are contacted with the same concentration of the PIM3 inhibitor. In other instances, where a PIM3 inhibitor substantially inhibits or partially inhibits the activity of PIM3 while not affecting the activity of PIM1 and/or PIM2, it means, for example, less than about 5% inhibition of PIM1 and/or PIM2 when PIM1 and/or PIM2 are contacted with the same concentration as used for PIM3. In yet other instances, where a PIM3 inhibitor substantially inhibits or partially inhibits the activity of PIM3 while largely not affecting the activity of PIM1 and/or PIM2, it means, for example, less than about 1% inhibition of PIM and/or PIM2 when PIM and/or PIM2 is contacted with the same concentration of the PIM3 inhibitor as used for PIM3.

In one aspect of this invention is a compound having the structure of Formula (I) or a pharmaceutically acceptable salt, solvate, hydrate, N-oxide, prodrug, stereoisomer, enantiomer, mixture of enantiomers, mixture of diastereomers, isotopic variants, and metabolites thereof; wherein:

Formula (I)

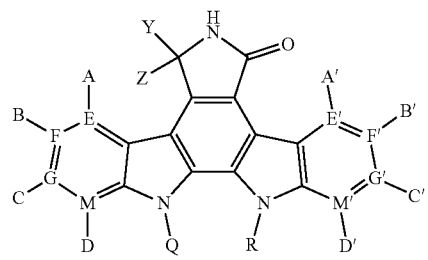

Each A, B, C, and D is the same or different and independently selected from H, halogen, —$N_3$, —CN, —$NO_2$, —OH, —$OCF_3$. —$OCH_2F$, —$OCF_2H$, —$CF_3$, —$SR^1$, —S(=O)$R^2$, —S(=O)$_2R^2$, —OS(=O)$_2F$, —OS(=O)$_2$(O$R^2$), —S(=O)$_2$(O$R^2$), —$NR^3$S(=O)$_2R^2$, —S(=O)$_2$N($R^3$)$_2$, —OC(=O)$R^2$, —$CO_2R^3$, —$OR^3$, —N($R^3$)$_2$, —$NR^3$C(=O)$R^2$, —$NR^3$C(=O)O$R^3$, —$NR^3$C(=O)N($R^3$)$_2$, —$CH_2NH_2$, —$CH_2N(R^3)_2$, —$CH_2SR^1$, —C(=O)$NH_2$, —C(=O)N($R^3$)$_2$, —C(=O)$R^3$, substituted or unsubstituted alkyl, substituted or unsubstituted alkenyl, substituted or unsubstituted alkynyl, substituted or unsubstituted alkoxy, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or an optional substituent selected, for example, haloalkyl, alkenyl, arylalkyl, alkoxyalkyl, hydroxyalkyl, monoalkylaminoalkyl, dialkylaminoalkyl, acylaminoalkyl, acyloxyalkyl, cyanoalkyl, amidinoalkyl, carboxyalkyl, alkoxycarbonylalkyl, aminocarbonylalkyl, aryl, alkylaryl, aminoalkyl, heteroaryl, carbonylalkyl, amidinothioalkyl, nitroguanidinoalkyl, a protecting group, a glycose, aminoglycose or alkylglycose residue;

Each A', B', C', and D' is the same or different and independently selected from H, halogen, $-N_3$, $-CN$, $-NO_2$, $-OH$, $-OCF_3$, $-OCH_2F$, $-OCF_2H$, $-CF_3$, $-SR^1$, $-S(=O)R^2$, $-S(=O)_2R^2$, $-OS(=O)_2F$, $-OS(=O)_2(OR^2)$, $-S(=O)_2(OR^2)$, $-NR^3S(=O)_2R^2$, $-S(=O)_2N(R^3)_2$, $-OC(=O)R^2$, $-CO_2R^3$, $-N(R^3)_2$, $-OR^3$, $-NR^3C(=O)R^2$, $-NR^3C(=O)OR^3$, $-NR^3C(=O)N(R^3)_2$, $-CH_2NH_2$, $-CH_2N(R^3)_2$, $-CH_2SR^1$, $-C(=O)NH_2$, $-C(=O)N(R^3)_2$, $-C(=O)R^3$, substituted or unsubstituted alkyl, substituted or unsubstituted alkenyl, substituted or unsubstituted alkynyl, substituted or unsubstituted alkoxy, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or an optional substituent selected, for example, haloalkyl, alkenyl, arylalkyl, alkoxyalkyl, hydroxyalkyl, monoalkylaminoalkyl, dialkylaminoalkyl, acylaminoalkyl, acyloxyalkyl, cyanoalkyl, amidinoalkyl, carboxyalkyl, alkoxycarbonylalkyl, aminocarbonylalkyl, aryl, alkylaryl, aminoalkyl, heteroaryl, carbonylalkyl, amidinothioalkyl, nitroguanidinoalkyl, a protecting group, a glycose, aminoglycose or alkylglycose residue;

Each E, F, G, and M is independently C or N;

Each E', F', G', and M' is independently C or N;

Each Y and Z is independently H, $-OH$, $-OR^3$, $N(R^3)_2$, halogen, $-N_3$, substituted or unsubstituted alkyl, substituted or unsubstituted alkenyl, substituted or unsubstituted alkynyl, substituted or unsubstituted alkoxy, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or Y and Z can be combined together to represent O, N(NR$^3$), N(OH), or S corresponding to C=O, C=NNR$^3$, C=NOH, or C=S groups, respectively;

R$^1$ is H or linear or branched substituted or unsubstituted alkyl, substituted or unsubstituted alkenyl, substituted or unsubstituted cycloalkyl, substituted or unsubstituted cycloalkenyl, substituted or unsubstituted heterocycloalkyl, substituted or unsubstituted aryl or substituted or unsubstituted heteroaryl;

R$^2$ is linear or branched substituted or unsubstituted alkyl, substituted or unsubstituted alkenyl, substituted or unsubstituted cycloalkyl, substituted or unsubstituted cycloalkenyl, substituted or unsubstituted heterocycloalkyl, substituted or unsubstituted aryl or substituted or unsubstituted heteroaryl;

Each R$^3$ is independently H, linear or branched substituted or unsubstituted alkyl. substituted or unsubstituted alkenyl, substituted or unsubstituted cycloalkyl, substituted or unsubstituted cycloalkenyl, substituted or unsubstituted heterocycloalkyl substituted or unsubstituted aryl, substituted or unsubstituted heteroaryl, or substituted or unsubstituted acyl ($-C(=O)R^1$), or two R$^3$ together with the atoms to which they are attached form a substituted or unsubstituted heterocycle;

Each Q and R is independently H, $-S(=O)R^2$, $-S(=O)_2 R^2$, $-NR^3S(=O)_2R^2$, $-S(=O)_2N(R^3)_2$, $-C(=O)R^2$, $-CO_2R^3$, $-N(R^3)_2$, $-C(O)N(R^3)_2$, linear or branched substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, natural or non-natural substituted or unsubstituted glycose, natural or non-natural substituted or unsubstituted glycose aminoglycose groups, natural or non-natural substituted or unsubstituted glycose alkylglycose groups, natural or non-natural substituted or unsubstituted glycose, aminoglycose, or alkylglycose where Q and R are linked, substituted or unsubstituted alkyl where Q and R are linked, substituted or unsubstituted heteroalkyl where Q and R are linked, substituted or unsubstituted cycloalkyl where Q and R are linked, substituted or unsubstituted heterocycloalkyl where Q and R are linked, substituted or unsubstituted aryl where Q and R are linked, or substituted or unsubstituted heteroaryl where Q and R are linked to form a ring; Compounds of Formula (I) are themselves useful as protein kinase inhibitors or represent intermediates useful for the preparation of compounds exhibiting kinase inhibitory activity. As noted above, kinase inhibitors are useful for treating a variety of conditions including cancer, central nervous system disorders, Alzheimer's, cardiovascular disease, dermatological diseases, inflammation, autoimmune diseases such as rheumatoid arthritis, and diabetic complications.

In another embodiment of the invention are compounds having the structure of Formula (II) or a pharmaceutically acceptable salt, solvate, hydrate, N-oxide, prodrug, stereoisomer, enantiomer, mixture of enantiomers, mixture of diastereomers, isotopic variants, and metabolites thereof, which are examples representing kinase inhibitors, wherein:

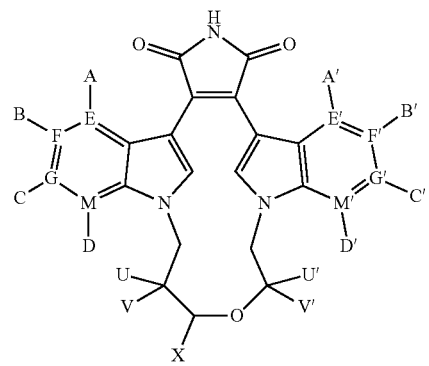

Formula (II)

Each A, B, C, D, A', B', C', D', E, F, G, M, E', F', G', M', R$^1$, R$^2$, R$^3$, Y, and Z is as defined above; Each U, V, U' and V' is independently H, OH, OR$^3$, N(R$^3$)$_2$, halogen, $-N_3$, substituted or unsubstituted alkyl, substituted or unsubstituted alkenyl, substituted or unsubstituted alkynyl, substituted or unsubstituted alkoxy, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or U and V and/or U' and V' can be combined together to represent O, N(NR$^3$), N(OH), or S corresponding to C=O, C=NNR$^3$, C=NOH, or C=S groups, respectively;

Each X is H, $-OH$, $-OR^3$, N(R$^3$)$_2$, halogen, $-N_3$, $-NO_2$, substituted or unsubstituted alkyl, substituted or unsubstituted alkenyl, substituted or unsubstituted alkynyl, substituted or unsubstituted alkoxy, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

In one embodiment of the invention are compounds of Formulas (I) and (II) wherein unsubstituted alkyl is selected from methyl, ethyl, n-propyl, iso-propyl, n-butyl, iso-butyl, tert-butyl, n-pentyl, n-hexyl, etc. In another embodiment, A, B, C, and D each are independently H, F, Cl, Br, I, —OH, —CN, —N$_3$, —OR$^3$, —NO$_2$, —NH$_2$, —CH$_2$NH$_2$, —CH$_2$N(R$^3$)$_2$, —CH$_2$SR$^1$, —C(=O)NH$_2$, —C(=O)N(R$^3$)$_2$, —C(=O)R$^3$, substituted 1,2,3-triazole, substituted or unsubstituted aryl, substituted or unsubstituted heteroaryl, substituted or unsubstituted alkenyl, substituted or unsubstituted alkynyl, or substituted or unsubstituted acyl; In another embodiment, A', B', C', and D' are independently H, F, Cl, Br, I, —OH, —CN, —N$_3$, —OR$^3$, —NO$_2$, —NH$_2$, —CH$_2$NH$_2$, —CH$_2$N(R$^3$)$_2$, —CH$_2$SR$^1$, —C(=O)NH$_2$, —C(=O)N(R$^3$)$_2$, —C(=O)R$^3$, substituted 1,2,3-triazole, substituted or unsubstituted aryl, substituted or unsubstituted heteroaryl, substituted or unsubstituted alkenyl, substituted or unsubstituted alkynyl, or substituted or unsubstituted acyl; In another embodiment, E, F, G, or M are independently nitrogen. In another embodiment, E', F', G', or M' are independently nitrogen. In another embodiment, E and F are nitrogen. In another embodiment, E' and F' are nitrogen. In another embodiment, E and F are nitrogen. In another embodiment, E and G are nitrogen. In another embodiment, E' and G' are nitrogen.

In another embodiment, E and M are nitrogen. In another embodiment, E' and M' are nitrogen. In another embodiment, F and M are nitrogen. In another embodiment, F' and M' are nitrogen.

In another embodiment of the invention are compounds of Formula (II) wherein Y, Z, Y', and Z' are hydrogen, and X is —CH$_2$N(Me)$_2$.

In alternative embodiments, provided herein are methods to produce bisindole alkaloids and analogs of Formulas (I) through a coupled transcription/translation (TX-TL) cell-free biosynthesis (CFB) system, wherein reactions are conducted by adding bisindole alkaloid pathway genes to cell-free extracts containing metabolic enzymes, salts, co-factors, amino acids, sugars, nucleotides, and precursor molecules such as tryptophan and/or tryptophan derivatives, and wherein optionally the mixture is capable of in vitro transcription, translation and/or coupled transcription/translation to produce molecules of Formula (I) where Q and R independently are either hydrogen, a glycose group attached to one indole nitrogen atom, or together form a glycose that bridges both indole nitrogen atoms. Compounds of Formula (I) subsequently may be produced through chemical transformations that introduce non-hydrogen Q and R groups.

In alternative embodiments, provided herein are methods to produce bisindole alkaloids and analogs of Formulas (II) through a coupled transcription/translation (TX-TL) cell-free biosynthesis (CFB) system, wherein reactions are conducted by adding bisindole alkaloid pathway genes to cell-free extracts containing metabolic enzymes, salts, co-factors, amino acids, sugars, nucleotides, and precursor molecules such as tryptophan and/or tryptophan derivatives, and wherein optionally the mixture is capable of in vitro transcription, translation and/or coupled transcription/translation to produce molecules of Formula (III), wherein.

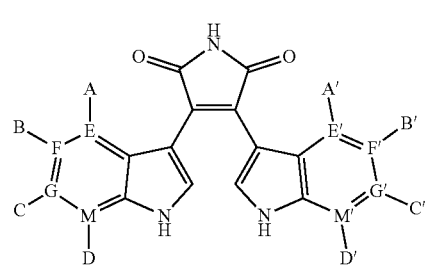

Formula (III)

Each A, B, C, D, A', B', C', D', E, F, G, M, E', F', G', M', R$^1$, R$^2$, and R$^3$ is as defined above for Formula (I);

Compounds of Formula (II) subsequently may be produced through chemical transformations that attach the macrocyclic group to Formula (III), by reacting, by way of example, with intermediates of general Formula (IV), wherein.

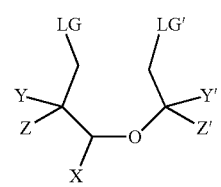

Formula (IV)

X, Y, Z, Y', Z' are defined above and LG and LG' are each independently the same or different leaving groups, such as but not limited to, iodine, bromine, chlorine, O-tosylate, O-mesylate, or together forming a cyclic sulfate.

In alternative embodiments, cell-free extracts are created by growing and breaking open cells, removing cell membrane and cell wall materials, and digesting native DNA and/or RNA, wherein the cells derive from different kingdoms, phyla, classes, orders, families, genera or species and the cells are a prokaryotic or a eukaryotic cell; or, a bacterial cell, a fungal cell, an algae cell, an Archaeal cell, a yeast cell, an insect cell, a plant cell, a mammalian cell or a human cell.

In alternative embodiments, provided herein are methods to produce bisindole alkaloids and analogs of Formulas (I) and (II) through cell-free reactions involving the use of isolated enzymes corresponding to the natural or unnatural pathway enzymes for bisindole alkaloid synthesis, wherein tryptophan and/or tryptophan derivatives are combined with such enzymes to afford molecules of Formula (I) and (III).

Also provided herein are pharmaceutical compositions comprising a compound disclosed herein, e.g., a compound of Formulas (I) and (II), including a stereoisomer, enantiomer, mixture of enantiomers, mixture of diastereomers, or isotopic variant thereof; or a pharmaceutically acceptable salt, solvate, hydrate, or prodrug thereof; and one or more pharmaceutically acceptable excipients.

Further provided herein is a method of treating, preventing, or ameliorating one or more symptoms of a disorder, disease, or condition involving PIM3 expression in a subject, comprising administering to the subject a therapeutically effective amount of a compound disclosed herein, e.g., a compound of Formulas (I) or (II), including a stereoisomer, enantiomer, mixture of enantiomers, mixture of diastereomers, or isotopic variant thereof; or a pharmaceutically acceptable salt, solvate, hydrate, or prodrug thereof.

Also provided herein is a method of treating, preventing, or ameliorating one or more symptoms of a disorder, disease, or condition in a subject, including cancers of endodermal organs such as the stomach, liver, colon, pancreas, prostate, and gallbladder, as well as other cancers involving PIM3 expression, comprising administering to the subject a therapeutically effective amount of a compound disclosed herein, e.g., a compound of Formulas (I) or (II), including a stereoisomer, enantiomer, mixture of enantiomers, mixture of diastereomers, or isotopic variant thereof; or a pharmaceutically acceptable salt, solvate, hydrate, or prodrug thereof.

Additionally provided herein is a method of modulating PIM kinase activity, comprising contacting a PIM kinase in vitro or in vivo with a therapeutically effective amount of a compound disclosed herein, e.g., a compound of Formulas (I) or (II), including a stereoisomer, enantiomer, mixture of enantiomers, mixture of diastereomers, or isotopic variant thereof; or a pharmaceutically acceptable salt, solvate, hydrate, or prodrug thereof.

Also provided herein is a method of treating, preventing, or ameliorating one or more symptoms of a PIM kinase-mediated disorder, disease, or condition in a subject, comprising administering to the subject a therapeutically effective amount of a compound disclosed herein, e.g., a compound of Formulas (I) or (II), including a stereoisomer, enantiomer, mixture of enantiomers, mixture of diastereomers, or isotopic variant thereof; or a pharmaceutically acceptable salt, solvate, hydrate, or prodrug thereof, wherein the compound partially or completely inhibits PIM activity and displays increased potency against one PIM kinase and/or increased selectivity for inhibiting one PIM kinase relative to the other two PIM kinases and relative to other kinases known to be present in the human body.

A further aspect of this invention are exemplary compounds having the structures shown in FIG. 1, wherein the structures provided are representative and are not meant to be comprehensive, and wherein indole aromatic substitution can occur in either a symmetric manner on both indole phenyl rings, as depicted, or in an asymmetric manner wherein each phenyl ring is differently substituted, and wherein the structures represent examples of Formula (I) wherein Y and Z are together C=O and Q and R each are independently H or a heteroatom-containing tail attached to the indole N, as represented in Formula (V), and the heteroatom-containing tail is a linear or branched alkyl chain that contains a substituted or unsubstituted heteroalkyl, substituted or unsubstituted heterocycloalkyl, or substituted or unsubstituted heteroaryl group.

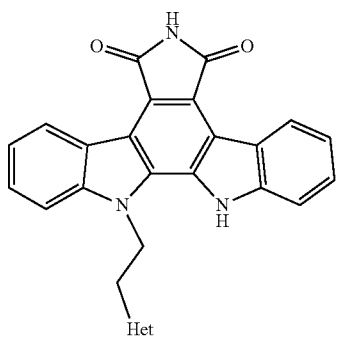

Formula (V)
Het = heteroatom-containing chain

Exemplary compounds of Formula (I) include those shown in FIG. 1, or a pharmaceutically acceptable salt, solvate, hydrate, N-oxide, prodrug, stereoisomer, enantiomer, mixture of enantiomers, mixture of diastereomers, isotopic variants, and metabolites thereof.

In some embodiments, a PIM inhibitor is a small molecule. As referred to herein, a "small molecule" is an organic molecule that is less than about 5 kilodaltons (kDa) in size. In some embodiments, the small molecule is less than about 4 kDa, 3 kDa, about 2 kDa, or about 1 kDa. In some embodiments, the small molecule is less than about 800 daltons (Da), about 600 Da, about 500 Da, about 400 Da, about 300 Da, about 200 Da, or about 100 Da. In some embodiments, a small molecule is less than about 4000 g/mol, less than about 3000 g/mol, 2000 g/mol, less than about 1500 g/mol, less than about 1000 g/mol, less than about 800 g/mol, or less than about 500 g/mol. In some embodiments, small molecules are non-polymeric. Typically, small molecules are not proteins, polypeptides, polynucleotides, oligonucleotides, polysaccharides, glycoproteins, or proteoglycans, but include peptides of up to about 40 amino acids. A derivative of a small molecule refers to a molecule that shares the same structural core as the original small molecule, but which is prepared by a series of chemical reactions that vary and form a derivative of the original small molecule. As one example, a pro-drug of a small molecule is a derivative of that small molecule. An analog of a small molecule refers to a molecule that shares the same or similar structural core as the original small molecule, and which is synthesized by a similar or related route, or art-recognized variation, as the original small molecule.

In certain embodiments, compounds described herein have one or more chiral centers. As such, all stereoisomers are envisioned herein. In various embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer are utilized as the therapeutic compound described herein. In certain embodiments, compounds described herein contain one or more chiral centers. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

In various embodiments, pharmaceutically acceptable salts described herein include, by way of non-limiting example, a nitrate, chloride, bromide, phosphate, sulfate, acetate, hexafluorophosphate, citrate, gluconate, benzoate, propionate, butyrate, sulfosalicylate, maleate, laurate, malate, fumarate, succinate, tartrate, amsonate, pamoate, p toluenenesulfonate, mesylate and the like. Furthermore, pharmaceutically acceptable salts include, by way of non-limiting example, alkaline earth metal salts (e.g., calcium or magnesium), alkali metal salts (e.g., sodium-dependent or potassium), ammonium salts and the like.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, $^{35}$S or the like. In some embodiments, isotopically-labeled compounds are useful in drug and/or substrate tissue distribution studies. In some embodiments, substitution with heavier isotopes such as deuterium affords certain therapeutic advantages resulting from greater metabolic stability (for example, increased in vivo half-life or reduced dosage requirements). In some embodiments, substitution with positron emitting isotopes, such as $^{11}$C, $^{18}$F, $^{15}$O, and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The compounds described herein, and other related compounds having different substituents are synthesized using techniques and materials described herein and/or as described, for example. in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989). March, ADVANCED ORGANIC CHEMISTRY 6th Ed., (Wiley 2007); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3' Ed., (Wiley 1999), all of which are incorporated herein by reference for such disclosure. General methods for the preparation of compound as described herein are modified by the use of appropriate reagents and conditions, for the introduction of the various moieties found in the formula as provided herein.

Definitions

The terms "halo" and "halogen" as used herein to identify substituent moieties, represent fluorine, chlorine, bromine or iodine, preferably fluorine, chlorine or bromine.

The term "alkyl", alone or in combination, represents a cyclic, linear or branched chain saturated hydrocarbon group, which in the case of straight and branched chains, preferably has from one to four carbon atoms ($C_1$-$C_4$ alkyl) such as methyl, ethyl, n-propyl, isopropyl, cyclopropyl, n-butyl, isobutyl, sec-butyl, tert-butyl, n-pentyl, n-hexyl, and the like and in the case of a cyclic hydrocarbon preferably has from three to seven carbon atoms, such as cyclopropyl and cyclohexyl. The term "substituted alkyl" is intended to include an alkyl group substituted with a substituent group that is not H. An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, cyclopropyl, cyclobutyl, cyclopentyl, cyclohexyl, and the like. A "lower alkyl" is a $C_1$-$C_6$ alkyl.

The term "cycloalkyl" refers to a cyclic hydrocarbon chain, wherein the cycloalkyl is optionally substituted with one or more substituents as described herein. In one embodiment, monocyclic or polycyclic cycloalkyl groups may be saturated or unsaturated, but non-aromatic, and/or spiro and/or non-spiro, and/or bridged, and/or non-bridged, and/or fused bicyclic groups, wherein each of the atoms forming the ring (i.e. skeletal atoms) is a carbon atom. In various embodiments, cycloalkyls are saturated. or partially unsaturated. In some embodiments, cycloalkyls are fused with an aromatic ring. Cycloalkyl groups include groups having from 3 to 10 ring atoms: Monocyclic cycloalkyls include, but are not limited to, cyclopropyl, cyclobutyl, cyclopentyl, cyclohexyl, cycloheptyl, and cyclooctyl, cyclopentenyl, cyclohexenyl, cyclohexadienyl, cycloheptenyl. Bicyclic cycloalkyls include, but are not limited to tetrahydronaphthyl, indanyl, tetrahydropentalene, bicyclo[2.1.1]hexyl, bicyclo[2.2.1]heptyl, decalinyl, or the like. Polycyclic cycloalkyls include adamantane, norbornane or the like. The term cycloalkyl includes "unsaturated nonaromatic carbocyclyl" or "nonaromatic unsaturated carbocyclyl" groups both of which refer to a nonaromatic carbocycle, as defined herein that contains at least one carbon-carbon double bond or one carbon-carbon triple bond. In certain embodiments, the cycloalkyl has from 3 to 20 ($C_3$-$C_{20}$), from 3 to 15 ($C_3$-$C_1$), from 3 to 10 ($C_3$-$C_{10}$), or from 3 to 6 ($C_3$-$C_6$) carbon atoms. The term "haloalkyl" is one such substituted alkyl, substituted with one or more halo atoms, and preferably is a $C_1$ to $C_{10}$ alkyl substituted with one to five halo atoms. Examples of haloalkyl groups include, but are not limited to: difluoromethyl, dichloromethyl, trifluoromethyl, 2,2,2-trifluoroethyl, and pentafluroethyl.

The term "alkoxy", used alone or in combination, is an alkyl, preferably a $C_1$ to $C_4$ alkyl, covalently bonded to the parent molecule through an —O— linkage alone or in combination. Examples of alkoxy groups are methoxy, ethoxy, propoxy, isopropoxy, butoxy and t-butoxy. The term alkoxycarbonyl is, for example, t-butoxycarbonyl or BOC. An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl. The term "aryl" when used alone or in combination represents a substituted or unsubstituted phenyl, biphenyl, or naphthyl. Aryl may optionally be substituted with one or more substituents that are independently selected from hydroxy, carboxy, alkoxy, preferably a $C_1$ to $C_{10}$ alkoxy, an alkyl, preferably a $C_1$-$C_{10}$ alkyl, a haloalkyl, nitro, —NR$^2$R$^3$, —NHCO($C_1$-$C_{10}$ alkyl), —NHCO(benzyl), —NHCO(Phenyl), —SH, —S($C_1$-$C_4$ alkyl), —($C_1$-$C_4$ alkyl), —SO$_2$(NR$^2$R$^3$), —SO$_2$($C_1$-$C_{10}$ alkyl), —SO$_2$ (phenyl), or halo wherein R$^2$ and R$^3$ are as defined above.

The term "aryloxy" is one such aryl covalently bonded through an —O— linkage. The term "arylalkyl" can be considered a substituted alkyl and represents —(CH$_2$)$_m$aryl with m being an integer of generally 1 to 3, and preferably is benzyl. In contrast, the term alkylaryl can be considered a substituted aryl and may, for example, represent a moiety such as aryl($CH_2$)$_m$—$CH_3$ where n is an integer of generally 0 to 6.

The term "alkenyl" refers to a two to ten carbon, linear or branched hydrocarbon containing one or more carbon-carbon double bonds, preferably one or two double bonds, wherein the alkenyl group is optionally substituted with one or more substituents as described herein. Examples of alkenyl include ethylenyl, propylenyl, 1,3-butadienyl, and 1,3,5-hexatrienyl.

The term "alkynyl" refers to a linear or branched hydrocarbon, which contains one or more carbon-carbon triple bond(s), wherein the alkynyl is optionally substituted with one or more substituents as described herein. For example, $C_2$-$C_6$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon of 2 to 20 ($C_2$-$C_{20}$), 2 to 15 ($C_2$-$C_{15}$), 2 to 10 ($C_2$-$C_{10}$), or 2 to 6 ($C_2$-$C_6$) carbon atoms, or a branched monovalent hydrocarbon of 3 to 20 ($C_3$-$C_{20}$), 3 to 15 ($C_3$-$C_{15}$), 3 to 10 ($C_3$-$C_{10}$), or 3 to 6 ($C_3$-$C_6$) carbon atoms. Examples of alkynyl groups include, but are not limited to, ethynyl (—CCH), propynyl (including all isomeric forms, e.g., 1-propynyl (C⁻$CCH_3$) and propargyl ($CH_2CCH$)), and butynyl (including all isomeric forms, e.g., 1-butyn-1-yl and 2-butyn-1-yl).

The acyl moiety of an acylamino or acylaminoalkyl group is derived from an alkanoic acid containing a maximum of 10, preferably a maximum of 6, carbon atoms (e.g., acetyl, propionyl or butyryl) or from an aromatic carboxylic acid (e.g. benzoyl). An acyloxy is one such acyl bonded by an —O— linkage, for example, acetyloxy, $CH_3C$(=O)O—. An acylamino is, for example, $CH_3$(C=O)NH— (acetylamino). Likewise, an acylaminoalkyl is $CH_3$(C=O)NH($CH_2$)$_m$—.

The term "heteroatom" refers to any atom that is not carbon or hydrogen, such as the halogens, phosphorus, nitrogen, oxygen, or sulfur, and includes any oxidized form of nitrogen or sulfur, and any quaternized form of a basic nitrogen. A "heteroalkyl" group substitutes any one of the carbons of the alkyl group with a heteroatom having the appropriate number of hydrogen atoms attached (e.g., a CH, group to an NH group or an O group).

An "amide" is a chemical moiety with formula —C(O)NHR or —NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(O)OR, where R is selected from the group consisting of alkyl, cycloalkyl, aryl, heteroaryl and heteroalicyclic.

The term heterocycle or heterocyclic group, also denoted by "Het" or "heterocyclyl", can be a stable, saturated, partially unsaturated, or aromatic 5- or 6-membered heterocyclic group. The heterocyclic ring consists of carbon atoms and from one to three heteroatoms independently selected from the group consisting of nitrogen, oxygen, and sulfur. A heteroaryl group is heterocycle that is aromatic, such as pyridine. The heterocyclic group can be optionally substituted with one to four substituents independently selected from halogen, alkyl, aryl, hydroxy, alkoxy, haloalkyl, nitro, amino, acylamino, monoalkylamino, dialkylamino, alkylthio, alkylsulfinyl and alkylsulfonyl or, when the heterocyclyl group is an aromatic nitrogen-containing heterocyclic group, the nitrogen atom can carry an oxide group. Examples of such heterocyclic groups are imidazolyl, imidazolinyl, thiazolinyl, pyridyl, indolyl, furyl, pyrimidinyl, morpholinyl, pyridazinyl, pyrazinyl, triazinyl and triazolyl. Two or more heterocycles may be fused to form polyheterocycles such as, for example, azaindole or purine.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Examples of monocyclic heteroaryl groups include and are not limited to pyrrole, furan, thiophene, pyrazole, imidazole, isoxazole and are referred to as pyrrolyl, furanyl, thiophenyl, pyrazolyl, imidazolyl, and isoxazoly groups. The term heteroaryl refers to a cyclic aromatic compound containing 5 or 6 atoms with at least one heteroatom wherein the heteroaryl group derives from, for example, without limitation 1-H-pyrrole, pyrazole, imidazole, 1,2,4-triazole, 1,2,3-triazole, tetrazole, furan, thiophene, oxazole, isoxazole, isothiazole, thiazole, 1,2,5-oxadiazole, 1,2,3-oxadiazole, 1,3,4-thiadiazole, 1,2,5-thiadiazole, pyridine, pyridazine, pyrimidine, pyrazine, or 1,2,4-triazine. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. Two or more heteroaryl rings may be fused with another aryl or heteroaryl ring to form polyheteroaryls such as, for example, indole, benzofuran, benzoxazole, quinolone, isoquinoline, quinoxaline, quinazoline, cinnoline, or 1,8-naphtholine. The term "heteroaryl" as used herein also includes groups in which a heteroaromatic ring is fused to one or more aryl, cycloaliphatic, or heterocyclyl rings, where the radical or point of attachment is on the heteroaromatic ring. Nonlimiting examples of heteroaryl groups that contain two or more fused rings include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

The term "heterocycloalkyl" refers to a cyclic non-aromatic compound that is saturated or partially unsaturated and may contain one or more carbonyl (C=O) functional groups in the ring, wherein the heterocycloalkyl group derives from, for example, piperazine, piperidine, thiane, 1,3-dithiane, tetrahydropyran, 1,4-dioxane, 4-H-pyran, thiomorpholine, morpholine, aziridine, oxirane, thiirane, azetidine, 1,3-diazetidine, oxetane, thietane, azetidin-2-one, pyrrolidine, 3-pyrroline, pyrazolidine, imidazolidine, 2-pyrazoline, 2-imidazoline, tetrahydrofuran, 1,3-dioxolane, tetrahydrothiophene, 1,2-oxathiolane, 1,3-oxathiolane, sulfolane, 2-piperidinone, 2-pyrrolidone, caprolactam, succinimide, 1,3,5-trithiane, thiomorpholine dioxide, uracil, or thymine. A heterocycloalkyl group may be fused with another heterocycloalkyl or heteroaryl group to form a polyheterocycle, such as, for example, indoline or 2,3-dihydrobenzolfuran. The term "heterocyclo" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0] heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "tryptophan derivative" or "tryptophan analog" refers to the amino acid tryptophan that is substituted with one or more substituents other than hydrogen on one or more of its aromatic rings, and such that the substituents correspond to the definitions provided for A, B, C, D, A', B', C', and D', and/or a tryptophan that is substituted at the ring positions with C or N as defined for E, F, G, M, E', F', G', and M' above.

The term "substituted" means a substituent or function group or groups, such as those described for A, B, C, and D, are attached to carbon of the main hydrocarbon scaffold in place of hydrogen.

The term "leaving group" (LG) as used in the specification is readily understood by those skilled in the art. Generally, a leaving group is any group or atom that enhances the electrophilicity of the atom to which it is attached for easy displacement by a nucleophilic group or atom. Examples of preferred leaving groups are triflate ($-OSO_2CF_3$), mesylate, tosylate, imidate, chloride, bromide, and iodide.

Under certain circumstances it is at least desired and often required to protect the nitrogen (N) of intermediates during the synthesis of the compounds of formulae (I) with suitable "protecting groups" which are known. Introduction and removal of such nitrogen protecting groups are well-known to those skilled in the art.

In this regard, the term "—NH protective groups" and "protecting group" when used in a similar context, and as used in the specification and claims, refers to sub-class of amino protecting groups that are commonly employed to block or protect the —NH functionality while reacting other functional groups on the compound. The species of protecting group employed in carrying out the method of the present invention is not critical so long as the derivatized —NH group is stable to the condition(s) of subsequent reaction(s) and can be removed at the appropriate point without disrupting the remainder of the molecule. T. W. Greene and P. Wuts, Protective Groups in Organic Synthesis, Chapter 7, pages 385-394 and 397-403, provide a list of commonly employed protecting groups for indoles and maleimides. Preferred indole protecting groups are trimethylsilylethoxymethyl, benzyl, tosyl, carbamate, amide, alkyl or aryl sulfonamide, while maleimide protecting groups include alkoxy, benzyl, dialkoxybenzyl, benzyloxyalkyl or allyl. The related term "protected —NH" defines a group substituted with an —NH protecting group as defined.

In certain circumstances there may also be a need to protect hydroxy groups and amino groups during the synthetic processes of the present invention. Those skilled in the art are familiar with such "hydroxy protecting groups" and such "amino protecting groups." The term "hydroxy protecting group" refers to one of the ether or ester derivatives of the hydroxy group commonly employed to block or protect the hydroxy group while reactions are carried out on other functional groups on a compound. The species of hydroxy protecting group employed is not critical so long as the derivatized hydroxy group is stable to the condition of subsequent reaction(s) and can be removed at the appropriate point without disrupting the remainder of the molecule. Preferred hydroxy protecting groups are tertbutyldiphenylsilyloxy (TBDPS), tert-butyldimethylsilyloxy (TBDMS), triphenylmethyl (trityl), mono- or dimethoxytrityl, or an alkyl or aryl ester.

The term "amino protecting group" refers to substituents of an amino group commonly employed to block or protect the amino functionality while reacting other functional groups on the compound. The species of amino-protecting group employed in carrying out the method of the present invention is not critical so long as the derivatized amino group is stable to the condition(s) of subsequent reaction(s) and can be removed at the appropriate point without disrupting the remainder of the molecule. Preferred amino-protecting groups are t-butoxycarbonyl, phthalimide, a cyclic alkyl, and benzyloxycarbonyl.

The term "activated maleimide" as used in the specification refers to a 3,4-disubstituted maleimide (pyrrolyl-2,5-dione) or 2,3,4-trisubstituted maleimide, substituted with at least one leaving group that facilitates reaction with a reagent and especially with an optionally N-substituted organometallic-3-indole.

The term "indolylmaleimide" embraces a genus of compounds having as their root structure a 3-(indol-3-yl)-pyrrolyl-2,5-dione and includes the subgenus of "bisindolylmaleimides" having as their root structure a 3,4-(indol-3-yl)-pyrrolyl-2,5-dione, wherein the indol-3-yl moiety or moieties is/are optionally N-substituted, may optionally be substituted on the fused 6-membered aromatic ring of the indolyl moiety and may optionally be substituted at position 2 of the indol-3-yl moiety or moieties. Also included are those bisindolylmaleimides wherein the N-substituents of the indolyls are linked together through a bridging moiety as described for Q and R above in Formula (I) and for Formula (II). The prior art describes a range of such optionally substituted indolylmaleimides.

The term "indolocarbazole" refers to an alkaloid compound containing two indole rings derived from tryptophan and a fused maleimide or lactam functionality, and derivatives thereof. The most frequently isolated natural indolocarbazoles are indolo(2,3-a)carbazoles and the most common subgroup are the indolo(2,3-a)pyrrole(3,4-c)carbazoles.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "optionally substituted" or "substituted" means that the referenced group substituted with one or more additional group(s). In certain embodiments, the one or more additional group(s) are individually and independently selected from amide. ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkylamino, dialkyl-amino, amido.

The term "stable," as used herein, refers to compounds that are not substantially altered when subjected to conditions to allow for their production, detection, and, in certain embodiments, their recovery, purification, and use for one or more of the purposes disclosed herein.

As used herein, the term "solubilizing group" refers to a chemical moiety that promotes the solubility of a compound to which it is attached. Suitable solubilizing groups include, for example, saturated heterocyclic rings, such as morpholino, piperazinyl, and piperadinyl, and amino groups, such as dimethyl amino and methoxypropylamino.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen (H), deuterium ($^2$H), tritium ($^3$H), carbon-11 (C), carbon-12 ($^{12}$C) carbon-13 ($^{13}$C), carbon-14 ($^{14}$C), nitrogen-13 ($^{13}$N), nitrogen-14 ($^{14}$N) nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O) fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^3$S), sulfur-34 ($^{34}$S), sulfur-35 ($^{35}$S), sulfur-36 ($^6$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I) iodine-125 ($^{15}$I) iodine-127 ($^{127}$I) iodine-129 ($^{129}$I) and iodine-131 ($^{131}$I) In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen (H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O) oxygen-17 ($^{17}$O), oxygen-18 ($^{18}$O) fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S) chlorine-35 ($^{35}$Cl), chlorine-37 ($^{37}$C), bromine-79 ($^{79}$Br), bromine-81 ($^{81}$Br), and iodine-127 ($^{121}$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^3$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 (ml) iodine-125 ($^{125}$I), iodine-129 ($^{129}$I) and iodine-131 ($^{131}$I). It will be understood that, in a compound as provided herein, any hydrogen can be 2H, as example, or any carbon can be $^{13}$C, as example, or any nitrogen can be $^{15}$N, as example, and any oxygen can be $^{18}$O, as example, where feasible according to the judgment of one of skill in the art. In certain embodiments, an "isotopic variant" of a compound contains an unnatural proportion of deuterium.

Unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "naturally occurring" or "natural" or "native" when used in connection with naturally occurring biological materials such as nucleic acid molecules, amino acids, polypeptides, small molecule natural products, host cells, and the like, refers to materials that are found in or isolated directly from Nature and are not changed or manipulated by humans. Similarly, "non-naturally occurring" or "non-natural" or "unnatural" or "non-native" refers to a material that is not known to exist or not found in Nature or that has been structurally modified or synthesized by humans.

The term "semi-synthesis" refers to modifying a natural material synthetically to create a new variant, derivative, or analog of the original natural material. The terms "derivative" or "analog" refer to a structural variant of compound that derives from a natural or nan-natural material.

The terms "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question. In describing an optically active compound, the prefixes R and S are used to denote the absolute configuration of the molecule about its chiral center(s). The symbols (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The phrase "a stereoisomer, enantiomer, mixture of enantiomers, mixture of diastereomers, or isotopic variant thereof; or a pharmaceutically acceptable salt, solvate, hydrate, or prodrug thereof" has the same meaning as the phrase "a stereoisomer, enantiomer, mixture of enantiomers, mixture of diastereomers, or isotopic variant of the compound referenced therein; a pharmaceutically acceptable salt, solvate, hydrate, or prodrug of the compound referenced therein; or a pharmaceutically acceptable salt, solvate, hydrate, or prodrug of a stereoisomer, enantiomer, mixture of enantiomers, mixture of diastereomers, or isotopic variant of the compound referenced therein.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a disorder, disease, or condition.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The term "patient", as used herein, means an animal, preferably a mammal, and most preferably a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "IC$_{50}$" or "EC$_{50}$" refers an amount, concentration, or dosage of a compound that is required for 50% inhibition of a maximal response in an assay that measures such response. The term "CC$_{50}$" refers an amount, concentration, or dosage of a compound that results in 50% reduction of the viability of a host. In certain embodiments, the CC$_{50}$ of a compound is the amount, concentration, or dosage of the compound that is required to reduce the viability of cells treated with the compound by 50%, in comparison with cells untreated with the compound. The term "K" refers to the equilibrium dissociation constant for a ligand and a protein, which is measured to assess the binding strength that a small molecule ligand (such as a small molecule drug) has for a protein, such as a kinase. The dissociation constant, $K_d$, is commonly used to describe the affinity between a ligand and a protein; i.e., how tightly a ligand binds to a particular protein, and is the inverse of the association constant. Ligand-protein affinities are influenced by non-covalent intermolecular interactions between the two molecules such as hydrogen bonding, electrostatic interactions, hydrophobic and van der Waals forces. The analogous term "K$_i$" is the inhibitor constant or inhibition constant, which is the equilibrium dissociation constant for an enzyme inhibitor, and provides an indication of the potency of an inhibitor.

As used herein, the phrase "biologically active" refers to a characteristic of any substance that has activity in a biological system and/or organism. For instance, a substance that, when administered to an organism, has a biological effect on that organism is considered to be biologically active. In particular embodiments, where a protein or polypeptide is biologically active, a portion of that protein or polypeptide that shares at least one biological activity of the protein or polypeptide is typically referred to as a "biologically active" portion.

As used herein, the term "effective amount" is an amount, which when administered systemically, is sufficient to effect beneficial or desired results, such as beneficial or desired clinical results, or other desired effects that lead to an improvement of the disease condition. An effective amount is also an amount that produces a prophylactic effect. e.g., an amount that delays, reduces, or eliminates the appearance of a pathological or undesired condition associated with an autoimmune disease or cancer. An effective amount is optionally administered in one or more administrations. In terms of treatment, an "effective amount" of a composition described herein is an amount that is sufficient to palliate, alleviate, ameliorate, stabilize, reverse or slow the progression of an autoimmune disease or cancer.

An "effective amount" includes any PIM inhibitor used alone or in conjunction with one or more agents used to treat a disease or disorder. An "effective amount" of a therapeutic agent as described herein will be determined by a patient's attending physician or other medical care provider. Factors which influence what a therapeutically effective amount will be include, the absorption profile (e.g., its rate of uptake into the brain or other tissues) of the PIM3 inhibitor, time elapsed since the initiation of disease, and the age, physical condition, existence of other disease states, and nutritional status of an subject being treated. Additionally, other medication the patient is receiving, used in combination with a PIM3 inhibitor, will typically affect the determination of the therapeutically effective amount of the therapeutic agent to be administered.

As used herein, the term "inhibitor" refers to a molecule which is capable of inhibiting (including partially inhibiting or allosteric inhibition) one or more of the biological activities of a target molecule, e.g., a PIM kinase. Inhibitors, for example, act by reducing or suppressing the activity of a target molecule and/or reducing or suppressing signal transduction. In some embodiments, a PIM inhibitor described herein causes substantially complete inhibition of all three PIM kinases. In some embodiments, a PIM inhibitor described herein causes substantially complete inhibition of two PIM kinases, such as PIM1 and PIM3. In some embodiments, a PIM inhibitor described herein causes substantially complete inhibition of one PIM kinases, such as PIM3. In some embodiments, the phrase "partial inhibitor" refers to a molecule which can induce a partial response for example, by partially reducing or suppressing the activity of a target molecule and/or partially reducing or suppressing signal transduction. In some instances, a partial inhibitor mimics the spatial arrangement, electronic properties, or some other physicochemical and/or biological property of the inhibitor. In some instances, in the presence of elevated levels of an inhibitor, a partial inhibitor competes with the inhibitor for occupancy of the target molecule and provides a reduction in efficacy, relative to the inhibitor alone.

In some embodiments, a PIM inhibitor described herein is a partial inhibitor of PIM kinases. In some embodiments, a PIM inhibitor described herein is an allosteric modulator of PIM kinases. In some embodiments, a PIM inhibitor binds to the kinase domain of PIM kinases. In some embodiments, the PIM inhibitor described herein blocks the ATP binding site of PIM. In some embodiments, a PIM inhibitor is a "Type II" kinase inhibitor. In some embodiments a PIM inhibitor stabilizes the PIM kinases in their inactive conformation or state. In some embodiments, a PIM inhibitor stabilizes the "DFG-out" conformation of PIM kinases.

In some embodiments, PIM inhibitors reduce, abolish, and/or remove the binding between PIM and at least one of its natural binding partners (e.g. pro-apoptotic Bcl-2-associated death promoter protein (BAD), the ribosomal protein 4E-BP1, and transcription factor c-Myc). In some instances, binding between PIM and at least one of its natural partners is stronger in the absence of a PIM inhibitor (by e.g., 90%, 80%, 70%, 60%, 50%, 40%, 30° A or 20%) than in the presence of a PIM inhibitor. Alternatively or additionally, PIM inhibitors inhibit the phosphotransferase activity of PIM kinases, e.g., by binding directly to the catalytic site or by altering the conformation of PIM such that the catalytic site becomes inaccessible to substrates. In some embodiments, PIM inhibitors inhibit the ability of PIM kinases to phosphorylate at least one of its target substrates, e.g., transcription factors STAT3 and STAT5 (Signal Transducers and Activators of Transcription), c-Myc, FoxO1a, and FoxO3a, the cell cycle regulators $p^{27}$, Cdc25A, and Cdc25C, or itself. PIM inhibitors include inorganic and/or organic compounds.

In some embodiments, PIM inhibitors described herein decrease signal transduction induced by mitogenic growth factors such as interleukins and interferons binding to cytokine receptors. In some embodiments, PIM inhibitors described herein decrease phosphorylation of the pro-apoptotic BAD, thus enabling cell apoptosis. In some embodiments, PIM inhibitors described herein decrease cellular levels of transcription factor protein c-Myc. In some embodiments, PIM inhibitors described herein decrease cellular levels of peroxisome proliferator-activated receptor gamma coactivator 1α (PGC-1α), an enzyme capable of regulating glycolysis and mitochondrial biogenesis. In some embodiments, PIM inhibitors described herein decrease phosphorylation and activation of transcription factors STAT3, Myb, FoxO1a, and FoxO3a. In some embodiments, PIM inhibitors described herein increase glucose tolerance and insulin sensitivity. In some embodiments, PIM inhibitors described herein reduce levels of VEGF and angiogenesis by phosphorylating STAT3. In some embodiments, PIM inhibitors described herein decrease cell proliferation of pancreatic cancer cells. In some embodiments, PIM inhibitors described herein decrease cell proliferation of pancreatic cancer cells. In some embodiments, PIM inhibitors described herein decrease cell proliferation of gastric cancer cells. In some embodiments, PIM inhibitors described herein decrease cell proliferation of colorectal cancer cells. In some embodiments, PIM inhibitors described herein decrease cell proliferation of prostatic cancer cells. In some embodiments, PIM inhibitors described herein decrease cell proliferation of gallbladder cancer cells. In some embodiments, PIM inhibitors described herein decrease cell proliferation of nasopharyngeal cancer cells. In some embodiments, PIM inhibitors described herein decrease cell proliferation of hepatic cancer cells In some embodiments, a PIM inhibitor suitable for the methods described herein is a direct PIM inhibitor. In some embodiments, a PIM inhibitor suitable for the methods described herein is an indirect PIM inhibitor. In some embodiments, a PIM inhibitor suitable for the methods herein decreases PIM activity relative to a basal level of PIM activity by about 1.1 fold to about 1000 fold, e.g., to about 1.2 fold, 1.5 fold, 1.6 fold, 1.7 fold, 2.0 fold, 3.0 fold, 5.0 fold, 6.0 fold, 7.0 fold, 8.5 fold, 9.7 fold, 10 fold, 12 fold, 14 fold, 15 fold, 20 fold, 30 fold, 40 fold, 50 fold, 60 fold, 70 fold. 80 fold, 90 fold, 95 fold, 100 fold, 200 fold, 300 fold, 400 fold, 500 fold, 600 fold, 700 fold, 800 fold, 900 fold, 1000 fold, or by any other amount from about 1.1 fold to about 1000 fold relative to basal PIM3 activity. In some embodiments, the PIM inhibitor is a reversible PIM inhibitor. In other embodiments, the PIM inhibitor is an irreversible PIM inhibitor. Direct PIM inhibitors are optionally used for the manufacture of a medicament for treating a malignant or cancerous disease.

In some embodiments, a PIM inhibitor used for the methods described herein has an in vitro $IC_{50}$, defined as inhibitory concentration where 50% of the activity of one or more PIM kinases is remaining after contacting a PIM inhibitor with PIM kinase, or dissociation constant ($K_d$), or inhibitory constant (K) of less than 100 μM (e.g., less than 10 μM, less than 5 μM, less than 4 M, less than 3 M, less than 1 μM, less than 0.8 M, less than 0.6 μM, less than 0.5 M, less than 0.4 μM, less than 0.3 μM, less than less than 0.2 μM.

less than 0.1 M, less than 0.08 µM, less than 0.06 M, less than 0.05 µM, less than 0.04 µM, less than 0.03 µM, less than less than 0.02 µM, less than 0.01 M, less than 0.0099 µM, less than 0.0098 µM, less than 0.0097 µM, less than 0.0096 µM, less than 0.0095 µM, less than 0.0094 µM, less than 0.0093 M, less than 0.00092 µM, less than 0.0090 µM, less than 0.0010 µM, or less than 0.00010 µM).

As used herein, "expression" of a nucleic acid sequence refers to one or more of the following events: (1) production of an RNA template from a DNA sequence (e.g., by transcription of DNA into messenger RNA); (2) processing of an RNA transcript (e.g., by splicing, editing. 5' cap formation, and/or 3' end formation); (3) translation of an RNA into a polypeptide or protein; (4) post-translational modification of a polypeptide or protein.

As used herein the term "PIM polypeptide" or "PIM protein" or "PIM" or "PIM kinase" refers to a protein that belongs in the serine/threonine family of human kinases. A representative example of PIM1 amino acid sequences includes, but is not limited to, human PIM (GenBank Accession Number P11309). Human PIM1 also has two truncated isoforms of 34 kDa and 44 kDa that have been identified and PIM1 homologues exist throughout the animal kingdom. A representative example of PIM2 amino acid sequences includes, but is not limited to, human PIM2 (GenBank Accession Number Q9P1W9). Human PIM2 also has three truncated isoforms of 34 kDa, 37 kDa, and 40 kDa that have been identified and PIM2 homologues exist throughout the animal kingdom. PIM3 amino acid sequences include, but are not limited to, human PIM3 (GenBank Accession Number Q86V86). Human PIM3 also has numerous truncated isoforms that have been identified and PIM3 homologues exist throughout the animal kingdom.

In some embodiments, a PIM1 polypeptide comprises an amino acid sequence that is at least 60% to 100% identical, e.g., at least 75%, 80%, 85%, 86%, 87%, 88%, 90%, 91%, 92%, 94%, 95%, 96%, 97%, 98%, or any other percent from about 70% to about 100% identical to sequences of GenBank Accession Number P11309. In some embodiments, a PIM2 polypeptide comprises an amino acid sequence that is at least 60% to 100% identical, e.g., at least 75%, 80%, 85%, 86%, 87%, 88%, 90%, 91%, 92%, 94%, 95%, 96%, 97%, 98%, or any other percent from about 70% to about 100% identical to sequences of GenBank Accession Number Q9P1W9. In some embodiments, a PIM3 polypeptide comprises an amino acid sequence that is at least 60% to 100% identical, e.g., at least 75%, 80%, 85%, 86%, 87%, 88%, 90%, 91%, 92%, 94%, 95%, 96%, 97%, 98%, or any other percent from about 70% to about 100% identical to sequences of GenBank Accession Number Q86V86.

A representative example of human PIM1 genes encoding PIM1 proteins include, but are not limited to, human PIM1 (GenBank Accession Number 5292). In some embodiments, a human PIM1 gene comprises a nucleotide sequence that is at least 70% to 100% identical, e.g., at least 75%, 80%, 85%. 86%, 87%, 88%, 90%, 91%, 92%, 94%, 95%, 96%, 97%, 98%, or any other percent from about 70% to about 100% identical to sequences of GenBank Accession Number 5292. A representative example of human PIM2 genes encoding PIM2 proteins include, but are not limited to, human PIM2 (GenBank Accession Number 11040). In some embodiments, a human PIM2 gene comprises a nucleotide sequence that is at least 70% to 100% identical, e.g., at least 75%, 80%, 85%. 86%, 87%, 88%, 90%, 91%, 92%, 94%, 95%, 96%, 97%, 98%, or any other percent from about 70% to about 100% identical to sequences of GenBank Accession Number 11040. A representative example of human PIM3 genes encoding PIM3 proteins include, but are not limited to, human PIM3 (GenBank Accession Number 415116). In some embodiments, a human PIM3 gene comprises a nucleotide sequence that is at least 70% to 100% identical, e.g., at least 75%, 80%, 85%. 86%, 87%, 88%, 90%, 91%, 92%, 94%, 95%, 96%, 97%, 98%, or any other percent from about 70% to about 100% identical to sequences of GenBank Accession Number 415116.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In one embodiment the two sequences are the same length.

To determine percent homology between two sequences, the algorithm of Karlin, S. and Altschul, S. F., Proc. Natl. Acad. Sci. USA, 1990, 87:2264-2268, modified as in Karlin, S. and Altschul S. F., Proc. Natl. Acad. Sci. USA, 1993, 90:5873-5877 is used. Such an algorithm is incorporated into the NBLAST and BLAST programs of Altschul, S. F., et al., J. Mol. Biol., 1990, 215, 403-410. BLAST nucleotide searches are performed with the NBLAST program, score=100; wordlength=12 to obtain nucleotide sequences homologous to a nucleic acid molecules described or disclose herein. BLAST protein searches are performed with the BLAST program, score=50, wordlength=3. To obtain gapped alignments for comparison purposes, Gapped BLAST is utilized as described in Altschul, S. F., et al. Nucleic Acids Res., 1997, 25, 3389-3402. When utilizing BLAST and Gapped BLAST programs, the default parameters of the respective programs (e.g., BLAST and NBLAST) are used. See the website of the National Center for Biotechnology Information for further details (www.ncbi.nlm.nih.gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein PIM3 inhibitor described herein. In other embodiments, the altered amino acid sequence is at least 75% identical, e.g., 77%, 80%, 82%, 85%, 88%, 90%, 92%, 95%, 97%, 98%, 99%, or 100% identical to the amino acid sequence of any protein PIM3 inhibitor described herein. Such sequence-variant proteins are suitable for the methods described herein as long as the altered amino acid sequence retains sufficient biological activity to be functional in the compositions and methods described herein. Where amino acid substitutions are made, the substitutions should be conservative amino acid substitutions. Among the 20 common proteinogenic amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff, S., et al., Proc. Natl. Acad. Sci. USA, 1992, 89, 10915-10919). Accordingly, the BLOSUM62 substitution frequencies are used to define conservative amino acid substitutions that may be introduced into the amino acid sequences described or described herein. Although it is possible to design amino acid substitutions based solely upon chemical properties (as discussed above), the language "conservative amino acid substitution" preferably refers to a substitution represented by a BLOSUM62 value of greater than 1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

As used herein, the term "PIM activity," unless otherwise specified, includes, but is not limited to, at least one of PIM kinase protein-protein interactions, PIM phosphotransferase activity (intermolecular or intermolecular), translocation, etc of one or more PIM isoforms. As used herein, a "PIM inhibitor" refers to any molecule, compound, or composition that directly or indirectly decreases the PIM activity. In some embodiments, PIM inhibitors inhibit, decrease, and/or abolish the level of a PIM mRNA and/or protein or the half-life of PIM mRNA and/or protein, such inhibitors are referred to as "clearance agents". In some embodiments, a PIM inhibitor is a PIM antagonist that inhibits, decreases, and/or abolishes an activity of PIM. In some embodiments, a PIM inhibitor also disrupts, inhibits, or abolishes the interaction between PIM and its natural binding partners (e.g., a substrate for PIM3 kinase, for BAD, or for c-Myc) or a protein that is a binding partner of PIM in a pathological condition, as measured using standard methods.

In some embodiments, PIM3 inhibitors reduce, abolish, and/or remove the binding between PIM and at least one of its natural binding partners (e.g., BAD, AMPK, STAT3, c-Myc, Myb, FoxO1a, and FoxO3a, p21, p27, PGC-1α, eIF4B, Cdc25A, Cdc25C, or translationally controlled tumor protein TCTP/TPT1). In some instances, binding between PIM and at least one of its natural binding partners is stronger in the absence of a PIM inhibitor (by e.g., 90%, 80%, 70%, 60%, 50%, 40%, 30% or 20%) than in the presence of a PIM inhibitor. In some embodiments, PIM inhibitors prevent, reduce, or abolish binding between PIM and a protein that abnormally accumulates or aggregates in cells or tissue in a disease state. In some instances, binding between PIM and at least one of the proteins that aggregates or accumulates in a cell or tissue is stronger in the absence of a PIM inhibitor (by e.g., 90%, 80%, 70%, 60%, 50%, 40%, 30% or 20%) than in the presence of an inhibitor. An "individual" or an "individual," as used herein, is a mammal. In some embodiments, an individual is an animal, for example, a rat, a mouse, a dog or a monkey. In some embodiments, an individual is a human patient. In some embodiments an "individual" or an "individual" is a human. In some embodiments, an individual suffers from cancer or is suspected to be suffering from cancer or is genetically pre-disposed to cancer. In some embodiments, a pharmacological composition comprising a PIM inhibitor is "administered peripherally" or "peripherally administered." As used herein, these terms refer to any form of administration of an agent, e.g., a therapeutic agent, to an individual that is not direct administration to the central nervous system, i.e., that brings the agent in contact with the non-brain side of the blood-brain barrier. "Peripheral administration," as used herein, includes intravenous, intra-arterial, intramuscular, intraperitoneal, transdermal, by inhalation, transbuccal, intranasal, rectal, oral, parenteral, sublingual, or transnasal. In some embodiments, a PIM3 inhibitor is administered by an intracerebral route.

The terms "polypeptide," and "protein" are used interchangeably herein to refer to a polymer of amino acid residues. That is, a description directed to a polypeptide applies equally to a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid. glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer, M. A., et al., Nucleic Acid Res., 1991, 19, 5081-1585; Ohtsuka, E. et al., J. Biol. Chem., 1985, 260, 2605-2608; and Rossolini, G. M., et al., Mol. Cell. Probes, 1994, 8, 91-98).

The terms "isolated" and "purified" refer to a material that is substantially or essentially removed from or concentrated in its natural environment. For example, an isolated nucleic acid is one that is separated from the nucleic acids that normally flank it or other nucleic acids or components (proteins, lipids, etc.) in a sample. In another example, a polypeptide is purified if it is substantially removed from or concentrated in its natural environment. Methods for purification and isolation of nucleic acids and proteins are documented methodologies.

The term "antibody" describes an immunoglobulin whether natural or partly or wholly synthetically produced. The term also covers any polypeptide or protein having a binding domain which is, or is homologous to, an antigen binding domain. CDR grafted antibodies are also contemplated by this term. The term antibody as used herein will also be understood to mean one or more fragments of an antibody that retain the ability to specifically bind to an antigen, (See generally: Holliger, P. et al., Nature Biotech. 2005, 23 (9), 1126-1129). Non-limiting examples of such antibodies include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward, E. S., et al., Nature, 1989, 341, 544-546), which consists of a VH domain: and (vi) an isolated complementarity determining region (CDR). Furthermore, although the two domains of the Fv fragment, VL and VH, are coded for by separate genes, they are optionally joined, using recombinant methods, by a synthetic linker that enables them to be made as a single protein chain in which the VL and VH regions pair to form monovalent molecules (known as single chain Fv (scFv); see e.g., Bird, R. E., et al., Science 1988, 242, 423-426; Huston, J. S., et al., Proc. Natl. Acad. Sci. USA, 1988, 85, 5879-5883; and Osbourn, J. K., et al., Nat. Biotechnol. 1998, 16, 778-781). Such single chain antibodies are also intended to be encompassed within the term antibody. Any VH and VL sequences of specific scFv is optionally linked to human immunoglobulin constant region cDNA or genomic sequences, in order to generate expression vectors encoding complete IgG molecules or other isotypes. VH and VL are also optionally used in the generation of Fab, Fv or other fragments of immunoglobulins using either protein chemistry or recombinant DNA technology. Other forms of single chain antibodies, such as diabodies are also encompassed. "F(aW)," and "Fab" moieties are optionally produced by treating immunoglobulin (monoclonal antibody) with a protease such as pepsin and papain, and includes an antibody fragment generated by digesting immuno-globulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CHy1 (y1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are documented. "Fv" is the minimum antibody fragment which contains a complete antigen-recognition and antigen binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site. "Single-chain Fv" or "sFv" antibody fragments comprise a VH, a VL, or both a VH and VL domain of an antibody, wherein both domains are present in a single polypeptide chain. In some embodiments, the Fv polypeptide further comprises a polypeptide linker between the VH and VL domains which enables the sFv to form the desired structure for antigen binding. For a review of sFv see, e.g., Pluckthun in "The Pharmacology of Monoclonal Antibodies," Vol. 113, Rosenburg and Moore eds. Springer-Verlag, New York, pp. 269-315 (1994).

A "chimeric" antibody includes an antibody derived from a combination of different mammals. The mammal is, for example, a rabbit, a mouse, a rat, a goat, or a human. The combination of different mammals includes combinations of fragments from human and mouse sources. In some embodiments, an antibody described or described herein is a monoclonal antibody (MAb), typically a chimeric human-mouse antibody derived by humanization of a mouse monoclonal antibody. Such antibodies are obtained from, e.g., transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. In some embodiments, the transgenic mice synthesize human antibodies specific for human antigens, and the mice are used to produce human antibody-secreting hybridomas.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the term "modulating" or "modulate" refers to an effect of altering a biological activity (i.e. increasing or decreasing the activity), especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

In the context of the use, testing, or screening of compounds that are or may be modulators, the term "contacting" means that the compound(s) are caused to be in sufficient proximity to a particular molecule, complex, cell, tissue, in an organism, or other specified material that potential binding interactions and/or chemical reaction between the compound and other specified material can occur.

Kinase Activity Assay.

A number of different assays for kinase activity can be utilized for assaying for active modulators and/or determining specificity of a modulator for a particular kinase or group of kinases. In addition to the assays mentioned in the Examples below, one of ordinary skill in the art will know of other assays that can be utilized and can modify an assay for a particular application. For example, numerous papers concerning kinases describe assays that can be used. Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

As used herein, the term "biopharmaceutical properties" refers to the pharmacokinetic action of a compound or complex of the present invention, including the dissolution, absorption and distribution of the compound on administration to a subject. As such, certain solid forms of compounds of the invention, such as amorphous complexes of compounds of the invention, are intended to provide improved dissolution and absorption of the active compound, which is typically reflected in improved Cmax, (the maximum achieved concentration in the plasma after administration of the drug) and improved AUC (i.e. area under the curve of drug plasma concentration vs. time after administration of the drug).

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

Alternative Compound Forms or Derivatives

Compounds contemplated herein are described with reference to both generic formulae and specific compounds. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an NH group of the compound has undergone acylation, such as the 7-position of the pyrrolo[2,3-d] pyrimidine ring, the 1-position of the 1H-pyrrolo[2,3-b] pyridine ring, or the nitrogen of the sulfonamide group of compounds as described herein, where cleavage of the acyl group provides the free NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in The Practice of Medicinal Chemistry, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug, and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Pat.

No. 7,270,808, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite. Metabolites of a compound may be identified using routine techniques known in the art, and their activities determined using tests such as those described herein. See, e.g., Bertolini et al., 1997, J. Med. Chem., 40:2011-2016; Shan et al., 1997, J Pharm Sci 86(7):756-757; Bagshawe, 1995, Drug Dev. Res., 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae. Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent toluenesulfonate carbons of a double bond. All such single stereoisomers, racemates and mixtures thereof are intended to be within the scope of the present invention. Unless specified to the contrary, all such stereoisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein can be in the form of pharmaceutically acceptable salts, or can be formulated as pharmaceutically acceptable salts.

Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in so physical properties include lowering the melting point to facilitate transmucosal administration and increasing the solubility to facilitate administering higher concentrations of the drug. A compound of the invention may possess a sufficiently acidic, a sufficiently basic, or both functional groups, acid/base and accordingly can react with any of a number of inorganic or organic bases, and inorganic and organic acids, to form a pharmaceutically acceptable salt.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, pharmaceutically acceptable salts are described in S. M. Berge et al., J. Pharmaceutical Sciences, 1977, 66, 1-19, which is incorporated herein by reference.

Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and quaternary ammonium, $N(C_1-C_4\ alky)_4$, salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl sulfonate and aryl sulfonate.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by addition, i.e. 4 free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, butylamine, piperazine, meglubesylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, stearowet, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechano-chemical methods such as roller compaction, or microwave irradiation of the parent compound mixed with the acid or base. Such methods may also include addition of ionic and/or succinate), non-ionic polymer systems, including, but not limited to, hydroxypropyl methyl cellulose acetate succinate (HPMCAS) and methacrylic acid copolymer (e.g. EUDRAGIT® L10055), that further stabilize the amorphous nature of the complex. Such amorphous complexes provide several advantages. For example, lowering the melting temperature relative to the free base facilitiates additional processing, such as hot melt extrusion, further improves the biopharmaceutical properties of the compound. Also, the amorphous complex is readily friable, which provides improved compression for loading of the solid into capsule or tablet form. Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

Pharmaceutically Acceptable Compositions

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st ed.; Lippincott Williams & Wilkins. Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, $3^{rd}$ ed., Ash and Ash Eds.; Gower Publishing Company: 2007; Pharmaceutical Preformulation and Formulation, 2nd ed.; Gibson Ed.; CRC Press LLC: Boca Raton, Fla., 2009. The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a target protein kinase, particularly PIM3, or a mutant thereof, in a biological sample or in a patient. In certain embodiments, the amount of compound in compositions of this invention is such that is effective to measurably inhibit PIM3, or a mutant thereof, in a biological sample or in a patient. In certain embodiments, a composition of this invention is formulated for administration to a patient in need of such composition. In some embodiments, a composition of this invention is formulated for oral administration to a patient.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of PIM3 or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed or synthetic mono- or di-glycerides. Fatty acids, such as oleic acid and its glyceride derivatives are useful in the preparation of injectables, as are natural pharmaceutically-acceptable oils, such as olive oil or castor oil, especially in their poly-oxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets aqueous suspensions or solutions. In the case of tablets for oral use, carriers commonly used include lactose and cornstarch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be in a rectal suppository formulation (see above) or in suitable enema formulation. Topically-transdermal patches may also be used. For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum. Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions. It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

As used herein, the term "inhibitor" is defined as a compound that binds to and/or inhibits a target protein kinase with measurable affinity. In certain embodiments, an inhibitor has an $IC_{50}$ and/or binding constant of less than about 50 M, less than about 1 µM, less than about 500 nM, less than about 100 nM, less than about 10 nM, or less than about 1 nM.

A compound of the present invention may be tethered to a detectable moiety. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev, V. V, et al., Angew. Chem. Int. Ed. Engl. 2002, 41, 2596-2599 and Sun, X.-L., et al., Bioconjugate Chem., 2006, 17, 52-57.

As used herein, the term "detectable moiety" is used interchangeably with the term "label" and relates to a moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of non-radiative fluorescent resonance energy transfer (FRET), and the second group produces the detected signal. The terms "fluorescent label", "fluorescent dye", and "fluorophore" as used herein refer to moieties that absorb light energy at a defined excitation wavelength and emission of light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxy-40 coumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-methoxytetrafluorobenzyl)-phenyloxy]-3-methylglyceronyl]isonipecotic Acid, 4'-[2,3,5,6-Tetrafluoro-4-(pentafluoro-phenoxyl)]methyl acetophenone, and their derivatives. The synthesis and utility of these mass-tags is described in U.S. Pat. Nos. 4,650,750; 4,709, 016; 5,360,819; 5,516,931; 5,602,273; 5,604,104; 5,610, 020; and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a protein kinase activity between a sample comprising a compound of the present invention, or composition thereof, and protein, and an equivalent sample comprising the protein kinase, in the absence of said compound, or composition thereof.

As used herein, the terms "PIM-mediated," disorders or conditions as used herein means any disease or other deleterious condition in which PIM kinase, or a mutant thereof, are known to play a role. Accordingly, another embodiment of the present invention relates to treating or lessening the severity of one or more diseases in which one or more of the PIM kinases or a mutant thereof, are known to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more disorders selected from the various forms of cancer. In some embodiments, the cancer is associated with a solid tumor. In certain embodiments, the cancer is breast cancer, pancreatic cancer, hepatocellular cancer, prostate cancer, gastric cancer, glioblastoma, lung cancer, cancer of the head and neck, colorectal cancer, bladder cancer, or non-small cell lung cancer. In some instances, the present invention provides a method for treating or lessening the severity of one or more disorders selected from squamous cell carcinoma, salivary gland carcinoma, ovarian carcinoma, or pancreatic cancer. In other embodiments, the cancer is associated with a soluble tumor, such as a leukemia, lymphoma or myeloma.

In some embodiments, the present invention provides a method for treating or lessening the severity of one or more immunological or hypersensitivity disorders, such as asthma, allergy, transplant rejection, graft versus host disease, and autoimmune diseases such as rheumatoid arthritis, amyotrophic lateral sclerosis, and multiple sclerosis, as well as in solid and hematologic malignancies such as leukemias, lymphomas, and myelomas, wherein said method comprises administering to a patient in need thereof a composition according to the present invention. Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated." For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodolphyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and GLEEVEC™ among others. In other embodiments, a compound of the present invention is administered in combination with a biologic agent, such as AVASTIN™ or VECTIBIX™. In certain embodiments, compounds of the present invention, or a pharmaceutically acceptable composition thereof, are administered in combination with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cladribine, Clofarabine, Cyclophosphamide, Cytarabine, Dactinomycin, Darbepoetin alfa, Daunorubicin, Denileukin, Dexrazoxane, Docetaxel, Doxorubicil (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard Valrubicin, Vinblastine, Vincristine, Vinorelbine, Zoledronate, or Zoledronic acid.

Other examples of agents that may also be combined with the inhibitors of this invention include, without limitation: treatments for Alzheimer's disease such as ARICEPT® and EXCELON®; treatments for Parkinson's Disease such as L-DOPA/carbidopa, entacapone, ropinrole, pramipexole, bromocriptine, pergolide, trihexephendyl, and amantadine; active agents for treating Multiple Sclerosis (MS) such as beta interferon (e.g., AVONEX® and REBIF®), COPAXONE®, and mitoxantrone; treatments for asthma such as albuterol and SINGULAIR®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or with an siRNA therapeutic.

Those additional agents may be administered separately from an inventive compound containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of Formula (I) or (II), an additional therapeutic agent, and a pharmaceutically acceptable carrier, adjuvant, or vehicle. The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 mg/kg body weight/day of the additional therapeutic agent can be administered. The amount of additional therapeutic agent present in the compositions of this invention will be no more than the amount that would normally be administered in a composition comprising that therapeutic agent as the only agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters.

Drug resistance is emerging as a significant challenge for targeted therapies. For example, drug resistance has been reported for GLEEVEC™ and IRESSA™, as well as several other kinase inhibitors in development. Drug resistance, for example, has been reported for inhibitors cKit and EGFR kinases used for cancer treatment. It has been reported that irreversible inhibitors may be effective against drug resistant forms of protein kinases (See: Kwak, E. L., et al., Proc. Nat. Acad. Sci. USA, 2005, 102, 7665-7670). Compounds of the present invention may be effective inhibitors of drug resistant forms of protein kinases.

As used herein, the term "clinical drug resistance" refers to the loss of susceptibility of a drug target to drug treatment as a consequence of mutations in the drug target. As used herein, the term "resistance" refers to changes in the wild-type nucleic acid sequence coding a target protein or its promoter, and/or the protein sequence of the target, which changes decrease or abolish the inhibitory effect of the inhibitor on the target protein. For example, PIM3 inhibitor resistance also may involve expression of another protein kinase, such as PIM1, which compensates for the loss of PIM3 kinase activity. Examples of kinases that are inhibited by the compounds and compositions described herein and against which the methods described herein are useful against PIM kinases, or mutants thereof.

The activity of a compound utilized in this invention as an inhibitor of a target kinase, in particular the PIM kinases and preferably PIM3, or a mutant thereof, may be assayed in vitro, in vivo or in a cell line. In vitro assays include more assays that determine inhibition of either the phosphorylation activity and/or the subsequent functional consequences, or ATPase activity of activated target kinase, or a mutant thereof. Alternate in vitro assays quantitate the ability of the inhibitor to bind to a target kinase, e.g., PIM3. Inhibitor binding may be measured by radiolabelling the inhibitor prior to binding, isolating the inhibitor/target kinase complex and determining the amount of radiolabel bound. Alternatively, inhibitor binding may be determined by running a competition experiment where new inhibitors are incubated with target kinase bound to known radioligands. Detailed conditions for assaying a compound utilized in this invention as an inhibitor of certain kinases, or a mutant thereof, are set forth in the Examples below.

Protein kinases are a class of enzymes that catalyze the transfer of a phosphate group from ATP or GTP to an acceptor amino acid residue (e.g., tyrosine, serine, and threonine) residue located on a protein substrate. Receptor kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of target PIM kinases and are useful for treating one or more disorders associated with activity of PIM kinase. Thus, in certain embodiments, the present invention provides a method for treating PIM-mediated disorders comprising the step of administering to a patient in need thereof a compound of the present invention, or pharmaceutically acceptable composition thereof.

In some embodiments, compounds of this invention are optionally administered in combination with a PIM inhibitor clearance agent. In some embodiments, compounds of this invention are optionally administered in combination with a compound that directly or indirectly decreases the activation or activity of the upstream effectors of PIM. For example, in some embodiments a compound that inhibits the activity of Janus kinases (JAK1-3) is used in combination, thereby reducing the activation of PIM kinase. For example, use of the JAK inhibitor tofacitinib could reduce phosphorylation and production of active STAT3 and STAT5 and thus decrease the expression, activity or activation of PIM3 (See: Hodge, J. A., et al., Clin. Exp. Rheumatol., 2016; 34, 318-328). In some embodiments, PIM3 activation is also decreased by small molecules that bind directly to STAT3 and STAT5. In some embodiments, PIM3 inhibitors are used in combination with agents that bind directly to BAD or prevent PIM kinases from phosphorylating serine residues in these downstream effectors (e.g., BAD Ser112).

In some embodiments, compounds of the invention are optionally administered in combination with a compound that decreases the level of PIM kinases, including a peptide, polypeptide, or small molecule that inhibits dephosphorylation of a downstream target of PIM, such that phosphorylation of the downstream target remains at a level that leads to downregulation of PIM levels. In some embodiments, PIM activity is reduced or inhibited via activation and/or inhibition of an upstream regulator and/or downstream target of PIM. In some embodiments, the protein expression of a PIM is downregulated. In some embodiments, the amount of PIM in a cell is decreased. In some embodiments a compound that decreases PIM3 protein levels in cells also decreases the activity of PIM kinases in the cells. In some embodiments a compound that decreases PIM protein levels does not decrease PIM activity in cells. In some embodiments a compound that increases PIM activity in cells decreases PIM protein levels in the cells.

Any combination of a PIM inhibitor and second therapeutic agent is compatible with any method described herein. The PIM inhibitor compositions described herein are also optionally used in combination with other therapeutic reagents that are selected for their therapeutic value for the condition to be treated. In general, the compositions described herein and, in embodiments where combinational therapy is employed, other agents do not have to be administered in the same pharmaceutical composition, and, because of different physical and chemical characteristics, are optionally administered by different routes. The initial administration is generally made according to established protocols, and then, based upon the observed effects, the dosage, modes of administration and times of administration subsequently modified.

In certain instances, it is appropriate to administer a PIM inhibitor composition described herein in combination with another therapeutic agent. By way of example only, if one of the side effects experienced by a patient upon receiving a PIM inhibitor composition described herein is nausea, then it is appropriate to administer an anti-nausea agent in combination with the initial therapeutic agent. Or, by way of example only, the therapeutic effectiveness of a PIM inhibitor is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering a PIM inhibitor with another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically-effective dosages vary when the drugs are used in treatment combinations. Suitable methods for experimentally determining therapeutically-effective dosages of drugs and other agents include, e.g., the use of metronomic dosing, i.e., providing more frequent, lower doses in order to minimize toxic side effects. Combination treatment further includes periodic treatments that start and stop at various times to assist with the clinical management of the patient.

In any case, the multiple therapeutic agents (one of which is a PIM inhibitor described herein) is administered in any order, or even simultaneously. If simultaneously, the multiple therapeutic agents are optionally provided in a single, unified form, or in multiple forms (by way of example only, either as a single pill or as two separate pills). In some embodiments, one of the therapeutic agents is given in multiple doses, or both are given as multiple doses. If not simultaneous, the timing between the multiple doses optionally varies from more than zero weeks to less than four weeks. In addition, the combination methods, compositions and formulations are not to be limited to the use of only two agents. The use of multiple therapeutic combinations is also envisioned.

The pharmaceutical agents which make up the combination therapy disclosed herein are optionally a combined dosage form or in separate dosage forms intended for substantially simultaneous administration. The pharmaceutical agents that make up the combination therapy are optionally also be administered sequentially, with either therapeutic compound being administered by a regimen calling for two step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and pharmacokinetic profile of the pharmaceutical agent. Circadian variation of the target molecule concentration is optionally used to determine the optimal dose interval.

In addition, a PIM inhibitor is optionally used in combination with procedures that provide additional or synergistic benefit to the patient. By way of example only, patients are expected to find therapeutic and/or prophylactic benefit in the methods described herein, wherein pharmaceutical composition of a PIM inhibitor and/or combinations with other therapeutics are combined with genetic testing to determine whether that individual is a carrier of a mutant gene that is correlated with certain diseases or conditions.

A PIM inhibitor and additional therapies are optionally administered before, during or after the occurrence of a disease or condition, and the timing of administering the composition containing a PIM inhibitor varies in some embodiments. Thus, for example, the PIM inhibitor is used as a prophylactic and administered continuously to individual with a propensity to develop conditions or diseases in order to prevent the occurrence of a disease or condition.

PIM inhibitors and compositions are optionally administered to an individual during or as soon as possible after the onset of the symptoms. The administration of the compounds are optionally initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration is optionally via any route practical, such as, for example, an intravenous injection, a bolus injection, infusion over 5 minutes to about 5 hours, a pill, a capsule, transdermal patch, buccal delivery, and the like, or combination thereof a PIM inhibitor is optionally administered as soon as is practicable after the onset of a disease or condition is detected or suspected, and for a length of time necessary for the treatment of the disease, such as, for example, from about 1 month to about 3 months. For chronic non-life-threatening diseases, treatment duration may be extended for years. The length of treatment optionally varies for each disease and each individual, and the length is then determined using the known criteria. For example, the PIM inhibitor or a formulation containing the PIM inhibitor can be administered for at least 2 weeks, preferably about 1 month to about 5 years, and more preferably from about 1 month to about 2 years for treatment of cancer.

In some embodiments, the particular choice of compounds depends upon the diagnosis of the attending physicians and their judgment of the condition of an individual and the appropriate treatment protocol. The compounds are optionally administered concurrently (e.g., simultaneously, essentially simultaneously or within the same treatment protocol) or sequentially, depending upon the nature of the disease, disorder, or condition, the condition of an individual, and the actual choice of compounds used. In certain instances, the determination of the order of administration, and the number of repetitions of administration of each therapeutic agent during a treatment protocol, is based on an evaluation of the disease being treated and the condition of an individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents. The compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing. e.g., from more than zero weeks to less than four weeks. In some embodiments, the additional therapeutic agent is utilized to achieve reversal or amelioration of symptoms of a disease or disorder, whereupon the therapeutic agent described herein (e.g., a compound of Formula (I) and/or (II)) is subsequently administered. In addition, the combination methods, compositions and formulations are not to be limited to the use of only two agents; the use of multiple therapeutic combinations is also envisioned.

In certain embodiments, a dosage regimen to treat, prevent, or ameliorate the condition(s) for which relief is sought, is modified in accordance with a variety of factors. These factors include the disorder from which an individual suffers, as well as the age, weight, sex, diet, and medical condition of an individual. Thus, in various embodiments, the dosage regimen actually employed varies and deviates from the dosage regimens set forth herein.

Pharmaceutical Compositions, Formulations, and Methods of Administration

Provided herein, in certain embodiments, are compositions comprising a therapeutically effective amount of any compound described herein (e.g., a compound of Formulas (I) and/or (II)). Pharmaceutical compositions are formulated using one or more physiologically acceptable carriers including excipients and auxiliaries which facilitate processing of the active compounds into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Provided herein are pharmaceutical compositions that include PIM inhibitors and a pharmaceutically acceptable diluent(s), excipient(s), or carrier(s). In addition, the PIM inhibitor is optionally administered as pharmaceutical compositions in which it is mixed with other active ingredients, as in combination therapy. In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances. A pharmaceutical composition, as used herein, refers to a mixture of a PIM inhibitor with other chemical components, such as carriers, stabilizers, diluents, dispersing agents, suspending agents, thickening agents, and/or excipients. The pharmaceutical composition facilitates administration of the PIM inhibitor to an organism. In practicing the methods treatment or use provided herein, therapeutically effective amounts of a PIM inhibitor are administered in a pharmaceutical composition to a mammal having a condition, disease, or disorder to be treated. Preferably, the mammal is a human. A therapeutically effective amount varies depending on the severity and stage of the condition, the age and relative health of an individual, the potency of the PIM inhibitor used and other factors. The PIM inhibitor is optionally used singly or in combination with one or more therapeutic agents as components of mixtures.

The pharmaceutical formulations described herein are optionally administered to an individual by multiple administration routes, including but not limited to, oral, parenteral (e.g., intravenous, subcutaneous, intramuscular), intranasal, buccal, topical, rectal, or transdermal administration route. By way of example only, Example 40 describes a parenteral formulation and Examples 41 and 42 describe oral formulations of compounds of the invention.

The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast smelt formulations, tablets, capsules, pills, delayed release formulations, extended release formulations, pulsatile release formulations, multi-particulate formulations, and mixed immediate and controlled release formulations. The pharmaceutical compositions will include at least one PIM inhibitor, as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these PIM inhibitors having the same type of activity. In some embodiments, PIM inhibitors exist as tautomers. All tautomers are included within the scope of the compounds presented herein. Additionally, the PIM inhibitor exists in unsolvated as well as solvated forms with pharmaceutically acceptable solvents such as water, ethanol, and the like. The solvated forms of the PIM inhibitors presented herein are also considered to be disclosed herein.

"Carrier materials" include any commonly used excipients in pharmaceutics and should be selected on the basis of compatibility with compounds disclosed herein, such as, a PIM inhibitor, and the release profile properties of the desired dosage form. Exemplary carrier materials include, e.g., binders, suspending agents, disintegration agents, filling agents, surfactants, solubilizers. stabilizers, lubricants, wetting agents, diluents, and the like. Moreover, the pharmaceutical compositions described herein, which include a PIM inhibitor, are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multi-particulate formulations, and mixed immediate release and controlled release formulations. In some embodiments, a formulation comprising a PIM3 inhibitor is a solid drug dispersion. A solid dispersion is a dispersion of one or more active ingredients in an inert carrier or matrix at solid state prepared by the melting (or fusion), solvent, or melting-solvent methods. (See: Chiou, W. L., Riegelman, S., J. Pharm. Sci., 1971, 60, 1281-1302). The dispersion of one or more active agents in a solid diluent is achieved without mechanical mixing. Solid dispersions are also called solid-state dispersions. In some embodiments, any compound described herein (e.g., a compound of Formula (I) and/or (II)) is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion. In some embodiments, such amorphous dispersions are filled in capsules and/or constituted into oral powders for reconstitution. Solubility of an SDD comprising a drug is higher than the solubility of a crystalline form of a drug or a non-SDD amorphous form of a drug. In some embodiments of the methods described herein, PIM inhibitors are administered as SDDs constituted into appropriate dosage forms as described herein.

Pharmaceutical preparations for oral use are optionally obtained by mixing one or more solid excipient with a PIM inhibitor, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate.

If desired, disintegrating agents are added, such as the cross-linked croscarmellose sodium, polyvinylpyrrolidone, agar, or alginic acid or a salt thereof such as sodium alginate. Dragee cores are provided with suitable coatings. For this purpose, concentrated sugar solutions are generally used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are optionally added to the tablets or dragee coatings for identification or to characterize different combinations of active compound doses.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. By way of example, Example 42 describes an oral solid dosage formulation that is a tablet.

In other embodiments, the pharmaceutical formulation is in the form of a powder. In still other embodiments, the pharmaceutical formulation is in the form of a tablet, including but not limited to, a fast-melt tablet. Additionally, pharmaceutical formulations of a PIM inhibitor are optionally administered as a single capsule or in multiple capsule dosage form. In some embodiments. The pharmaceutical formulation is administered in two, or three, or four, capsules or tablets. In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, anti-oxidants, flavoring agents, and carrier materials such as binders, suspending agents, disintegration agents, filling agents, surfactants, solubilizers, stabilizers, lubricants, wetting agents, and diluents. Exemplary microencapsulation materials useful for delaying the release of the formulations including a PIM3 inhibitor, include, but are not limited to, hydroxypropyl cellulose ethers (HPC) such as KLUCEL® or Nisso HPC, low-substituted hydroxypropyl cellulose ethers (L-HPC), hydroxypropyl methyl cellulose ethers (HPMC) such as Seppifilm-LC, PHARMACOAT®, Metolose SR, METHOCEL®-E, Opadry YS, PrimaFlo, Benecel MP824, and Benecel MP843, methylcellulose polymers such as METHOCEL®-A. hydroxypropylmethylcellulose acetate stearate Aqoat (HF-LS, HF-LG, HF-MS) and METOLOSE®, Ethylcelluloses (EC) and mixtures thereof such as E461, ETHOCEL®. AQUALON®-EC, SURELEASE®, Polyvinylalcohol (PVA) such as Opadry AMB, hydroxyethylcelluloses such as NATROSOL®, carboxymethycelluloses, and sodium salts of carboxymethylcelluloses (CMC) such as AQUALON®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as EUDRAGIT® EPO, EUDRAGIT® L30D-55, EUDRAGIT® FS 30D EUDRAGIT® L100-55, EUDRAGIT® L100, EUDRAGIT® S100, EUDRAGIT® RD100, EUDRAGIT® E100, EUDRAGIT® L12.5, EUDRAGIT® S12.5, EUDRAGIT® NE30D, and EUDRAGIT® NE 40D, cellulose acetate phthalate, sepifilms such as mixtures of HPMC and stearic acid, cyclodextrins, and mixtures of these materials.

The pharmaceutical solid oral dosage forms including formulations described herein, which include a PIM inhibitor, are optionally further formulated to provide a controlled release of the PIM inhibitor. Controlled release refers to the release of the PIM inhibitor from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to an individual over an extended period of time according to a predetermined profile. Such release rates provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In other embodiments, the formulations described herein, which include a PIM inhibitor, are delivered using a pulsatile dosage form. A pulsatile dosage form is capable of providing one or more immediate release pulses at predetermined time points after a controlled lag time or at specific sites. Pulsatile dosage forms including the formulations described herein, which include a PIM inhibitor, are optionally administered using a variety of pulsatile formulations that include, but are not limited to, those described in U.S. Pat. Nos. 5,011,692; 5,017,381, 5,229,135, and 5,840,329. Other pulsatile release dosage forms suitable for use with the present formulations include, but are not limited to, for example, U.S. Pat. Nos. 4,871,549; 5,260,068; 5,260.069; 5,508,040; 5,567,441; and 5,837,284.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the PIM inhibitor, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further include a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401; 6,667,048; and 6,960,563.

Suitable intranasal formulations include those described in, for example, U.S. Pat. Nos. 4,476,116 and 5,116,817 and amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present.

For administration by inhalation, the PIM inhibitor is optionally in a form as an aerosol, a mist or a powder. Pharmaceutical compositions described herein are conveniently delivered in the form of an aerosol spray presentation from pressurized packs or a nebulizer, with the use of a suitable propellant, e.g., difluoromethane, trichlorofluoromethane, dichlorotetrafluoroethane, carbon dioxide or other suitable gas. In the case of a pressurized aerosol, the dosage unit is determined by providing a valve to deliver a metered amount. Capsules and cartridges o such as, by way of example only, gelatin for use in an inhaler or insufflator are formulated containing a powder mix of the PIM inhibitor and a suitable powder base such as lactose or starch.

Buccal formulations that include a PIM inhibitor include those described in, but are not limited to, U.S. Pat. Nos. 4,229,447; 4,596,795; 4,755,386; and 5,739,136. In addition, the buccal dosage forms described herein optionally further include a bioerodible (hydrolysable) polymeric carrier that also serves to adhere the dosage form to the buccal mucosa. The buccal dosage form is fabricated so as to erode gradually over a predetermined time period, wherein the delivery of the PIM inhibitor, is provided essentially throughout. Buccal drug delivery avoids the disadvantages encountered with oral drug administration, e.g., slow absorption, degradation of the active agent by fluids present in the gastrointestinal tract and/or first-pass inactivation in the liver. The biodegradatable (hydrolysable) polymeric carrier generally comprises hydrophilic (water-soluble and water-swellable) polymers that adhere to the wet surface of the buccal mucosa. Examples of polymeric carriers useful herein include acrylic acid polymers and co, e.g., those known as "carbomers" (CARBOPOL®, which may be obtained from B.F. Goodrich, is one such polymer). Other components also be incorporated into the buccal dosage forms described herein include, but are not limited to, disintegrants, diluents, binders, lubricants, flavoring, colorants, preservatives and the like. For buccal or sublingual administration, the compositions optionally take the form of tablets, lozenges, or gels formulated in a conventional manner. By way of example, Examples 43 and 44 describe sublingual formulations.

Transdermal formulations of a PIM inhibitor are administered through the skin. The transdermal formulations described herein include at least three components: (1) a formulation of a PIM inhibitor; (2) a penetration enhancer; and (3) an aqueous adjuvant. In addition, transdermal formulations include components such as, but not limited to, gelling agents, creams and ointment bases, and the like. In some embodiments, the transdermal formulation further includes a woven or non-woven backing to material to enhance absorption and prevent the removal of the transdermal formulation from the skin. In other embodiments, the transdermal formulations described herein maintain a saturated or supersaturated state to promote diffusion into the skin.

In some embodiments, formulations suitable for transdermal administration of a PIM inhibitor employ transdermal delivery devices and transdermal delivery patches and are lipophilic emulsions or buffered, aqueous solutions, dissolved and/or dispersed in a polymer or an adhesive. Such patches are optionally constructed for continuous, pulsatile, or on demand delivery of pharmaceutical agents. Still further, transdermal delivery of the PIM inhibitor is optionally accomplished by means of iontophoretic patches and the like. Additionally, transdermal patches provide controlled delivery of the PIM inhibitor. The rate of absorption is optionally slowed by using rate-controlling membranes or by trapping the PIM inhibitor within a polymer matrix or gel. Conversely, absorption enhancers are used to increase absorption. An absorption enhancer or carrier includes absorbable pharmaceutically acceptable solvents to assist passage through the skin. For example, transdermal devices are in the form of a bandage comprising a backing member, a reservoir containing the PIM inhibitor optionally with carriers, optionally a rate controlling barrier to deliver the PIM inhibitor to the skin of the host at a controlled and predetermined rate over a prolonged period of time, and means to secure the device to the skin.

Formulations that include a PIM inhibitor suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethyleneglycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, a PIM inhibitor is optionally formulated in aqueous solutions, preferably in physiologically compatible buffers such as Hank's solution. Ringer's solution, or physiological saline buffer. For transmucosal administration, penetrants appropriate to the barrier to be permeated are used in the formulation. For other parenteral injections, appropriate formulations include aqueous or non-aqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of the PIM inhibitor in water soluble form. Additionally, suspensions of the PIM inhibitor are optionally prepared as appropriate oily, injection suspensions.

In some embodiments, the PIM inhibitor is administered topically and formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

The PIM inhibitor is also optionally formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The PIM3 inhibitor is optionally used in the preparation of medicaments for the prophylactic and/or therapeutic treatment of a disease or disorder that would benefit, at least in part, from amelioration of symptoms. In addition, a method for treating any of the diseases or conditions described herein in an individual in need of such treatment involves administration of pharmaceutical compositions containing at least one PIM3 inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

In the case wherein the patient's condition does not improve, upon the doctor's discretion the administration of the PIM3 inhibitor is optionally administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the PIM3 inhibitor is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days. 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%. Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained.

In some embodiments, patients require intermittent treatment on a long-term basis upon any recurrence of symptoms. In some embodiments, the pharmaceutical compositions described herein are in unit dosage forms suitable for single administration of precise dosages. In unit dosage form, the formulation is divided into unit doses containing appropriate quantities of one or more PIM inhibitors. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative. The daily dosages appropriate for the PIM3 inhibitor are from about 0.01 to about 2.5 mg/kg per body weight. An indicated daily dosage in the larger mammal, including, but not limited to, humans, is in the range from about 0.5 mg to about 1000 mg, conveniently administered in divided doses, including, but not limited to, up to four times a day or in extended release form. Suitable unit dosage forms for oral administration include from about 1 to about 500 mg active ingredient, from about 1 to about 250 mg of active ingredient, or from about 1 to about 100 mg active ingredient. The foregoing ranges are merely suggestive, as the number of variables in regard to an individual treatment regime is large, and considerable excursions from these recommended values are not uncommon. Such dosages are optionally altered depending on a number of variables, not limited to the activity of the PIM inhibitor used, the disease or condition to be treated, the mode of administration, the requirements of an individual, the severity of the disease or condition being treated, and the judgment of the practitioner.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index which is expressed as the ratio between $LD_{50}$ and $ED_{50}$. PIM inhibitors exhibiting high therapeutic indices are preferred. The data obtained from cell culture assays and animal studies are optionally used in formulating a range of dosage for use in human. The dosage of such PIM inhibitors lies preferably within a range of circulating concentrations that include the $ED_{50}$ with minimal toxicity. The dosage optionally varies within this range depending upon the dosage form employed and the route of administration utilized.

Assays for Identification and Characterization of PIM3 Inhibitors

Small molecule PIM inhibitors are optionally identified in high-throughput in vitro or cellular assays as described, for example, in U.S. Pat. Nos. 8,283,356 B2, 7,671,063 B2, and 8,431,589 B2. PIM inhibitors suitable for the methods described herein are available from a variety of sources including both natural (e.g., bacterial culture, soil or plant extracts) and synthetic. For example, candidate PIM inhibitors are isolated from a combinatorial library, i.e., a collection of diverse chemical compounds generated by either chemical synthesis or biological synthesis by combining a number of chemical "building blocks." For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks, as desired. Theoretically, the systematic, combinatorial mixing of 100 interchangeable chemical building blocks results in the synthesis of 100 million tetrameric compounds or 10 billion pentameric compounds (See, for example, Gallop, M. A., et al., J. Med. Chem., 1994, 37(9), 1233-1251). Each member of a library may be singular and/or may be part of a mixture (e.g. a "compressed library"). The library may comprise purified compounds and/or may be "dirty" (i.e., containing a quantity of impurities). Preparation and screening of combinatorial chemical libraries are documented methodologies (See: Cabilly, S. ed., Combinatorial Peptide Library Protocols in Methods in Molecular Biology, Humana Press, Totowa, N.J., (1998)). Combinatorial chemical libraries include, but are not limited to: diversomers such as hydantoins, benzodiazepines, and dipeptides, as described in, e.g., DeWitt, S. H., et al., Proc. Natl. Acad. Sci. USA., 1993, 90, 6909-6913; analogous organic syntheses of small compound libraries, as described in Chen, C., et al., J. Am. Chem. Soc., 1994, 116, 2661-2662; Oligocarbamates, as described in Cho, C. Y., et al., Science, 1993, 261, 1303-1305: peptidyl phosphonates, as described in Campbell, D. A., Bermak, J. C., J. Org. Chem., 1994, 59, 658-660; and small organic molecule libraries containing, e.g., thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514).

Devices for the preparation of combinatorial libraries are commercially available (see, e.g., 357 MPS, 390 MPS from Advanced Chem Tech, Louisville, Ky.; Symphony from Rainin, Woburn, Mass.; 433A from Applied Biosystems, Foster City, Calif.; and 9050 Plus from Millipore, Bedford, Mass.). A number of robotic systems have also been developed for solution phase chemistries. These systems include automated workstations and automated synthesis systems, such as the Microlab NIMBUS, Microlab VANTAGE, and Microstar systems developed by Hamilton, Inc. (Reno, Nev.), and the FLEX ISYNTH system developed by Chemspeed Technologies, Inc. (New Brunswick, N.J.), as well as many robotic systems utilizing robotic arms (e.g., Stäubli). Any of the above devices are optionally used to generate combinatorial libraries for identification and characterization of PIM inhibitors which mimic the manual synthetic operations performed by small molecule PIM inhibitors suitable for the methods described herein. Any of the above devices are optionally used to identify and characterize small molecule PIM inhibitors suitable for the methods disclosed herein.

The identification of potential PIM inhibitors is determined by, for example, assaying the in vitro kinase activity of PIM kinases in the presence of candidate inhibitors. In such assays, PIM and/or a characteristic PIM fragment produced by recombinant means is contacted with a substrate in the presence of a phosphate donor (e.g., ATP) containing radiolabeled phosphate, and PIM-dependent incorporation is measured. "Substrate" includes any substance containing a suitable hydroxyl moiety that can accept the y-phosphate group from a donor molecule such as ATP in a reaction catalyzed by PIM. The substrate may be an endogenous substrate of PIM, i.e. a naturally occurring substance that is phosphorylated in unmodified cells by naturally-occurring PIM3 (e.g., BAD or Cdc25A)) or any other substance that is not normally phosphorylated by PIM in physiological conditions, but may be phosphorylated in the employed conditions. The substrate may be a protein or a peptide, and the phosphrylation reaction may occur on a serine and/or threonine residue of the substrate. For example, specific substrates, which are commonly employed in such assays include, but are not limited to, histone proteins and myelin basic protein. In some embodiments, PIM3 inhibitors are identified using IMAP® technology or LanthaScreen technology.

Detection of PIM dependent phosphorylation of a substrate can be quantified by a number of means other than measurement of radiolabeled phosphate incorporation. For example, incorporation of phosphate groups may affect physiochemical properties of the substrate such as electrophoretic mobility, chromatographic properties, light absorbance, fluorescence, and phosphorescence. Alternatively, monoclonal or polyclonal antibodies can be generated which selectively recognize phosphorylated forms of the substrate from non-phosphorylated forms whereby allowing antibodies to function as an indicator of PIM3 kinase activity.

High-throughput PIM kinase assays can be performed in, for example, microtiter plates with each well containing PIM kinase or an active fragment thereof, substrate covalently linked to each well, $P^{32}$ radiolabled ATP and a potential PIM inhibitor candidate. Microtiter plates can contain 96 wells or 1536 wells for large scale screening of combinatorial library compounds. After the phosphorylation reaction has completed, the plates are washed leaving the bound substrate. The plates are then detected for phosphate group incorporation via autoradiography or antibody detection. Candidate PIM inhibitors are identified by their ability to decrease the amount of PIM3 phosphotransferase ability upon a substrate in comparison with PIM phosphotransferase ability alone.

The identification of potential PIM inhibitors may also be determined, for example, via in vitro competitive binding assays on the catalytic sites of PIM such as the ATP binding site and/or the substrate binding site. For binding assays on the ATP binding site, a known protein kinase inhibitor with high affinity to the ATP binding site is used such as staurosporine. Staurosporine is immobilized and may be fluorescently labeled, radiolabeled or in any manner that allows detection. The labeled staurosporine is introduced to recombinantly expressed PIM protein or a fragment thereof along with potential PIM3 inhibitor candidates. The candidate is tested for its ability to compete, in a concentration-dependant manner, with the immobilized staurosporine for binding to the PIM protein. The amount of staurosporine bound PIM is inversely proportional to the affinity of the candidate inhibitor for PIM kinases. Potential inhibitors would decrease the quantifiable binding of staurosporine to PIM (See, e.g., Fabian, M. A., et al., Nat. Biotech., 2005, 23, 329-336). Candidates identified from this competitive binding assay for the ATP binding site for PIM3 would then be further screened for selectivity against other kinases for PIM kinase specificity.

The identification of potential PIM inhibitors may also be determined, for example, by in cyto assays of PIM activity in the presence of the inhibitor candidate. Various cell lines and tissues may be used, including cells specifically engineered for this purpose. In cyto screening of inhibitor candidates may assay PIM activity by monitoring the downstream effects of PIM activity as well as other cellular responses such as growth, growth arrest, differentiation, or apoptosis.

Alternatively, PIM-mediated phosphorylation of a downstream target of PIM can be observed in cell based assays by first treating various cell lines or tissues with PIM inhibitor candidates followed by lysis of the cells and detection of PIM mediated events. Cell lines used in this experiment (e.g., pancreatic cancer cell lines such as MIA PaCa-2, PANC-1, PCI35, PCI55, and PCI66) may include cells specifically engineered for this purpose. PIM mediated events include, but are not limited to, PIM mediated phosphorylation of downstream PIM mediators. For example, phosphorylation of downstream PIM mediators can be detected using antibodies that specifically recognize the phosphorylated PIM mediator but not the unphosphorylated form. These antibodies have been described in the literature and have been extensively used in kinase screening campaigns.

Numerous contract research organizations (CROs) offer PIM kinase assay services, including DiscoverX, Inc, (San Diego, Calif.), Reaction Biology Corporation (Malvern, Pa.), and Carna Biosciences (Tokyo, Japan).

The identification of potential PIM inhibitors may also be determined, for example, by in vivo assays involving the use of animal models, including transgenic animals that have been engineered to have specific defects or carry markers that can be used to measure the ability of a candidate substance to reach and/or affect different cells within the organism. For example, mice have been engineered to overexpress PIM, leading to a disease, such as a malignant tumor, that can be treated with a PIM inhibitor.

The compounds of the invention are therefore potentially useful in the prevention or treatment of disorders or diseases where PIM inhibition plays a role, e.g. malignant diseases or disorders. The compounds of the invention are potentially useful in the treatment and/or prevention of cancers of the endodermal organs, including the cecum, intestine, stomach, thymus, liver, pancreas, lungs, esophagus, gallbladder, thyroid and prostate, and which are manifested in a variety of forms, such as by way of example, esophageal adenocarcinoma, squamous cell carcinoma, nasopharyngeal carcinoma, gastric adenocarcinoma, pancreatic ductal adenocarcinoma, hepatocellular carcinoma, gallbladder adenocarcinoma, prostatic adenocarcinoma, colorectal adenocarcinoma, gastrointestinal stromal tumors (GIST), non small cell lung cancer, and gastrointestinal carcinoid tumors. Where a tumor, a tumor disease, a carcinoma or a cancer is mentioned, also metastasis in the original organ or tissue and/or in any other location is implied alternatively or in addition, whatever the location of the tumor and/or metastasis.

For the above uses the required dosage will of course vary depending on the mode of administration, the particular condition to be treated and the effect desired. In general, satisfactory results are indicated to be obtained systemically at daily dosages of from about 0.02 to 25 mg/kg per body weight. An indicated daily dosage in the larger mammal, e.g. humans, is in the range from about 0.2 mg to about 2 g, conveniently administered, for example, in divided doses up to four times a day or in retard form. Suitable unit dosage forms for oral administration comprise from ca. 0.1 to 500 mg active ingredient.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form, e.g. as indicated above. Such salts may be prepared in conventional manner and exhibit the same order of activity as the free compounds.

In accordance with the foregoing, the present invention also provides:

(1) A compound of Formulas (I) or (II), or a pharmaceutically acceptable salt thereof, for use as a pharmaceutical;

(2) A compound of Formulas (I) or (II), or a pharmaceutically acceptable salt thereof, for use as a PIM inhibitor, for example for use in any of the particular indications hereinbefore set forth;

(3) A pharmaceutical composition, e.g. for use in any of the indications herein before set forth, comprising a compound of Formulas (I) or (II), or a pharmaceutically acceptable salt thereof, together with one or more pharmaceutically acceptable diluents or carriers therefor.

(4) A method for the treatment of any of particular indication hereinbefore set forth in a subject in need thereof which comprises administering to the subject an effective amount of a compound of Formulas (I) or (II), or a pharmaceutically acceptable salt thereof;

(5) The use of a compound of Formulas (I) or (II), or a pharmaceutically acceptable salt thereof, for the manufacture of a medicament for the treatment or prevention of a disease or condition in which PIM3 activation plays a role or is implicated; e.g. as discussed above. The compounds of Formula (I)-(V) may be administered as the sole active ingredient or in conjunction with, e.g. as an adjuvant to, other drugs e.g. in immunosuppressive or immunomodulating regimens or other anti-inflammatory agents, e.g. for the treatment or prevention of allo- or xenograft acute or chronic rejection or inflammatory or autoimmune disorders, a chemotherapeutic agent or an anti-infective agent, e.g. an antiviral agent such as e.g. an anti-retroviral agent or an antibiotic. For example, the compounds of Formula (I) may be used in combination with a calcineurin inhibitor, e.g. cyclosporin A, ISA 247 or FK 506; an mTOR inhibitor, e.g. rapamycin, CC1779, ABT578, biolimus-7, biolimus-9, TAFA-93, AP23573, AP23464, or AP23841; an ascomycin having immunosuppressive properties, e.g. ABT-281, ASM981, etc.; corticosteroids; cathepsin S inhibitors; cyclophosphamide; azathioprine; methotrexate; leflunomide; mizoribine; mycophenolic acid; mycophenolate mofetil; 15-deoxyspergualine or an immunosuppressive homologue, analogue or derivative thereof; a sphingosine-1-phosphate receptor agonist, e.g. FTY720 or an analog thereof, e.g Y-36018; monoclonal antibodies to leukocyte receptors, e.g., MHC, CD2, CD3, CD4, CD7, CD8, CD11a/CD18, CD25, CD27, CD28, CD40. CD45, CD58, CD80, CD86, CD137, ICOS, CD150 (SLAM), OX40, 4-1BB or to their ligands, e.g. CD154, or antagonists thereof; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists, e.g. natalizumab (ANTEGREN®); or antichemokine antibodies or antichemokine receptor antibodies or low molecular weight chemokine receptor antagonists, e.g. anti MCP-1 antibodies.

A compound of Formulas (I) and/or (II) may also be used in combination with other antiproliferative agents. Such antiproliferative agents include, but are not limited to:

(i) aromatase inhibitors, e.g. steroids, especially exemestane and formestane and, in particular, non-steroids, especially aminoglutethimide, vorozole, fadrozole, anastrozole and, very especially, letrozole;

(ii) antiestrogens, e.g. tamoxifen, fulvestrant, raloxifene and raloxifene hydrochloride;

(iii) topoisomerase I inhibitors, e.g. topotecan, irinotecan, 9-nitrocamptothecin and the macromolecular camptothecin conjugate PNU-166148 (compound A1 in W099/17804);

(iv) topoisomerase II inhibitors, e.g. the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide;

(v) microtubule active agents, e.g. the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D;

(vi) alkylating agents, e.g. cyclophosphamide, ifosfamide and melphalan;

(vii) histone deacetylase inhibitors;

(viii) farnesyl transferase inhibitors;

(ix) COX-2 inhibitors, e.g. celecoxib (CELEBREX®), rofecoxib (VIOXX®) and lumiracoxib (COX189);

(x) MMP inhibitors;

(xi) mTOR inhibitors;

(xii) antineoplastic anti metabolites, e.g. 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719;

(xiii) platin compounds, e.g. carboplatin, cis-platin and oxaliplatin;

(xiv) compounds decreasing the protein kinase activity and further anti-angiogenic compounds, e.g. (i) compounds which decrease the activity of the Vascular Endothelial Growth Factor (VEGF) (b) the Epidermal Growth Factor (EGF), c-Src, protein kinase C, Platelet-derived Growth Factor (PDGF), Bcr-Abl tyrosine kinase, c-kit, Flt-3 and Insulin-like Growth Factor I Receptor (IGF-IR) and Cyclin-dependent kinases (CDKs); (ii) lmatinib, midostaurin, IRESSA™ (ZD1839), CGP 75166, vatalanib, ZD6474, GW2016, CHIR-200131, CEP-7055/CEP-5214, CP-547632 and KRN-633; (iii) thalidomide (THALOMID), celecoxib (Celebrex), SU5416 and ZD6126;

(xv) gonadorelin agonists, e.g. abarelix, goserelin and goserelin acetate;

(xvi) anti-androgens, e.g. bicalutamide (CASODEX™);

(xvii) bengamides;

(xviii) bisphosphonates, e.g. etridonic acid, clodronic acid, tiludronic acid, pamidronic acid, alendronic acid, ibandronic acid, risedronic acid and zoledronic acid;

(xix) antiproliferative antibodies, e.g. trastuzumab (HERCEPTIN™), Trastuzumab-DM1, erlotinib (TARCEVA™), bevacizumab (AVASTINT™), rituximab (RITUXAN®), PRO64553 (anti-CD40) and 2C4 Antibody;

(xx) Temozolornide (TEMODAL®).

The structure of the active agents identified by code nos., generic or trade names may be taken from the actual edition of the standard compendium "The Merck Index" or from databases, e.g. Patents International (e.g. IMS World Publications).

In accordance with the foregoing the present invention provides in a yet further aspect:

(6) A method as defined above comprising co-administration, e.g., concomitantly or in sequence, of a therapeutically effective amount of (a) a compound of Formulas (I) or (II), or acceptable salt thereof, and b) a second drug substance, said second drug substance being, for example, for use in any of the particular indications hereinbefore set forth.

(7) A combination comprising a therapeutically effective amount of a PIM kinase inhibitor, e.g. a compound of Formula (I) and/or (II) or a pharmaceutically acceptable salt thereof, and a second drug substance, said second drug substance being for example as disclosed above. Where a PIM kinase inhibitor, e.g. a compound of Formula (I) and/or (II), is administered in conjunction with other immunosuppressive, immunomodulatory, anti-inflammatory or antineoplastic agent, e.g. as disclosed above, dosages of the co-administered drug or agent will of course vary depending on the type of co-drug or agent employed, or the specific drug or agent used, or the condition being treated and so forth.

Cell-Free Biosynthesis

In some embodiments, methods and systems for synthesis of compounds and compositions of the present invention, including PIM inhibitors, are in vitro cell-free biosynthesis (CFB) systems that serve as a platform to produce proteins and small molecule metabolites using the cells enzymes and metabolic machinery without the living cell (See: Hodgman, C. E., Jewett, M. C., Metab. Eng., 2012, 14(3), 261-269). Cell-free biosynthesis systems provided herein have numerous applications for drug discovery by allowing rapid expression of natural biosynthetic genes and pathways and by allowing activity screening without the need for plasmid based cloning and in vivo propagation, thus enabling rapid process/product pipelines (creation of small molecule libraries). A key feature of the CFB methods and systems used herein is that biosynthesis pathway flux to a target compound can be optimized by directing resources to user defined objectives and consequently allows for the exploration of a large sequence space. Central metabolism, oxidative phosphorylation, and protein synthesis can be co-activated by the user. The lack of a cell wall also provides for the ability to easily screen toxic metabolites, proteins, and small molecules.

Cell-free biosynthesis methods involving in vitro transcription/translation (TX-TL) have been used to produce (1) proteins (See, for example: Carlson, E. D., et al., Biotechnol. Adv., 2012, 30(5), 1185-1194; Swartz, J., et al., U.S. Pat. No. 7,338,789; Goerke, A. R., et al., U.S. Pat. No. 8,715,958), (2) antibodies and antibody analogs (See, for example: Zimmerman, E. S., et al., Bioconjugate Chem., 2014, 25, 351-361; Thanos, C. D., et al., US Patent No. 2015/0017187 A1), and (3) small molecules (See, for example: Kay, J., et al., Metabolic Engineering, 2015, 32, 133-142; Goering, A. W., et al., ACS Synth Biol., 2017, 6(1), 39-44; Blake, W. J., et al., U.S. Pat. No. 9,469,861).

The CFB methods and systems can be used to rapidly prototype novel complex biocircuits as well as metabolic pathways. Protein expression from multiple DNA pieces, including linear and plasmid based DNA, can be performed. The CFB methods and systems enable modulating concentrations of DNA encoding individual pathway enzymes and testing the related effect on metabolite production. The ability to express multi-enzyme pathways using linear DNA in the CFB methods and systems bypasses the need for in vivo selection and propagation of plasmids. Linear DNA fragments can be assembled in 1 to 3 hours (hrs) via isothermal or Golden Gate assembly techniques and be immediately used for a CFB reaction. The CFB reaction can take place in several hours, e.g. approximately 4-8 hours, or may be run for longer periods up to 48 hours. The use of linear DNA provides a valuable platform for rapid prototyping libraries of DNA/genes. In the CFB methods and systems, mechanisms of regulation and transcription exogenous to E. coli, such as the tet repressor and T7 RNA polymerase, or other host cell extracts, can be supplemented as defined by the user to generate and maximize endogenous properties, diversity or production. The CFB methods and systems further enhance diversity and production of target compounds by modifying endogenous properties including mRNA and DNA degradation rates. ATP regeneration systems that allow for the recycling of inorganic phosphate, a strong inhibitor of protein synthesis, are manipulated in the CFB methods and systems. Redox potential, including e.g., NAD/NADH, NADP/NADPH, are regenerated in CFB, and methods for modifying redox and availability of specific cofactors which in turn enables the user to selectively modulate any reaction in the CFB system.

In alternative embodiments, CFB methods and systems enable in vitro cell-free transcription/translation systems (TX-TL) and function as rapid prototyping platforms for the synthesis, modification and identification of products, e.g., natural products (NPs) or natural product analogs (NPAs), from biosynthetic pathway genes. In alternative embodiments, CFB systems are used for the combinatorial biosynthesis of natural products and natural product analogs, such as those provided in the present invention. In alternative embodiments, CFB systems are used for the rapid prototyping of complex biosynthetic pathways as a way to rapidly assess combinatorial designs for the synthesis of compounds of Formulas (I) or (II). In alternative embodiments, these CFB systems are multiplexed for high-throughput automation for rapid prototyping of natural product pathway genes, the natural products they encode and synthesize, and natural product analogs, such as the compounds of Formulas (I) or (II) provided in the present invention. The CFB methods and systems are described in Culler, S. et al., PCT Application WO2017/031399 A1, and is incorporated herein by reference.

As described herein, the CFB compositions, methods, and systems can be used to rapidly produce analogs of known compounds, for example natural product analogs and secondary metabolic structural analogs, such as compounds of Formulas (I) or (II). Accordingly the CFB methods can be used in the processes described herein that generate product diversity. In some embodiments, methods provided herein include a cell-free (in vitro) biosynthesis (CFB) method for making, synthesizing or altering the structure of compounds of Formulas (I) or (II). The CFB methods can produce in the TX-TL extract or extract mixture at least two or more of the altered compounds to create a library of altered compounds; preferably the library is a natural product analog library, prepared, synthesized or modified by the CFB method.

In alternative embodiments, practicing the invention comprises use of any conventional technique commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Second Edition, Cold Spring Harbor, 1989; and Ausubel et al., "Current Protocols in Molecular Biology," 1987). Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, N Y (1994); and Hale and Marham, The Harper Collins Dictionary of Biology, Harper Perennial, NY (1991) provides those of skill in the art with general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the Specification as a whole.

As used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Methods of Synthesis

Numerous methods are available for the synthesis of compounds such as those represented by Formulas (I) and (II). Some of these methods are reviewed in Rao, B. P. C., et al, Strategies Towards the Synthesis of Staurosporine Indolocarbazole Alkaloid and Its Analogues in Scope of Selective Heterocycles from Organic and Pharmaceutical Perspective, Chapter 4, Intech Publishers; Rijeka, Croatia (EU), 2016. See also: Wilson, L. J. et al., US Patent Application No. US 2007/0249590 A1; Kleinschroth, J. et al., U.S. Pat. No. 5,438,050; Kleinschroth, J. et al., U.S. Pat. No. 5,489,608; Faul, M. M., et al., U.S. Pat. No. 5,665,877; Faul, M. M., et al., U.S. Pat. No. 5,919,946; Faul, M. M., et al., U.S. Pat. No. 5,614,647; Faul, M. M., et al., U.S. Pat. No. 6,037,475.

Scheme 1

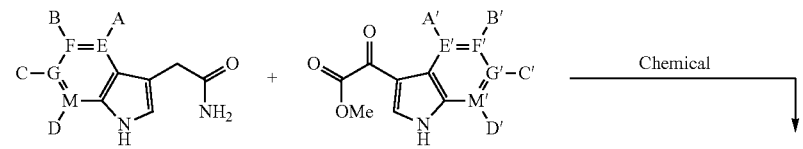

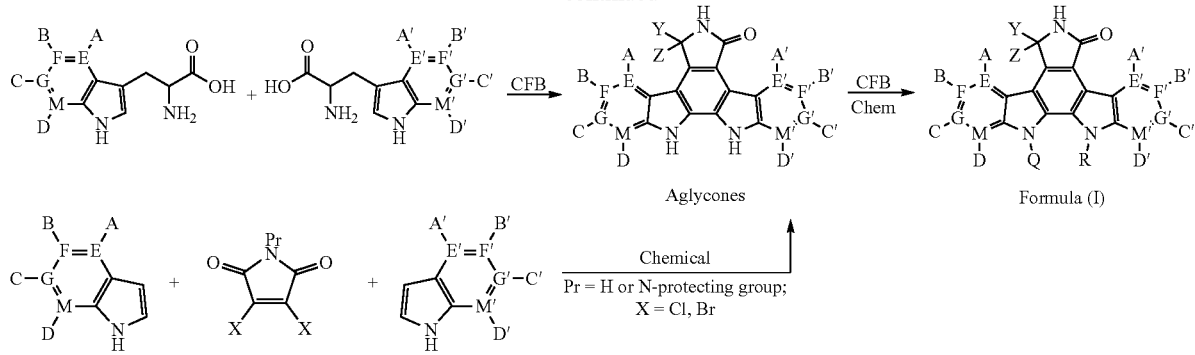

Aglycones

Formula (I)

Pr = H or N-protecting group;
X = Cl, Br

In one embodiment, compounds of Formula (I) may be prepared by reacting indole-3-acetamide derivatives with methyl indole-3-glyoxylates in the presence of potassium tert-butoxide in THF solvent, as shown in Scheme 2 and as reported in the literature (See, for example: Faul, et al., Tetrahedron Lett., 1999, 40, 1109-1112; Faul et al., J. Org. Chem. 1998, 63, 6053-6058; Faul et al., J. Org. Chem. 1999, 64, 2465-2470). Indole-3-acetamide and indole-3-glyoxylate derivatives are readily prepared from a wide range of available substituted indoles. Ring closure of the initially formed bisindolomaleimide derivatives affords the indolo[2,3-a]carbazoles represented by Formula (I), which can be accomplished with a variety oxidants [O], including $Pd(OAc)_2$, $PdCl_2$, $hv/O_2$ or $I_2$, DDQ, $CuCl_2$, or $Pd(OTf)_2$ (See, for example: Faul et al., J. Org. Chem. 1999, 64, 2465-2470).

Scheme 2

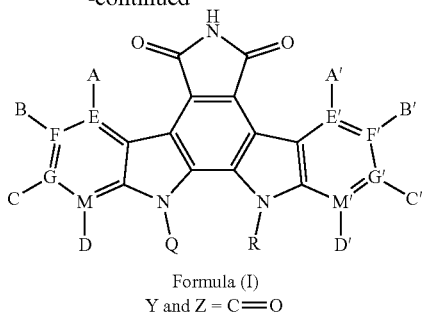

Formula (I)
Y and Z = C=O

In another embodiment, compounds of Formula (III) may be prepared by sequentially reacting substituted indoles, which are metallated with Mg or other metals, with 3,4-dihalosuccinimide or its N-protected form, as shown in Scheme 3 (X=Cl, Br) and as described in the literature (See, for example: Faul et al., Synthesis, 1995, 1511-1516; Gallant et al., J. Org. Chem. 1993, 58, 343-349). Compounds of Formula (I) are then prepared by oxidation, as described above for Scheme 2. In both Scheme 2 and Scheme 3, the imide functionality can be reduced to the lactam functionality using standard reagents such as sodium borohydride or zinc amalgam. In Scheme 3, Q and/or R groups can be added by standard methods through reactions with the indole N—H functionality (e.g., through alkylation or acylation reactions).

Scheme 3

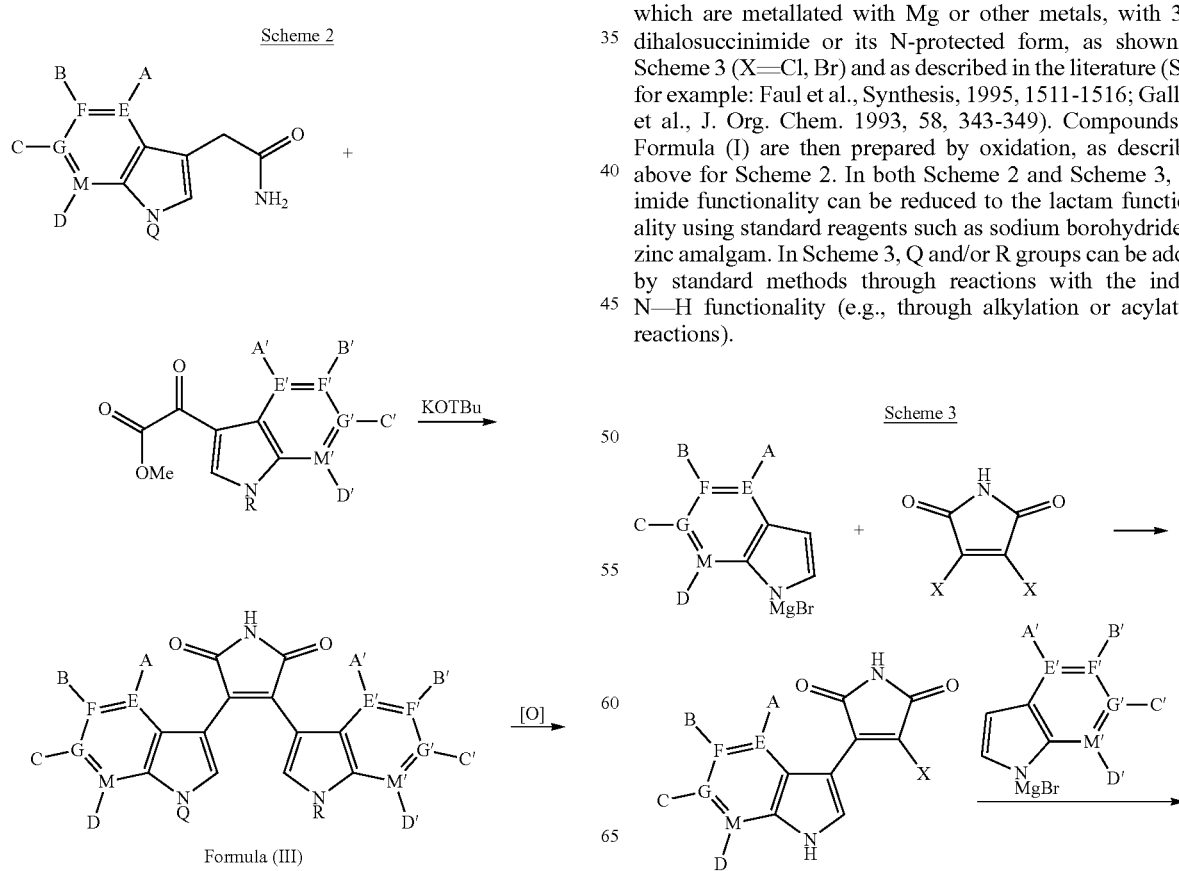

Formula (III)

-continued

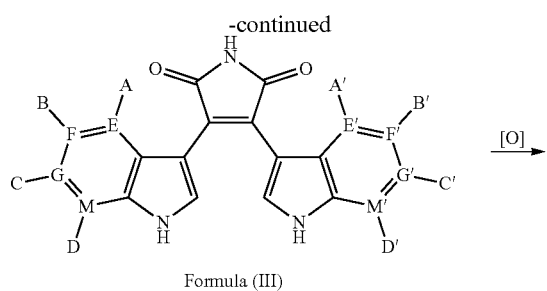

Formula (III)

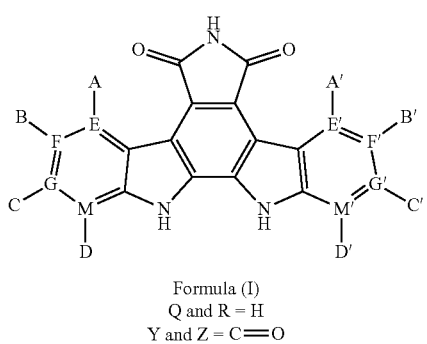

Formula (I)
Q and R = H
Y and Z = C=O

In another embodiment, compounds of Formulas (I) and (III) may be prepared directly by reacting tryptophan derivatives in a process involving cell-free biosynthesis (CFB) as shown in Scheme 4. In this biological process, enzymes are used to condense two tryptophan molecules or tryptophan derivatives to directly produce compounds of Formula (I) where Q and R are hydrogen. The enzymes required for these transformations have been elucidated and enzymes from various pathways can be used to generate indolocarbazole derivatives. Certain enzymes are known to catalyze transformations and facilitate pathways to produce natural indolocarbazole. These enzymes include, by way of example for Formula (I) using process CFB-1: VioA (amino oxidase) and VioB (chromopyrrolic acid synthase) of the violacein pathway, StaO (amino oxidase), StaD (chromopyrrolic acid synthase), StaP (cytochrome P450 monooxygenase), and StaC (flavin hydroxylase) of the staurosporine pathway, and RebO (amino oxidase), RebD (chromopyrrolic acid synthase), RebP (cytochrome P450 monooxygenase), and RebC (flavin hydroxylase) of the rebeccamycin pathway, or homologues thereof (See, for example: Sanchez et al., Nat. Prod. Rep. 2006, 23, 1007-1045; Sanchez et al., Proc. Natl. Acad. Sci. U.S.A., 2005, 102, 461-466; Du et al., ACS Synth. Biol. 2015, 4, 682-688; Du et al., Curr. Opin. Chem. Bio., 2016, 31, 74-81). Similarly, compounds of Formula (III) may be produced using process CFB-2, for example, using the enzymes Vio A and VioB, StaO and StaD, RebO and RebD, or homologues thereof, in combination with the enzyme MarC of the methylarcyriarubin pathway or homologues thereof (See: Chang, F.-Y. and Brady, S. F., ChemBioChem, 2014, 15(6), 815-821). These enzymes have been used herein to directly produce compounds of Formulas (I) and (III), wherein A, B, C, D, A', B', C', D', Q and R are hydrogen, and E, F, G, M, E', F', G', M' are carbon when tryptophan is used as a precursor. These enzymes can be used in engineered living cells, or alternatively in a cell-free process, to produce compounds of Formula (I) and Formula (III). Cell-free biosynthesis of natural product-like compounds is described in Culler, S. et al., PCT Application WO2017/031399 A1, and is incorporated herein by reference.

In one embodiment of the present invention, the enzymes VioA and Vio B of the violacein pathway, StaO, StaD, StaP, and StaC of the staurosporine pathway, and/or RebO, RebD, RebP, and RebC of the rebeccamycin pathway, and/or MarC of the methylarcyriarubin pathway are used in a cell-free biosynthesis process to produce compounds of Formulas (I) or (III) by combining and transforming two of the same or different substituted tryptophan derivatives, as outlined in Scheme 4. Staurosporine pathway enzymes (StaO, StaD, StaP, and StaC), for example, can be used to directly produce compounds of Formula (I) wherein Q, R, Y and Z are hydrogen. Rebeccamycin pathway enzymes (RebO, RebD, RebP, and RebC) can be used to directly produce compounds of Formula (I) wherein Q and R are hydrogen, and Y and Z together form a carbon-oxygen double bond (C=O).

Scheme 4

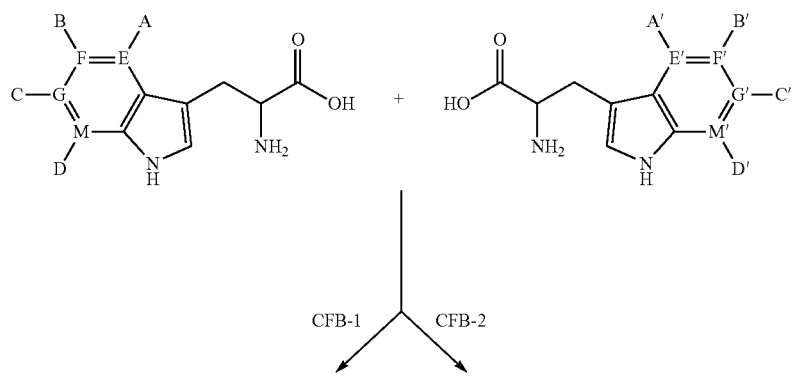

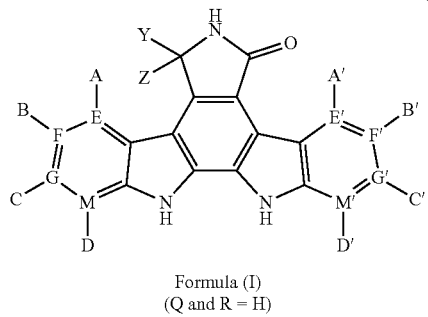

Formula (I)
(Q and R = H)

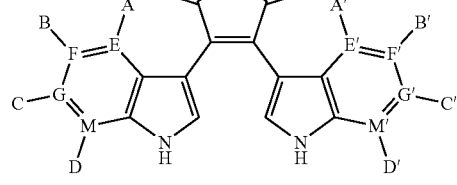

Formula (III)

In another embodiment of the present invention, compounds of Formulas (I) or (III), wherein Q and R are hydrogen, may be transformed through a chemical process to introduce a heteroatom-containing tail attached to the indole N atoms, as represented by Formulas (I) where Q and/or R are not H, and Formula (II), where a macrocyclic ring is formed.

EXAMPLES

General Methods

Examples related to the present invention are described below. In most cases, alternative techniques can be used. The examples are intended to be illustrative and are not limiting or restrictive to the scope of the invention. For example, where additional compounds are prepared following a protocol of a Scheme for a particular compound, it is understood that conditions may vary, for example, any of the solvents, reaction times, reagents, temperatures, work up conditions, or other reaction parameters may be varied. All molecular biology and cell-free biosynthesis reactions were conducted using standard plates, vial, and flasks typically employed when working with biological molecules such as DNA, RNA and proteins. All synthetic chemistry was performed in standard laboratory glassware and equipment unless indicated otherwise in the examples. Commercial reagents were used as received. Analytical HPLC was performed using an Agilent 1100 instrument with a variable wavelength detector. LC/MS was performed on an Applied Biosystems 3200 APCI triple quadrupole mass spectrometer with alternating positive and negative ion scans. High resolution mass spectrometry was performed using a Thermo Fisher Q Exactive MS instrument. GC-MS was performed using an Agilent 6890N instrument equipped with a 5973N inert mass selective detector. Ion chromatography was performed using a Metrohm 940 Professional IC Vario instrument. $^1$H NMR was performed on a Jeol JNM-ECS-400 at 400 MHz or a Bruker DRX-600 at 600 MHz. Microwave reactions were performed in a Biotage Initiator using the instrument software to control heating time and pressure. Hydrogenation reactions were performed on an H-Cube using the commercially available catalyst cartridges. Silica gel chromatography was performed either manually using standard columns or using pre-packed Sep-Pak silica cartridges from Waters. Preparative HPLC was performed on a Waters 1525/2487 with UV detection at 220 nm and manual collection.

Analytical LC/MS Method A:
Column: Zorbax SB-C8 column 4.6 mm×50 mm
Flow rate: 1.0 mL/min
Temperature: 30° C.
Mobile Phase A: 0.1% TFA in water
Mobile Phase B: acetonitrile
Injection amount: 2 μL
HPLC Gradient: 90:10 Phase A:Phase B for 5.0 min, then 10:90 Phase A:Phase B for 1 min, then 100% Phase B for 7 min.

Analytical LC/MS Method B
Column: Zorbax SB-C8 column 4.6 mm×50 mm
Flow rate: 1.0 mL/min
Temperature: 30° C.
Mobile Phase A: 0.1% TFA in water
Mobile Phase B: acetonitrile
Injection amount: 2 μL
HPLC Gradient: 40:60 Phase A:Phase B for 5.0 min, then 10:90 Phase A:Phase B for 1 min, then 100% Phase B for 6 min.

Analytical LC/MS Method C
Column: SunFire C18 column; 4.6 mm×100 mm
Flow rate: 1.0 mL/min
Temperature: 30° C.
Mobile Phase A: 0.1% TFA in water
Mobile Phase B: acetonitrile
Injection amount: 3 μl
HPLC Gradient: 90:10 Phase A:Phase B for 6.0 min, then 10:90 Phase A:Phase B for 1 min, then 100% Phase B for 10 min.

Analytical LC/MS Method D
HPLC column: Hypersil Gold C18, 3 mm×100 mm
Flow rate: 0.3 uL/min
Mobile Phase A: 0.1% Formic acid in water
Mobile Phase B: 0.1% Formic acid in Acetonitrile
Injection amount: 5 μL
HPLC Gradient: 20% B 0-0.5 min, 20%-95% B 0.5-8.5 min, 95% B 8.5-9.8 min, 20% B 10-15 min
Exactive HR MS: ESI in negative and/or positive ionization mode, XIC±10 ppm around exact m/z Compound Synthesis The general synthetic coupling routes that can enable production of compounds of the invention are shown in Schemes 2 and 3. The cell-free biosynthesis (CFB) process shown in Scheme 4 was used for the production of compounds of Formula (I) and (III), as outlined below.

Example 1

Synthesis of 12,13-dihydro-5H-indolo[2,3-a]pyrrolo [3,4-c]carbazole-5,7(6H)-dione (Arcyriaflavin A) Using Cell-Free Biosynthesis (Scheme 4, CFB-1 with tryptophan)

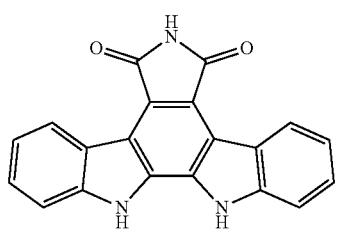

Arcyriaflavin A

Codon-optimized DNA encoding the sequences for the proteins VioA and VioB from *Chromobacterium violaceum*, RebC and RebP from *Lechevalieria aerocolonigenes*, and StaC and StaP from *Streptomyces longisporoflavus* DSM 10189 were synthesized (Thermo Fisher, Carlsbad, Calif.) and individually cloned into a pZE expression vector behind a T7 promoter (Expressys). The resulting plasmids encoding genes for VioA, VioB, RebC, RebP, StaC and StaP proteins were used with or without a C-terminal strep tag. Production of arcyriaflavin A was initiated by adding the vioA, vioB, rebC, and rebP DNA plasmids (SEQ ID NOs:1-4, 15 nM each) to *E. coli* BL21 Star(DE3) cell extracts (15 mg/mL total protein), prepared as described in Kay, J., et al., Met. Eng., 2015, 32, 133-142 and Sun, Z. Z., J. Vis. Exp. 2013, 79, e50762, doi:10.3791/50762, which was pre-mixed with buffer that contains ATP, GTP, TTP, CTP, amino acids, t-RNA, magnesium glutamate, potassium glutamate, potassium phosphate, and other salts, NAD+, NADPH, and glucose to achieve a total volume of 400 μL. Tryptophan (1.5 mM) was added to the facilitate production of Arcyriaflavin A, which was accomplished by incubating the reaction for 18 hours at 22° C. The reaction was then treated with MeOH (1 mL) and centrifuged to remove precipitated protein. The liquid fraction was concentrated and passed through a solid phase extraction (SPE) cartridge (Sep Pak), followed by final purification using silica gel chromatography. $^1$H NMR (400 MHz, DMSO-d$_6$) δ (ppm) 11.72 (br, 2H), 10.01 (br, 1H), 8.99 (d, 2H), 7.80 (d, 2H), 7.55 (m, 2H), 7.35 (dd, 21). LC Retention time 7.79 min (Method D). MS (ESI) m/z 324.076. Arcyriaflavin A thus produced in the cell-free biosynthesis process was identical to the natural material purchased from Santa Cruz Biotechnology (Dallas, Tex.).

Example 2

Synthesis of 6,7,12,13-Tetrahydro-5H-indolo[2,3-a] pyrrolo[3,4-c]carbazol-5-one (K252c) Using Cell-Free Biosynthesis (Scheme 4, CFB-1 with tryptophan)

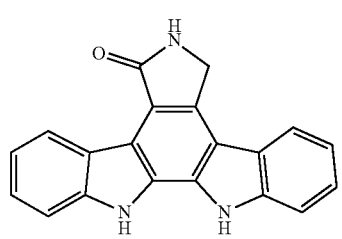

K252c

For production of K252c, the genes rebC and rebP of the rebeccamycin pathway were replaced with the genes staC and staP (SEQ ID NOs: 5 and 6) of the staurosporine pathway in the procedure described above in Example 1. $^1$H NMR (400 MHz, DMSO-d$_6$) δ (ppm) 11.70 (brs, 1H), 11.52 (brs, 1H), 9.20 (d, 1H), 8.44 (brs, 1H), 8.04 (d, 1H), 7.77 (d, 1H), 7.70 (d, 1H), 7.48 (dt, 1H), 7.43 (dt, 1H), 7.31 (dt, 111), 7.22 (dt, 1H), 4.96 (s, 2H). $^{13}$C NMR (100 MHz, DMSO-d$_6$) δ (ppm) 125.5, 125.3, 125.2, 121.6, 120.2, 119.4, 112.2, 111.9, 45.7. LC Retention time 6.96 min (Method D). MS (ESI) m/z 310.095. K252c thus produced in the cell-free biosynthesis process was identical to the natural material purchased from Santa Cruz Biotechnology (Dallas, Tex.).

Example 3

Synthesis of 3,9-difluoro-arcyriaflavin A (129) Using Cell-Free Biosynthesis (Scheme 4, CFB-1 with 5-fluorotryptophan)

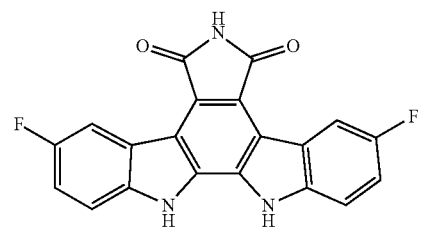

129

Biosynthetic enzymes were selected from a list of VioA, VioB, RebC, and RebP, with SEQ ID NOs:1-4, or homologous enzymes, such as those shown in the non-comprehensive list of homologous enzymes shown below in Table 2. Enzymes were produced and isolated by synthesizing individual codon-optimized genes bearing sequences for C-terminal strep-tags and cloning into the pZE expression vector (Expressys). Following transformation of the plasmids into *E. coli* NEB5α (New England BioLabs, Ipswich, Mass.), the strains were cultivated in 5 L aerated fermenters and the cell mass was isolated by centrifugation and lyzed using a cell homogenizer. Individual enzymes were purified using Strep-Tactin resins (STREP-TACTIN® SUPERFLOW® high capacity cartridge, IBA Lifesciences) following the manufacturer's instructions.

The biosynthesis reaction was performed as follows: To 4 mL Tris buffer (0.1 mM, pH 8.0) was added purified enzymes VioA (3 µM), VioB (3 µM), RebP (3 µM), and RebC (1.5 µM). The reaction was initiated by adding 5-fluorotryptophan (1 mM), along with 5 mM NADH, 1 µM Ferredoxin-NADP$^+$ Reductase from *Spinacia oleracea* (Sigma), and 20 µM Spinach ferrodoxin, and the mixture was incubated at 25° C. for 24 hours. Upon completion, the reaction was treated with MeOH (4 mL) and centrifuged to remove precipitated protein. The liquid fraction was concentrated and passed through a solid phase extraction (SPE) cartridge (Sep Pak), followed by final purification using silica gel chromatography. $^1$H NMR (400 MHz, DMSO-d$_6$) δ (ppm) 11.75 (br, 2H), 10.12 (br, 1H), 8.81 (dd, 2H), 7.68 (d, 2H), 7.42 (dd, 2H). LC Retention time 8.2 min (Analytical LC Method D). MS (ESI) m/z 360.05916 [M–H$^-$]$^-$.

Example 4

Synthesis of 3,4-di(1H-indol-3-yl)-1H-pyrrole-2,5-dione (Arcyriarubin A) Using Cell-Free Biosynthesis (Scheme 4, CFB-2 with tryptophan)

Arcyriarubin A

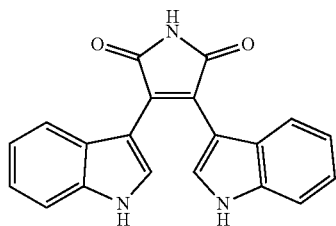

Codon-optimized DNA encoding the sequences for the proteins VioA and VioB from *Chromobacterium violaceum*, and MarC from an uncultured bacterium, were synthesized (Thermo Fisher, Carlsbad, Calif.) and individually cloned into a pZE expression vector behind a T7 promoter (Expressys). The resulting plasmids encoding genes for VioA, VioB, and MarC proteins were used with or without a C-terminal strep tag. Production of arcyriarubin A was initiated by adding 15 nM of each vioA, vioB, and marC DNA plasmids (SEQ ID NOs:1, 2, and, 14) to *E. coli* BL21 Star(DE3) cell extracts (15 mg/mL total protein), prepared as described in Kay, J., et al., Met. Eng., 2015, 32, 133-142 and Sun, Z. Z., J. Vis. Exp. 2013, 79, e50762, doi:10.3791/50762, which was pre-mixed with buffer that contains ATP, GTP, TTP, CTP, amino acids, t-RNA, magnesium glutamate, potassium glutamate, potassium phosphate, and other salts, NAD+, NADPH, and glucose to achieve a total volume of 400 µL. Tryptophan (1.5 mM) was added to the facilitate production of Arcyriarubin A, which was accomplished by incubating the reaction for 18 hours at 22° C. The reaction was then treated with MeOH (1 mL) and centrifuged to remove precipitated protein. The liquid fraction was concentrated and passed through a solid phase extraction (SPE) cartridge (Sep Pak), followed by final purification using silica gel chromatography gave arcyriarubin A as a red solid. $^1$H NMR (400 MHz, CD$_3$OD) δ (ppm) 7.62 (d, 2H), 7.24 (d, 2H), 6.86 (m, 2H), 6.75 (d, 2H), 6.52 (t, 2H); LC Retention time 7.40 min (Method D). MS (ESI) m/z calcd. 327.1001 for C20H13N3O2, found 326.0937 [M–H]$^-$. Arcyriarubin A thus produced in the cell-free biosynthesis process was identical to the natural material purchased from Cayman Chemical (Ann Arbor, Mich.).

Examples 5-37

Synthesis of Compounds shown as Examples 5-28 in Table 1, was accomplished using the same procedure as that described in Example 3 for 3,9-difluoro-arcyriaflavin A(129), but by adding the corresponding substituted tryptophan derivative rather than 5-fluorotryptophan used in Example 3.

Examples 29-37 were produced by following the same general procedure as described in Example 4 for Arcyriarubin A, but by adding the corresponding substituted tryptophan derivative rather than the parent tryptophan precursor. All samples were analyzed by LC-MS and exhibited the expected molecular mass consistent with the compounds listed.

TABLE 1

Examples 5-37

| Example | Compounds | MW (g/mol) | Exact Mass Targeted ±10 ppm m/z | LC Method | LCMS m/z (observed) | LC Ret Time (min) |
|---|---|---|---|---|---|---|
| 5 | 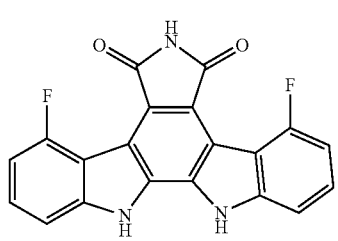 [SMILES: O=C1NC(=O)c2c1c1c([nH]c3cccc(F)c31)c1[nH]c3cccc(F)c3c21] | 128 361.30 | 361.06626 | D | 360.05927 [M – H]$^-$ | 7.45 |

TABLE 1-continued

Examples 5-37

| Example | Compounds | MW (g/mol) | Exact Mass Targeted ±10 ppm m/z | LC Method | LCMS m/z (observed) | LC Ret Time (min) |
|---|---|---|---|---|---|---|
| 6 | | 130   361.30 | 361.06626 | D | 360.05911 [M − H]⁻ | 8.7 |
| 7 | | 131   361.30 | 361.06626 | D | 360.05905 [M − H]⁻ | 9.06 |
| 8 | | 136   483.11 | 480.90609 484.90199 482.90408 | D | 479.89881 483.89471 481.89680 [M − H]⁻ | 9.32 |
| 9 | | 137   483.11 | 480.90609 484.90199 482.90408 | D | 479.8993 483.8972 481.8950 [M − H]⁻ | 9.51 |
| 10 | | 138   483.11 | 480.90609 484.90199 482.90408 | B | 479.89825 483.89725 481.89868 [M − H]⁻ | 1.99 |
| 11 | | 139   483.11 | 480.90609 484.90199 482.90408 | B | 479.8988 483.8965 481.8925 [M − H]⁻ | 1.43 |

TABLE 1-continued

Examples 5-37

| Example | Compounds | MW (g/mol) | Exact Mass Targeted ±10 ppm m/z | LC Method | LCMS m/z (observed) | LC Ret Time (min) |
|---|---|---|---|---|---|---|
| 12 | | 240 353.37 | 353.11637 | D | 352.1085 [M − H]⁻ | 8.70 |
| 13 | | 241 353.37 | 353.11637 | D | 352.10925 [M − H]⁻ | 8.72 |
| 14 | | 242 353.37 | 353.11637 | D | 352.10941 [M − H]⁻ | 8.80 |
| 15 | | 243 353.37 | 353.11637 | D | 352.10934 [M − H]⁻ | 9.02 |
| 16 | | 145 375.34 | 375.07563 | D | 374.06757 [M − H]⁻ | 10.42 |
| 17 | | 146 375.34 | 375.07563 | C | 374.01 [M − H]⁻ | 13.13 |

TABLE 1-continued

|  | Examples 5-37 | | | | | |
| --- | --- | --- | --- | --- | --- | --- |
| Example | Compounds | MW (g/mol) | Exact Mass Targeted ±10 ppm m/z | LC Method | LCMS m/z (observed) | LC Ret Time (min) |
| 18 | | 147  375.34 | 375.07563 | C | 374.15 [M − H]⁻ | 15.17 |
| 19 | | 248  347.32 | 347.08702 | D | 346.07986 [M − H]⁻ | 7.28 |
| 20 | | 249  347.32 | 347.08702 | D | 346.07953 [M − H]⁻ | 7.77 |
| 21 | | 250  347.32 | 347.08702 | D | 346.07974 [M − H]⁻ | 7.96 |
| 22 | | 251  347.32 | 347.08702 | D | 346.07974 [M − H]⁻ | 8.0 |
| 23 | | 247  327.30 | 327.07557 | D | 326.06851 [M − H]⁻ | 7.58 |

TABLE 1-continued

| | Examples 5-37 | | | | | |
|---|---|---|---|---|---|---|
| Example | Compounds | MW (g/mol) | Exact Mass Targeted ±10 ppm m/z | LC Method | LCMS m/z (observed) | LC Ret Time (min) |
| 24 | [structure] | 246  327.30 | 327.07557 | D | 326.06829 [M − H]⁻ | 6.2 |
| 25 | [structure] | 244  327.30 | 327.07557 | D | 326.06855 [M − H]⁻ | 7.68 |
| 26 | [structure] | 121  357.32 | 357.07489 | D | 356.06830 [M − H]⁻ | 6.2 |
| 27 | [structure] | 122  357.32 | 357.07489 | A | 358.11 (M + H)⁺ | 3.69 |
| 28 | [structure] | 123  357.32 | 357.07489 | A | 358.18 (M + H)⁺ | 4.02 |
| 29 | [structure] | 252  363.32 | 363.08193 | D | 362.07477 | 7.34 |

TABLE 1-continued

Examples 5-37

| Example | Compounds | | MW (g/mol) | Exact Mass Targeted ±10 ppm m/z | LC Method | LCMS m/z (observed) | LC Ret Time (min) |
|---|---|---|---|---|---|---|---|
| 30 | (5,5'-difluoro bisindolylmaleimide) | 253 | 363.32 | 363.08193 | D | 362.07443 | 7.56 |
| 31 | (6,6'-difluoro bisindolylmaleimide) | 254 | 363.32 | 363.08193 | D | 361.07437 | 7.74 |
| 32 | (7,7'-difluoro bisindolylmaleimide) | 255 | 363.32 | 363.08193 | D | 362.07474 | 7.83 |
| 33 | (5,5'-dimethyl bisindolylmaleimide) | 257 | 355.39 | 355.13208 | D | 355.13208 | 8.10 |
| 34 | (6,6'-dimethyl bisindolylmaleimide) | 258 | 355.39 | 355.13208 | D | 354.12485 | 8.13 |
| 35 | (7,7'-dimethyl bisindolylmaleimide) | 259 | 355.39 | 355.13208 | D | 354.12480 | 8.06 |

TABLE 1-continued

Examples 5-37

| Example | Compounds | MW (g/mol) | Exact Mass Targeted ±10 ppm m/z | LC Method | LCMS m/z (observed) | LC Ret Time (min) |
|---|---|---|---|---|---|---|
| 36 | [structure: 3,3'-(2,5-dioxo-2,5-dihydro-1H-pyrrole-3,4-diyl)bis(5-bromo-1H-indole)] | 261 485.13 | 484.91976 | D | 481.9147 | 8.31 |
| 37 | [structure: 3,3'-(2,5-dioxo-2,5-dihydro-1H-pyrrole-3,4-diyl)bis(7-bromo-1H-indole)] | 263 485.13 | 484.91976 | D | 481.9147 | 8.68 |

Example 38

Synthesis of 12,13-dihydro-12-(2-(4-morpholine)ethyl)-5H-Indolo[2,3-a]pyrrolo[3,4-c]carbazole-5,7(6H)-dione (3)

Step 1. Synthesis of 6,12-di(tert-butyloxycarbonyl)-12,13-dihydro-5H-indolo[2,3-a]pyrrolo[3,4-c]carbazole-5,7(6H)-dione This compound was prepared according to the procedure described by Slater, M. J., et al, (Bioorg Med. Chem. Lett., 2001, 11, 1993-1995). To a solution of arcyriaflavin A (32 mg, 0.085 mmol) in dry N,N-dimethylformamide (320 μL) was added sodium hydride (60% dispersion in mineral oil, 7.8 mg, 0.195 mmol) and the reaction mixture was stirred at room temperature for 15 min. To the reaction mixture was added di-tert-butyldicarbonate (52 mg, 0.238 mmol) and the reaction mixture was stirred at room temperature for 3 h. The reaction mixture was diluted with a mixture of saturated sodium bicarbonate solution (100 µL), water (100 µL) and acetonitrile (700 µL). The precipitate was collected and the solid was washed with water (1 mL) to afford the title compound (34.4 mg, 0.065 mmol, 77%) as a yellow crystalline solid. LCMS: 88%, $t_R$=3.588 min, m/z=524.1 [M−H]⁻. This material was used without further purification.

Step 2. Synthesis of 12,13-dihydro-12-(2-(4-morpholine)ethyl)-5H-Indolo[2,3-a]pyrrolo[3,4-c]carbazole-5,7(6H)-dione (3)

To a solution of the compound prepared in step 1 (16 mg, 0.031 mmol) in dry N,N-dimethylformamide (160 µL) was added sodium hydride (60% dispersion in mineral oil, 1.8 mg, 0.045 mmol) and the reaction mixture was stirred at room temperature for 15 min. To the reaction mixture was added 2-(4-morpholine)ethyl bromide (15 mg, 0.077 mmol) and the reaction mixture was stirred at room temperature for 5 h. The reaction was quenched with a mixture of saturated sodium bicarbonate solution (200 µL) and water (200 µL) and the precipitate was collected. The solid was washed with water (1 mL) and dried under an air flow for 15 min. To the crude product was added trifluoroacetic acid (700 µL) and the reaction mixture was stirred at room temperature for 20 min. The reaction mixture was evaporated and the residue was purified by preparative HPLC to afford a 2:1 mixture of two compounds (2.2 mg, 0.005 mmol, 16%) as a yellow crystalline solid. LCMS: 92%, $t_R$=1.167 min and 1.282 min (ca. 2:1 mixture), m/z=439.2 [M+H]⁺. 1H NMR data indicated this mixture was composed of two N-alkylated products, the major product being the imide-N-alkylated compound. This mixture (2.2 mg) was dissolved in 200 microliters of DMSO and subjected to further purification by preparative HPLC under the following conditions to afford 0.5 mg of the desired compound 3 as a pale yellow solid.

Preparative HPLC purification conditions used to purify compound 3:
Flow: 4 mL/min
Wavelength: 254 nm
Column: Phenomenex Luna 5 µM C18(2) 100 Å 250×10 mm (P/N: 00G-4252-N0)
Gradient: 35% Acetonitrile containing 0.1% TFA (isocratic)

Figure 2:
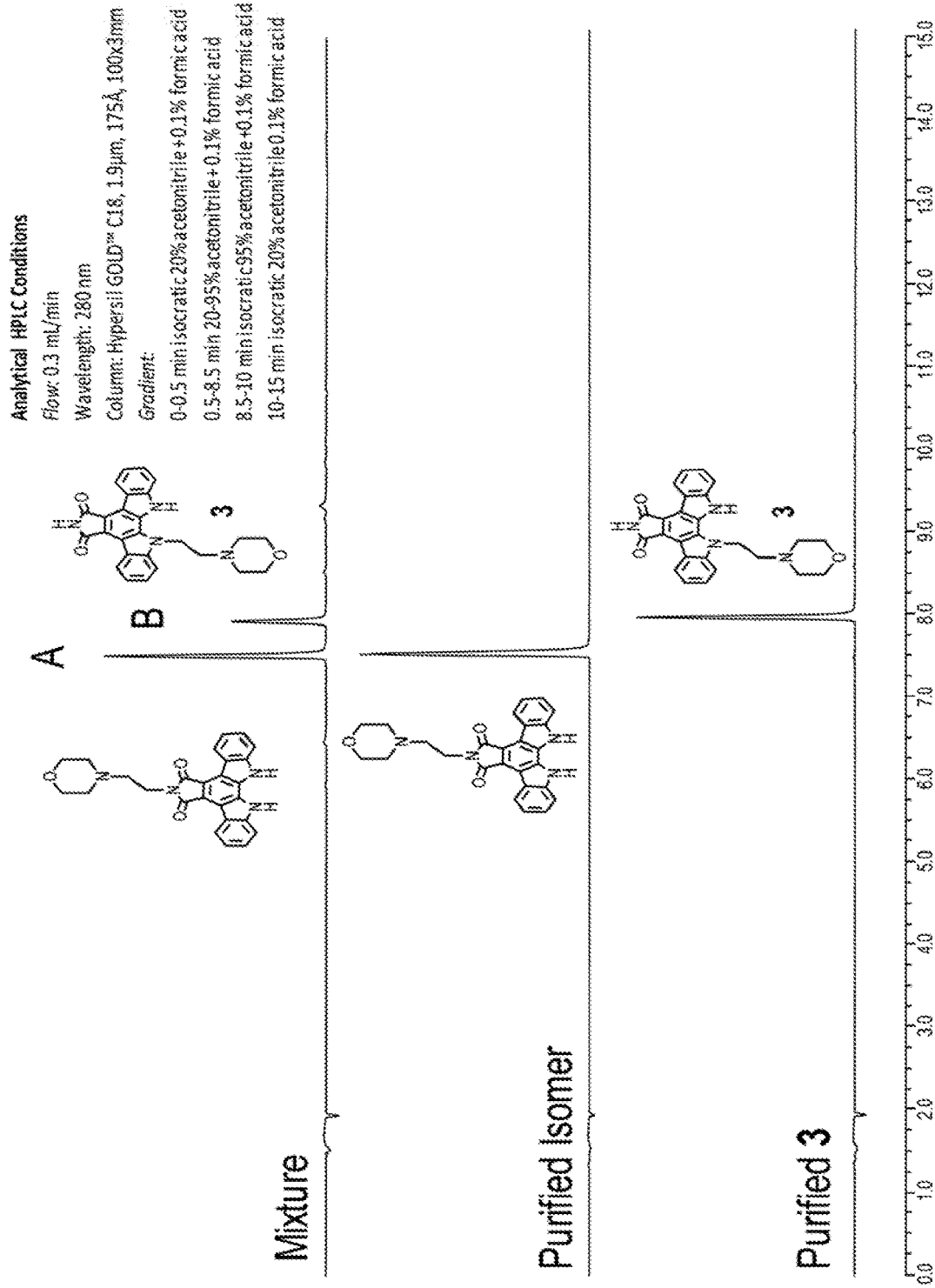
FIG. 2 is a graphical representation of analytical HPLC data showing clean separation of arcyriaflavin alkylation isomers of compound 3.

Pooled fractions containing the two isomeric products were concentrated via lyophilization. Analytical HPLC data (FIG. 2) shows clean separation of the two isomeric alkylation products. NMR analysis confirmed the structure of compound 3. ¹H NMR (400 MHz, 1:1 CD$_3$OD/DMSO-d$_6$) δ (ppm) 9.21 (d, 1H), 9.18 (d, 1H), 7.80 (d, 1H), 7.74 (d, 1H), 7.65 (t, 1H), 7.60 (t, 1H), 7.41 (t, 1H), 7.39 (t, 1H), 3.70 (m, 4H), 3.25 (t(br), 2H), 2.77 (m(br), 6H).

TABLE 2

Examples of Homologous Enzymes for VioA, VioB, RebC, StaC, RebP, StaP, and MarC with Accession Codes

| Name | Accession Number | Sequence Identity | Organism |
| --- | --- | --- | --- |
| VioA | WP_011136821.1 | 100% | Chromobacterium violaceum |
| tryptophan oxidase | WP_081526443.1 | 99% | Chromobacterium violaceum |
| tryptophan oxidase | WP_046166297.1 | 93% | Chromobacterium vaccinii |
| tryptophan oxidase | WP_071109054.1 | 90% | Chromobacterium amazonense |
| tryptophan oxidase | WP_047258238.1 | 80% | Chromobacterium subtsugae |
| VioA | AHZ08835.1 | 50% | Duganella sp. ZLP-XI |
| vioA - tryptophan 2-monooxygenase | WP_063369892.1 | 40% | Pseudoalteromonas luteoviolacea |
| VioB | WP_011136820.1 | 100% | Chromobacterium violaceum |
| iminophenyl-pyruvate dimer synthase VioB | WP_071109055.1 | 98% | Chromobacterium amazonense |
| iminophenyl-pyruvate dimer synthase VioB | WP_021475468.1 | 92% | Pseudogulbenkiania ferrooxidans |
| iminophenyl-pyruvate dimer synthase VioB | WP_047250291.1 | 70% | Chromobacterium subtsugae |
| iminophenyl-pyruvate dimer synthase VioB | WP_094786064.1 | 50% | Zooshikella ganghwensis |
| VioB - polyketide synthase | WP_090933838.1 | 40% | Nonomuraea jiangxiensis |
| VioB-polyketide synthase | AGO88276.1 | 30% | Methylobacterium oryzae CBMB20 |
| RebC | CAC93716.1 | 100% | Lechevalieria aerocolonigenes |
| Chain A, Native And K252c Bound Rebc-10x | 4EIP_A | 98% | Lechevalieria aerocolonigenes |
| RebC-like FAD-binding monooxygenase | AHE14876.1 | 80% | uncultured bacterium |
| FAD-binding monooxygenase | WP_066891569.1 | 66% | Streptomyces thermoautotrophicus |
| FAD-binding monooxygenase | WP_015031968.1 | 60% | Streptomyces venezuelae |
| FAD-binding monooxygenase | WP_036266774.1 | 51% | Mastigocoleus testarum |
| 4-hydroxy-3-nitro-phenylacetate monooxygenase | AEX31240.1 | 35% | Variovorax sp. JS669 |
| FAD-monooxygenase | AAL16082.1 | 32% | Pseudomonas putida |
| StaC | ABI94390.1 | 100% | Streptomyces longisporoflavus |
| monooxygenase | BAF47693.1 | 97% | Streptomyces sp. TP-A0274 |
| FAD-binding monooxygenase | WP_019890945.1 | 81% | Streptomyces purpureus |
| RebC-like FAD-binding monooxygenase | AHE14876.1 | 64% | uncultured bacterium |
| FAD-monooxygenase | WP_091843631.1 | 37% | Bosea lupine |
| RebP | CAC93717.1 | 100% | Lechevalieria aerocolonigenes |
| RebP-like cytochrome P450 | AHE14865.1 | 80% | uncultured bacterium |
| putative cytochrome P450 enzyme | ABC02792.1 | 60% | Actinomadura melliaura |
| StaP-like cytochrome P450 | AHE14737.1 | 51% | uncultured bacterium |
| cytochrome P450 | WP_070920726.1 | 50% | Mycobacterium chelonae |
| cytochrome P450 | WP_055528785.1 | 40% | Streptomyces graminilatus |
| cytochrome P450 | WP_055108234.1 | 34% | Paenibacillus ihumii |
| StaP | ABI94389.1 | 100% | Streptomyces longisporoflavus |
| cytochrome P450 | BAC55212.1 | 95% | Streptomyces sp. TP-A0274 |
| cytochrome P450 | WP_071379123.1 | 75% | Streptomyces sp. MUSC 1 |
| RebP-like cytochrome P450 | AHE14807.1 | 50% | uncultured bacterium |
| cytochrome P450 | WP_061610764.1 | 40% | Sorangium cellulosum |
| cytochrome P450 | WP_079474565.1 | 33% | Marinococcus halophilus |
| MarC | AHE14552.1 | 100% | uncultured bacterium |
| hypothetical protein | WP_034421499.1 | 63% | Candidates entotheonella palauensis |
| (2Fe-2S)-binding protein | WP_067929391.1 | 55% | Alicyclobacillus shizuokensis |

TABLE 2-continued

Examples of Homologous Enzymes for VioA, VioB, RebC, StaC, RebP, StaP, and MarC with Accession Codes

| Name | Accession Number | Sequence Identity | Organism |
|---|---|---|---|
| (2Fe-2S)-binding protein | WP_069938368.1 | 53% | *Domibacillus iocasae* |
| (2Fe-2S)-binding protein | WP_047675330.1 | 50% | *Paenibacillus chondroitinus* |
| (2Fe-2S)-binding protein | WP_061145786.1 | 47% | *Caballeronia arvi* |
| Rieske (2Fe-2S) protein | PCJ77609.1 | 41% | *Dehalococcoidia bacterium* |
| dioxygenase | WP_048859664.1 | 33% | *Acidisphaera rubrifaciens* |

Kinase Assays

Two different assays for measuring kinase inhibitor activity were employed for assessing the effectiveness of compounds of the present invention for inhibiting PIM kinases. One assay was a standard biochemical assay employing radiolabeled ATP, in which inhibitory concentration of 50% of kinase activity ($IC_{50}$) was measured by quantifying the amount of radiolabel incorporation into a standard peptide substrate. The second assay was a competition-based assay wherein binding affinity ($K_d$) was measured by displacement of an immobilized inhibitor of known affinity (e.g., staurosporine) and quantifying the amount of kinase remaining attached to the support following treatment with the inhibitor of interest.

Competition Binding Assays

Inhibitor binding constants ($K_d$) were measured by using active site-dependent competition binding assays essentially as described in Karaman, M. W., et al., Nat. Biotechnol., 2008, 26, 127-132). PIM kinases were labeled with a chimeric double-stranded DNA tag containing the NF-kB binding site (50-GGGAATTCCC-30) fused to an amplicon for qPCR readout, which then were cloned in a modified version of the commercially available T7 Select10 vector and strain (Novagen). DNA-tagged kinase-T7 phage clones were grown in parallel in 24- or 96-well blocks in an *E. coli* BL21-derived strain. *E. coli* was grown to log phase and infected with T7 phage from a frozen stock (multiplicity of infection ca. 0.1) and incubated with shaking at 32° C. until lysis (ca. 90 min). The lysates were centrifuged (6,000 g) and filtered (0.2 mm) to remove cell debris. Extracts were used directly in binding assays without any enzyme purification steps at a ≥10,000-fold overall stock dilution (final DNA-tagged enzyme concentration <0.1 nM).

Streptavidin-coated magnetic beads were treated with biotinylated staurosporine for 30 min at 25° C. to generate affinity resins for kinase assays. The remaining streptavidin sites of the liganded beads were blocked with excess biotin and washed with blocking buffer (SeaBlock (Pierce), 1% BSA, 0.05% Tween 20, 1 mM DTT) to remove unbound ligand and to reduce nonspecific phage binding. Test compounds (compounds of the invention and positive controls) were prepared as 1,000× stock solutions in DMSO and rapidly diluted into the aqueous environment (0.1% DMSO final). DMSO (0.1%) was added to control assays lacking a test compound. All reactions were carried out in polystyrene 96-well plates that had been pretreated with blocking buffer in a final volume of 0.1 ml.

Binding reactions were assembled by combining tagged-kinase extracts, liganded affinity beads and test compounds prepared as 100× stocks in DMSO. DMSO was added to control assays lacking a test compound. Primary screen interactions were performed in 384-well plates, whereas Kd determinations were performed in 96-well plates. Assay plates were incubated in 1× binding buffer (20% SeaBlock, 0.17×PBS, 0.05% Tween 20, 6 mM DTT) at 25° C. with shaking for 1 h, which was sufficient to establish equilibrium. The affinity beads were washed four times with wash buffer (1×PBS, 0.05% Tween 20, 1 mM DTT) to remove unbound phage/protein. After the final wash, the beads were resuspended in elution buffer (1×PBS, 0.05% Tween 20, 2 mM nonbiotinylated affinity ligand) and incubated at 25° C. with shaking for 30 min in order to elute bound kinase. The phage titer and kinase concentration in the eluates was measured by standard plaque assays and quantitative PCR, respectively. Kds were determined using 11 serial threefold dilutions of test compound and a DMSO control. For each assay the affinity probe concentrations were optimized to ensure that true thermodynamic inhibitor $K_d$ values were measured. Binding constants were calculated based on phage concentration in the eluates as described in Fabian, M. A., et al., Nat. Biotechnol., 2005, 23, 329-336.

KINOMEscan™ is based on a competition binding assay that quantitatively measures the ability of a compound to compete with an immobilized, active-site directed ligand. Developed by Karaman, M. W., et al., Nat. Biotechnol., 2008, 26, 127-132, the assay is performed by combining three components: DNA-tagged kinase; immobilized ligand; and a test compound. The ability of the test compound to compete with the immobilized ligand is measured via quantitative PCR of the DNA tag.

To carryout KINOMEscan™ kinase assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. $K_d$s were determined using an 11-point 3-fold compound dilution series with three DMSO control points. All compounds for $K_d$ measurements are distributed by acoustic transfer (non-contact dispensing, Echo 550, LabCyte) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand)

and incubated at room temperature with shaking for 30 minutes. The kinase concentration in the eluates was measured by qPCR.

Binding constants ($K_d$s) were calculated with a standard dose-response curve using the Hill equation:

$$Response = Background + \frac{Signal - Background}{1 + \left(\frac{Kd^{Hill\ Slope}}{Dose^{Hill\ Slope}}\right)}$$

The Hill Slope was set to −1. Curves were fitted using a non-linear least square fit with the Levenberg-Marquardt algorithm.

In this assay involving PIM kinases, compounds of the invention exhibit $K_d$ values in the range of 0.1 nM to 10 μM, preferably in the range 0.1 nM to 10 nM. Arcyriaflavin A of Example 1 exhibits a $K_d$ for PIM3 of 1.9 nM. Positive control inhibitor staurosporine has a $K_d$ of 0.51 nM vs PIM3 using this assay.

In this assay involving PIM1 and PIM2 kinases, compounds of this invention exhibit $K_d$ in the range of 10 nM to 10 μM, preferably in the range 100 nM to >10 μM. Arcyriaflavin A of Example 1 exhibits a $K_d$ for PIM1 of 21 nM and a $K_d$ for PIM2 of 19 nM. Compound 129 of Example 3 exhibits a $K_d$ for PIM1 of 2.5 μM and a $K_d$ for PIM2 of 77 nM. Positive control inhibitor staurosporine has a $K_d$ of 3.2 and 1.9 nM vs PIM1 and PIM2, respectively, using this assay.

Figure 3:
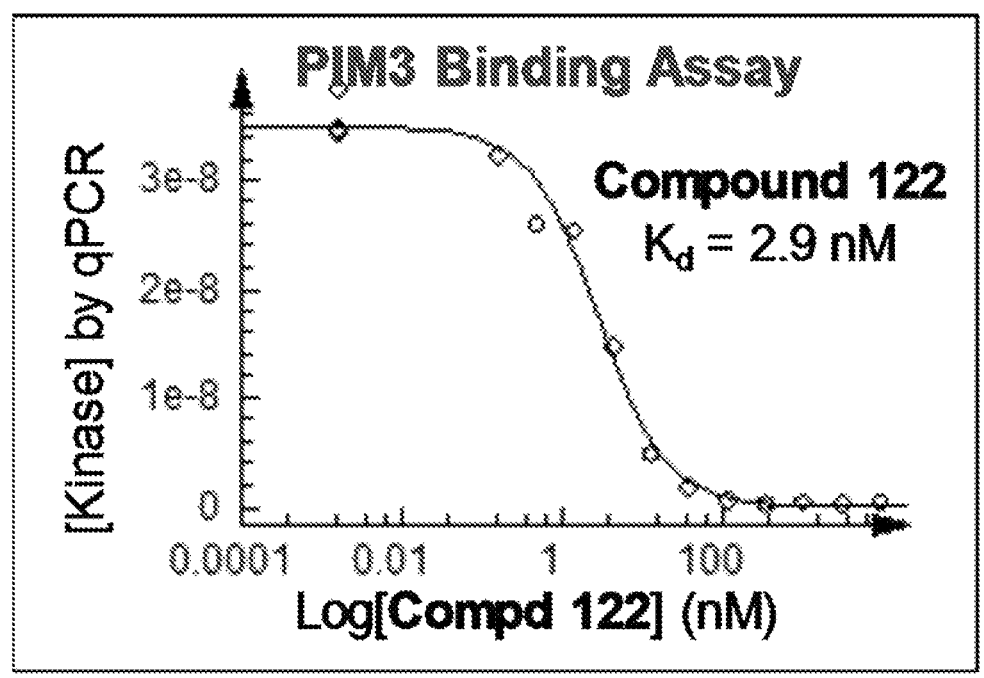
FIG. 3 is a graphical representation of $K_d$ plots for Compound 122 targeting PIM3.

Kinase Inhibition Data:

To obtain kinase inhibition information, each of the Compounds arcyriaflavin, 122, 123, 128-131, 137-139, 146 and 147 was dissolved in 100% dimethyl sulfoxide (DMSO) to yield 10 mM stock. The binding affinity of each compound against PIM kinases was measured with the KINOMEscan™ technology, a competition binding kinase assay developed by Eurofins DiscoverX (Fremont, Calif.). Each assay was run in duplicate. FIG. 3 shows a plot of the amount of kinase measured by qPCR (Signal; y-axis) against the corresponding compound concentration in nM in log 10 scale (x-axis), which was used to calculate the $K_d$ of 3 nM for compound 122 targeting PIM3.

For an example showing how ring substitution impacts binding affinity ($K_d$) of the series of hydroxy-substituted analogs 122-123, fluoro-substituted analogs 128-131, and bromo-substituted analogs 137-139, and cyano-substituted analogs 146-147 for the PIM kinases, see Table 3.

TABLE 3

Kd values (nM) for Compounds AF, 122, 123, 128-131, 137-139, 146 and 147

| Kd (nM) | PIM1 | PIM2 | PIM3 |
| --- | --- | --- | --- |
| Arcyriaflavin | 21 | 19 | 1.9 |
| 122 | 11 | 9 | 3 |
| 123 | 130 | 84 | 6.4 |
| 128 | 280 | 260 | 24 |
| 129 | 2500 | 77 | 27 |
| 130 | 700 | 150 | 48 |
| 131 | 6300 | 2600 | 130 |
| 137 | >10000 | >10000 | >10000 |
| 138 | >10000 | >10000 | >10000 |
| 139 | >3000 | >3000 | >3000 |
| 146 | >10000 | >10000 | >10000 |
| 147 | >3000 | >3000 | >3000 |

Biochemical Kinase Assays

The basic biochemical assay employs radiolabeled ATP to measure the kinase-catalyzed transfer of radioactive phosphorus to a tyrosine-containing peptide substrate, according to the general equation: Reaction: Substrate+[γ-$^{33}$P]-ATP→$^{33}$P-Substrate+ADP The standard protocol used for PIM3 was performed by Reaction Biology Corporation (Malvern, Pa.) using a capture assay performed in 20 mM HEPES at pH 7.5 containing 10 mM MgCl$_2$, 10 mM MnCl$_2$, 1 mM EGTA, 0.02% Brij35, 0.02 mg/mL BSA, 0.1 mM Na$_3$VO$_4$, 2 mM DTT, 0.02% Brij35, 10 μM ATP, and 20 μM peptide substrate RSRHSSYPAGT. Inhibitors in DMSO were added such that the final concentration of DMSO did not exceed 1%, and the enzyme such that the consumption of ATP was less than 10%. Reagents were combined and incubation at 30° C. for 30 min, the reaction was initiated by adding [γ-$^{33}$P]-ATP (10 μCi/mL [γ-$^{33}$P]-ATP) and incubated for 2 h at 30° C. The reaction was then terminated by the addition of one-third volume of stop reagent (0.25 mM EDTA and 33 mM ATP in dH$_2$O). A 15 mL aliquot was removed, spotted onto a P-81 filtermat ion exchange paper and washed sequentially with 10% (w/v) chloroacetic acid and dH2O to remove ATP. The bound $^{33}$P-peptide substrate was quantified by scintillation counting and the disintegrations per minute (dpm) obtained, being directly proportional to the amount of $^{33}$P-peptide produced by PIM3, were used to determine the IC$_{50}$ for each compound. Assays for PIM1 and PIM2 were performed analogously, except for the use of peptide substrates KKRNRTLTK for PIM 1 and RSRHSSYPAGT for PIM2.

In this assay involving PIM3 kinase, compounds of the invention exhibit IC$_{50}$ values in the range of 0.1 nM to 2 μM, preferably in the range 0.1 nM to 10 nM. Arcyriaflavin A of Example 1 exhibits an IC$_{50}$ for PIM3 of 0.13 nM. Positive control inhibitor staurosporine has an IC$_{50}$ of 0.14 nM vs PIM3 using this assay.

In this assay involving PIM1 and PIM2 kinases, compounds of this invention exhibit IC$_{50}$ in the range of 10 nM to 10 μM, preferably in the range 100 nM to >10 μM. Arcyriaflavin A of Example 1 exhibits an IC$_{50}$ for PIM1 of 2.2 nM and for PIM2 of 21 nM using this assay. Compound 129 exhibits an IC$_{50}$ of >2 M for PIM1. Positive control inhibitor staurosporine has an IC$_{50}$ of 4.0 nM and 33 nM vs PIM1 and PIM2, respectively, using this assay.

The inhibitory activity of each compound against PIM kinases was measured with the radioisotope filter binding assay, a type of substrate phosphorylation assays, available at Reaction Biology Corporation (Maven, Pa.) to obtain the IC$_{50}$ values listed in Table 4.

Examples of biochemical inhibition of PIM kinases by arcyriaflavin, ruboxistaurin, the parent structure of Formula (II), and compounds 3, 122 and 123, are shown in Table 4.

TABLE 4

Biochemical inhibition of PIM Kinases by arcyriaflavin, ruboxistaurin, Compounds 3, 122 and 123

| IC$_{50}$ (nM) | PIM1 | PIM2 | PIM3 |
| --- | --- | --- | --- |
| Arcyriaflavin | 2.2 | 21 | 0.3 |
| Ruboxistaurin | 26 | 7650 | 10 |
| 3 | 1.6 | 138 | 0.2 |
| 122 | 0.5 | 5.4 | 0.03 |
| 123 | 3.9 | 55 | 0.2 |

Example 39

Endodermal Cancer Cell-Based Growth Inhibition and Apoptosis Assays for PIM Inhibitors Endodermal cancer cell lines used for proliferation and apoptosis assays are obtained from commercial sources (Creative Bioarray, Shirley, N.Y.; Sigma-Aldrich, St Louis, Mo.; ATCC, Monasses, Va.) and stored and maintained in RPMI-1640 medium (Sigma-Aldrich, St Louis, Mo.) containing 10% fetal bovine serum (Thermo Fisher, Waltham, Mass.) according to provider's instructions. Endodermal cancer cell lines used to screen for PIM inhibitor activity include:
Pancreatic: MIA PaCa-2, PANC-1, Capan-1, PSN1, and JOPACA-1
Colorectal: Caco-2, COLO 320, DLD-1, HCT-15, HCT-116, HT-29, and SW48
Gastric: AGS, SNU-1, SNU-5, Hs 746T, NCI-N87, KATO III, HGC-27, MNK28, MNK45
Hepatic: HepG2, C3A, HuH7, Hep3B, HLE, HLF, SK-Hep1, PLC/PRF/5
Prostate: DU-145, PC-3 and LNCaP, LAPC-4, LAPC-9, and VCaP Measuring Pancreas Cancer Cell Line Proliferation, Apoptosis, and BAD Phosphorylation Five pancreatic cancer cell lines, MIA PaCa-2, PANC-1, Capan-1, PSN1, and JOPACA-1 are cultured in RPMI-1640 medium (Sigma-Aldrich, St Louis, Mo.) containing 10% fetal bovine serum (Thermo Fisher, Waltham, Mass.) at 37° C. in an atmosphere of 5% $CO_2$ in air. Cell suspension ($3$-$10 \times 10^3$ cells/100 µL) is added to the wells of 96-well plates, and pre-incubated for 24 hours. Compounds of the invention in RPMI-1640 (10 µL, final DMSO concentration is 0.5-2.0%) are dispensed into the wells on day 0, and incubation is continued for 72 hours. Cell growth inhibition is measured with a Cell Counting Kit-8 using a direct readout of the water-soluble formazan dye derived from precursor WST-8 (2-(2-methoxy-4-nitrophenyl)-3-(4-nitrophenyl)-5-(2,4-disulfophenyl)-2H-tetrazolium, monosodium salt) (Sigma-Aldrich, St Louis, Mo.), according to the manufacturer's instructions. Cell viability is determined daily by adding 10 µl of WST-8 reagent to each well. After incubation at 37° C. for 2 h, dye absorbance is monitored spectrophotometrically at 450 nm using the PHERAstar Plus microplate reader (BMG Labtech, Germany) and cell counts are quantified based on signal intensity ratios of cell numbers are determined by comparison with the number of viable cells at day 0. PIM inhibitor compounds of the invention inhibit growth of human pancreatic cell lines in the range of concentrations from 10 nM to 10 µM, and most are in the range of 100 nM to 5 µM. Each independent experiment is performed three times.

Pancreatic Cancer Cell Apoptosis Assay

Cells from the proliferation assay described above (with and without PIM inhibitor added) are trypsinized and $2 \times 10^5$ cells are plated in a 6-well plate. After incubation at 37° C. for 24 h, cells are washed and resuspended in 0.5 ml of PBS, 5 µl Annexin V-FITC (Invitrogen—Thermo Fisher, Waltham, Mass., USA), and 1 µl propidium iodide (100 µg/ml). The cells are incubated for 30 min on ice and then analyzed by flow cytometry (CYTOMICS™ FC 500; Beckman Coulter, Miami, Fla., USA) for each treatment. The apoptotic fraction is estimated by dividing the number of apoptotic cells by the total number of cells (minimum of 104 cells). Data are analyzed using Cytomics FC 500 with CXP Software (Beckman Coulter). All observations are reproduced at least three times in independent experiments.

Compounds of the invention are measured for cell growth inhibition and apoptosis induction in pancreatic, gastric, colorectal, hepatic and prostate cancer cell lines. Compounds of the invention inhibited cell growth from 20-100% relative to controls with no inhibitor added. In all cases where inhibition is observed, apoptosis also is detected, demonstrating that PIM inhibition induce programmed cell death by inhibiting the phosphorylation of BAD, which is measured as described below.

Effect of PIM inhibitors on BAD Phosphorylation

Endodermal cancer cells are treated as described above with compounds of the invention for 2 h and then suspended cold phosphate buffered saline, pelleted, and then resuspended in 100-200 µL cold insect cell lysis buffer supplemented with protease inhibitors (Orbigen, Inc., San Diego, Calif.). Cells are lysed by sonication, and subjected to microcentrifugation. Forty micrograms of lysate is loaded in each well of 10% Tris-glycine polyacrylamide minigels for SDS-PAGE analysis. Proteins are transferred to PVDF membranes, blocked for 1 h in TBS-T plus 5% (w/v) powdered blotting grade milk, and then probed overnight at 4° C. with primary P-Bad S112 antibody (Cell Signaling Technology, Danvers, Mass.) at a 1:2000 dilution in blocking solution. Blots are developed using enhanced chemiluminescence reagent ECL Plus (GE Healthcare, Little Chalfont, UK). P-Bad bands are scanned using a GS-800 densitometer (Bio-Rad, Hercules, Calif., USA) to calculate the $EC_{50}$ values.

Cell Growth Inhibition Data:

To obtain growth inhibition data of endodermal cancer cells for PIM kinase inhibitors, Compound 122 was tested against SNU-16, HepG2, MIA PaCa-2, SW480, DU145, HEK-293, PANC-1, and THLE-3 cell lines using CELL TITER-GLO® 2.0 Luminescent Cell Viability Assay (Promega Corporation, Madison, Wis.) at Reaction Biology Corporation (Maven, Pa.). All cell lines were purchased from American Type Culture Collection (ATCC, Manassas, Va.) and maintained in the recommended culture media in the presence of 10% fetal bovind serum, 100 g/mL of penicillin and 100 g/mL of streptomycin at 37° C. in a humidified atmosphere of 5% $CO_2$ and 95% air. To initiate the growth inhibition study, Compound 122 was diluted in DMSO solution with 10-dose and 3-fold dilutions in a source plate starting at 50 mM. The reference compound staurosporine was diluted in DMSO solution with 10-dose and 3-fold dilutions in a source plate starting at 10 mM or 1 mM. 50 nL of Compound 122 or 25 nL of staurosporine was delivered from the source plate to each well of the 384-well cell culture plates by acoustic transfer (non-contact dispensing, Echo 550, LabCyte). 25 µl of culture medium containing 2,000 of respective cells was added to each well of the cell culture plates in duplicate. The cells in the cell culture plates were incubated with the compounds at 37° C. for 72 hours in a humidified atmosphere of 5% $CO_2$ and 95% air. After a 72 hour incubation period, 25 µl of Cell Titer Glo 2.0 reagent was added to each well. The contents were mixed on an orbital shaker for 2 minutes and incubated at room temperature for 15 minutes to stabilize the luminescent signal. Luminescence was recorded by Envision 2104 Multilabel Reader (PerkinElmer, Santa Clara, Calif.). The number of viable cells in culture was determined based on quantitation of the ATP present in each culture well. The $IC_{50}$ curves were plotted and $IC_{50}$ values were calculated using the GraphPad Prism 4 program based on a sigmoidal dose-response equation.

Figure 4:
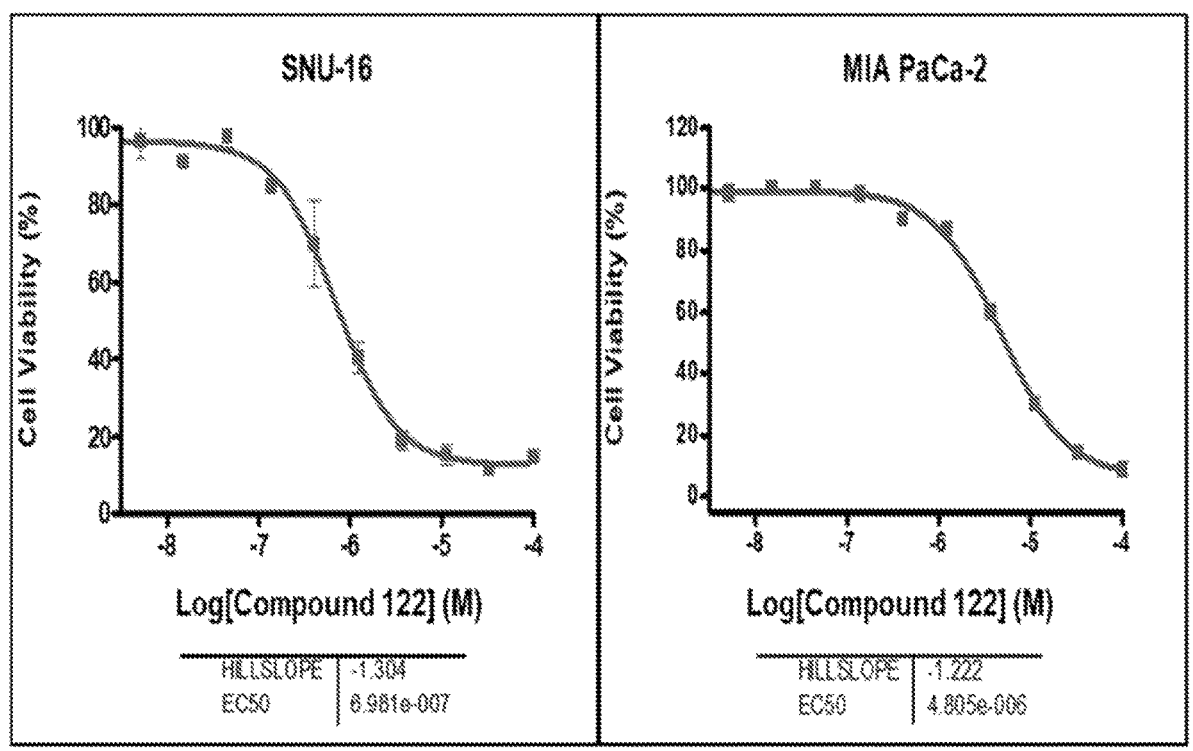
FIG. 4 is a graphical representation of $IC_{50}$ plots for cell lines in SNU-16 and MIA PaCa-2 for Compound 122.

FIG. 4 shows plots of the amount of ATP measured by lumisecence (Signals; y-axis) against the corresponding compound concentration in log 10 scale (x-axis), which was used to calculate the $IC_{50}$ values for Compound 122 in SNU-16 and MIA PaCa-2. Table 5 lists the $IC_{50}$ values for Compound 122 in the tested cell lines.

TABLE 5

$IC_{50}$ values for Compound 122

| Cell Line | Compound 122 $IC_{50}$ (µM) |
|---|---|
| SNU-16 | 0.70 |
| HepG2 | 0.97 |
| THLE-3 | 4.62 |
| SW480 | 2.89 |
| DU145 | 2.33 |
| HEK-293 | 2.70 |
| PANC-1 | no inhibition |
| MIA PaCa-2 | 4.81 |

Example 40

Treatment of Pancreatic Cancer by Administration of a PIM Inhibitor Compound Disclosed Herein in an Animal Model Animal models are used to examine the ability of a PIM inhibitor to ameliorate the growth of pancreatic cancer. PIM inhibitors of the invention are applied in mice where pancreatic tumors have been induced through xenografts created with the transfer of cells into the interperitoneal space of a mouse, or through production of a human-mouse pancreatic tumor xenograft.

Mice. Twelve female BALB/c mice are purchased from The Jackson Laboratory (Bar Harbor, Me., USA). Animals are maintained in accordance with the Guide for the Care and Use of Laboratory Animals. All study protocols are approved by the Institutional Animal Care and Use Committee.

Compounds: Compound 129 is prepared for in vivo interperitoneal administration in PBS vehicle (phosphate-buffered saline: ThermoFisher Scientific Inc., Waltham, Mass.) containing 0.5% methylcellulose/0.025% Tween 20 (Sigma-Aldrich, St. Louis, Mo.).

Pancreatic Cancer Xenograft Mice

Mia-PaCa-2 human pancreatic cancer cells are suspended in Hank's balanced salt solution (HBSS) ($2 \times 10^7$ cells/mL), and the suspension (100 µL) is subcutaneously injected into the back of twelve female BALB/c mice. Mice are maintained for 15 days following injection of Mia-Paca-2 cells, and then randomly split into two groups of eight treatment and four control mice. After establishment of the nude mice xenograft model, tumor dimensions are measured every 3 days using micrometer calipers. PIM inhibitor 129 (50 mg/kg) is administered to the group of eight mice intraperitoneally, while the group of four mice receives vehicle only, once per day (q.d.) for 5 consecutive days, followed by 2 days with no injections, and the cycle is then repeated three times. Mice are weighed daily, starting from the date of Mia-Paca-2 cell injection (day 0). At 43 days after subcutaneous inoculation with Mia-Paca-2 cells, mice are euthanized via carbon dioxide asphyxiation and all tumors are excised immediately following death, weighed and measured, and then snap-frozen in liquid nitrogen. Tumor volume (TV) is calculated by the following formula: $TV=0.5ab^2$, where a is tumor length in mm, and b is tumor width in mm. Compounds of the invention are shown to reduce tumor size from 0%-88% relative to control tumors and mouse body weight is maintained within 10% of day 0 baseline.

Immunofluorescence Analysis of Apoptotic Cells in Xenograft Specimens

Six serial sections (5-µm thick) are obtained for each frozen tumor, mounted on glass slides, and then fixed in 1% paraformaldehyde. Terminal deoxynucleotidyl transferase-mediated nick end labeling-based TUNEL assay for apoptosis detection is performed on four sections using the In Situ BrdU-Red TUNEL assay kit according to the manufacturer's instructions (Abcam, Cambridge, UK). Two tissue sections processed in the absence of terminal deoxynucleotidyl transferase serve as negative controls. The fluorochrome-conjugated anti-BrdU-Red antibody is excited using a 490-nm bandpass filter with emission collected at 576 nm.

Fluorescence microscopy is performed using a 40× objective (Zeiss Plan-Neofluar) on an Olympus Eclipse TE2000-S inverted phase microscope (Olympus, Melville, N.Y., USA). Images are analyzed using Image-Pro Plus software version 4.0. The apoptosis-positive cell numbers in each animal are determined in 10 randomly chosen fields at 400× magnification by an examiner blinded to the experimental procedures. Four sections of the same tumor and four tumors per group are analyzed. Tumors are traced manually with reference to the parallel H&E sections so as to exclude edges and necrotic and nonmalignant tissues from analysis. Apoptotic nuclei, often consisting of clusters of discrete nuclear fragments, can be readily defined using image analysis criteria so as to reject artifacts. The extent of apoptosis in each tumor, expressed as proportional area, is calculated from the sum of the TUNEL-positive pixel area divided by the total viable tumor area.

Statistical analysis. Mean values and standard deviations are calculated for all parameters measured. Mouse weights and tumor weights and volumes between each group are compared using a paired Student's t-test and are reported as mean standard deviation. Comparisons between control and treatment groups are made and statistical significance is evaluated by one-way ANOVA, followed by the Tukey-Kramer test, using SPSS 10 software (IBM, Inc., Chicago, Ill., USA). P-values <0.05 were considered to indicate a statistically significant result.

Formulation Examples

Example 41

Parenteral Formulation

To prepare a parenteral pharmaceutical composition of the compounds of the invention that are suitable for administration by injection, the compounds can be formulated as a mixture and incorporated into a dosage unit form. By way of example, a typical 5 mg/mL parenteral formulation of a compound of the invention proportionally contains, in addition to the compound itself (0.5%), propylene glycol (40%), ethyl alcohol (10%), sodium benzoate/benzoic acid (5%), benzyl alcohol (1.5%), and water (43%).

Example 42

Oral Microemulsion Formulation

To prepare a pharmaceutical composition of the compounds of the invention that are suitable for oral administration, the compounds can be formulated as a mixture and incorporated into a dosage unit form. By way of example, a typical 25 mg oral (capsule) formulation of a compound of the invention contains, in addition to the compound itself, polyoxyl 40 hydrogenated castor oil, gelatin, polyethylene glycol 400, glycerin 85%, dehydrated alcohol, corn oil mono-di-triglycerides, titanium dioxide, vitamin E, ferric oxide yellow, ferric oxide red, carmine, hypromellose 2910, propylene glycol, and purified water.

Example 43

Oral Solid Dosage Formulation

To prepare a pharmaceutical composition of the compounds of the invention that are suitable for oral solid dosage (tablet) administration, the compounds can be formulated as a mixture and incorporated into a dosage unit form. By way of example, a typical 50 mg oral solid dosage formulation of a compound of the invention can be prepared by granulating and compacting into a solid mixture that contains, in addition to the compound itself, excipients, binders and fillers that include modified starch, polyethylene glycol 400, stearyl citrate, polyvinylpyrrolidone, lecithin, mannitol, sorbitol, sage extract, calcium phosphate and gelatin.

Example 44

Sublingual (Hard Lozenge) Composition

To prepare a pharmaceutical composition for buccal delivery, such as a hard lozenge, mix 100 mg of a compound of the invention with 420 mg of powdered sugar mixed, and then with 1.6 mL of light corn syrup, 2.4 mL distilled water, and 0.42 mL mint extract. Gently blend the mixture and pour into a mold to form a lozenge suitable for buccal administration.

Example 45

Fast-Disintegrating Sublingual Tablet

A fast-disintegrating sublingual tablet can be prepared by mixing 48.5% by weight of a compound of a compound of the invention together with 44.5% by weight of microcrystalline cellulose (KG-802), 5% by weight of low-substituted hydroxypropyl cellulose (50 gm), and 2% by weight of magnesium stearate. The formulation can be prepared by mixing the amount of compound of Formula (I) or (IV)-(VI) with the total quantity of microcrystalline cellulose (MCC) and two-thirds of the quantity of low-substituted hydroxypropyl cellulose (L-HPC) by using a three-dimensional manual mixer (INVERSINA®, Bioengineering AG, Switzerland) for 4.5 minutes. All of the magnesium stearate (MS) and the remaining one-third of the quantity of L-HPC are added 30 seconds before the end of mixing. Tablets are prepared by direct compression (AAPS Pharma Sci Tech., 2006; 7(2):E41). The total weight of the compressed tablets is maintained at 150 mg.

What is claimed is:

1. A compound of Formula (I),

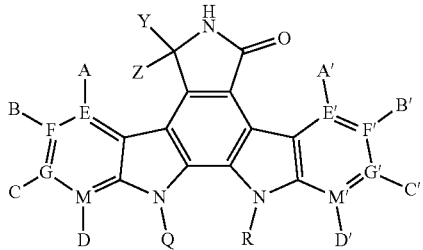

Formula (I)

or a pharmaceutically acceptable salt thereof, wherein:

Y and Z together form a carbon-oxygen double bond (C=O);

Each A, B, C, and D is the same or different and independently selected from H, halogen, —N$_3$, —CN, —NO$_2$, —OH, —OCF$_3$, —OCH$_2$F, —OCF$_2$H, —CF$_3$, —OR$^3$, —N(R$^3$)$_2$, CH$_2$NH$_2$, or —CH$_2$N(R$^3$)$_2$;

Each A', B', C', and D' is the same or different and independently selected from H, halogen, —N$_3$, —CN, —NO$_2$, —OH, —OCF$_3$, —OCH$_2$F, —OCF$_2$H, —CF$_3$, N(R$^3$)$_2$, —OR$^3$;

Each E, F, G, and M is independently C or N;

Each E', F', G', and M' is independently C or N;

Each R$^3$ is independently H, linear or branched substituted or unsubstituted alkyl, substituted or unsubstituted alkenyl, substituted or unsubstituted cycloalkyl, substituted or unsubstituted cycloalkenyl, substituted or unsubstituted heterocycloalkyl substituted or unsubstituted aryl, substituted or unsubstituted heteroaryl, or substituted or unsubstituted acyl (—C(=O)R'), or two R$^3$ together with the atoms to which they are attached form a substituted or unsubstituted heterocycle;

Each Q and/or R is at least one of a branched or linear, substituted or unsubstituted carbon chain of 2-6 carbons, connected at the terminal carbon to the N of a heterocycle containing one or more N, wherein one of Q and R is hydrogen or both Q and R are substituted.

2. The compound of claim 1, or a pharmaceutically acceptable salt thereof, wherein Q and/or R is an alkyl chain containing at least one heteroatom.

3. The compound of claim 1, or a pharmaceutically acceptable salt, wherein Q and/or R is a branched or linear, substituted or unsubstituted carbon chain of 2-6 carbons, connected at the terminal carbon to the N of a piperadinyl, or pyrrolidinyl, piperizinyl or morpholinyl or imidazolyl, or pyrazolyl group, wherein one of Q and R is hydrogen or both Q and R are substituted.

4. The compound of claim 1, or a pharmaceutically acceptable salt, wherein the compound inhibits the catalytic activity of serine/threonine kinases PIM1, PIM2, and/or PIM3.

5. The compound of claim 1, or a pharmaceutically acceptable salt, wherein the compound selectively inhibits the catalytic activity of one or more PIM kinase.

6. The method of inhibiting, or selectively, or partially inhibiting the activity of PIM kinases comprising contacting the PIM kinases with a compound of claim 1 or a pharmaceutically acceptable salt.

7. The method of claim 6 wherein said contacting causes substantially complete inhibition of PIM kinases.

8. The method of claim 6 wherein said contacting causes partial inhibition of PIM kinases.

9. The method of claim 6 wherein contacting modulates cancer cell growth and survival.

10. The method of inhibiting or partially inhibiting the activity of PIM kinases with selective inhibition of PIM3 over PIM1 and PIM2 kinases by a factor of 1.5, 10, 100, 1000, or more, comprising contacting the three kinases, separately or together, in vitro or in vivo, with a compound of claim 6 or a pharmaceutically acceptable salt.

11. A method of synthesizing a compound of Formula (I) wherein tryptophan or tryptophan derivatives are contacted in vitro with a cell-free extract and/or the enzyme combinations comprising VioA (SEQ ID NO:1) and Vio B (SEQ ID NO:2) of the violacein pathway, StaP (SEQ ID NO:5), StaC (SEQ ID NO:6) of the staurosporine pathway, or RebP (SEQ ID NO:4), RebC (SEQ ID NO:3), of the rebeccamycin pathway, or homologues of these enzymes thereof, each representing 25% sequence identity or higher relative to individual SEQ ID NOs:1-6, wherein Y and Z of Formula (I) taken together form a carbon-oxygen double bond (C=O) and wherein Q and R are at least one of a branched or linear, substituted or unsubstituted carbon chain of 2-6 carbons, connected at the terminal carbon to the N of a heterocycle containing one or more N, wherein one of Q and R is hydrogen or both Q and R are substituted.

12. The compound of claim 1 for treating a patient or individual suffering from a malignant disease.

13. The compound of claim 1 for treating a cancer of the endodermal organs comprising cecum, pancreas, liver, stomach, intestine, colon, prostate, thyroid, esophagus, lung, and gallballder cancer.

14. The compound of claim 1 for treating pancreatic cancer, liver cancer, gastric cancer, colorectal cancer, prostate cancer, esophageal adenocarcinoma, squamous cell carcinoma, nasopharyngeal carcinoma, gastric adenocarcinoma, pancreatic ductal adenocarcinoma, hepatocellular carcinoma, gallbladder adenocarcinoma, prostatic adenocarcinoma, colorectal adenocarcinoma, gastrointestinal stromal tumors (GIST), or gastrointestinal carcinoid tumors.

* * * * *

SEQUENCE LISTING

```
<160> NUMBER OF SEQ ID NOS: 7

<210> SEQ ID NO 1
<211> LENGTH: 418
<212> TYPE: PRT
<213> ORGANISM: Chromobacterium violaceum

<400> SEQUENCE: 1

Met Lys His Ser Ser Asp Ile Cys Ile Val Gly Ala Gly Ile Ser Gly
1               5                   10                  15

Leu Thr Cys Ala Ser His Leu Leu Asp Ser Pro Ala Cys Arg Gly Leu
            20                  25                  30

Ser Leu Arg Ile Phe Asp Met Gln Gln Glu Ala Gly Gly Arg Ile Arg
        35                  40                  45

Ser Lys Met Leu Asp Gly Lys Ala Ser Ile Glu Leu Gly Ala Gly Arg
    50                  55                  60

Tyr Ser Pro Gln Leu His Pro His Phe Gln Ser Ala Met Gln His Tyr
65                  70                  75                  80

Ser Gln Lys Ser Glu Val Tyr Pro Phe Thr Gln Leu Lys Phe Lys Ser
                85                  90                  95

His Val Gln Gln Lys Leu Lys Arg Ala Met Asn Glu Leu Ser Pro Arg
            100                 105                 110

Leu Lys Glu His Gly Lys Glu Ser Phe Leu Gln Phe Val Ser Arg Tyr
        115                 120                 125

Gln Gly His Asp Ser Ala Val Gly Met Ile Arg Ser Met Gly Tyr Asp
    130                 135                 140

Ala Leu Phe Leu Pro Asp Ile Ser Ala Glu Met Ala Tyr Asp Ile Val
145                 150                 155                 160

Gly Lys His Pro Glu Ile Gln Ser Val Thr Asp Asn Asp Ala Asn Gln
                165                 170                 175

Trp Phe Ala Ala Glu Thr Gly Phe Ala Gly Leu Ile Gln Gly Ile Lys
            180                 185                 190
```

```
Ala Lys Val Lys Ala Ala Gly Ala Arg Phe Ser Leu Gly Tyr Arg Leu
            195                 200                 205

Leu Ser Val Arg Thr Asp Gly Asp Gly Tyr Leu Leu Gln Leu Ala Gly
            210                 215                 220

Asp Asp Gly Trp Lys Leu Glu His Arg Thr Arg His Leu Ile Leu Ala
225                 230                 235                 240

Ile Pro Pro Ser Ala Met Ala Gly Leu Asn Val Asp Phe Pro Glu Ala
            245                 250                 255

Trp Ser Gly Ala Arg Tyr Gly Ser Leu Pro Leu Phe Lys Gly Phe Leu
            260                 265                 270

Thr Tyr Gly Glu Pro Trp Trp Leu Asp Tyr Lys Leu Asp Asp Gln Val
            275                 280                 285

Leu Ile Val Asp Asn Pro Leu Arg Lys Ile Tyr Phe Lys Gly Asp Lys
            290                 295                 300

Tyr Leu Phe Phe Tyr Thr Asp Ser Glu Met Ala Asn Tyr Trp Arg Gly
305                 310                 315                 320

Cys Val Ala Glu Gly Glu Asp Gly Tyr Leu Glu Gln Ile Arg Thr His
            325                 330                 335

Leu Ala Ser Ala Leu Gly Ile Val Arg Glu Arg Ile Pro Gln Pro Leu
            340                 345                 350

Ala His Val His Lys Tyr Trp Ala His Gly Val Glu Phe Cys Arg Asp
            355                 360                 365

Ser Asp Ile Asp His Pro Ser Ala Leu Ser His Arg Asp Ser Gly Ile
            370                 375                 380

Ile Ala Cys Ser Asp Ala Tyr Thr Glu His Cys Gly Trp Met Glu Gly
385                 390                 395                 400

Gly Leu Leu Ser Ala Arg Glu Ala Ser Arg Leu Leu Leu Gln Arg Ile
            405                 410                 415

Ala Ala

<210> SEQ ID NO 2
<211> LENGTH: 998
<212> TYPE: PRT
<213> ORGANISM: Chromobacterium violaceum

<400> SEQUENCE: 2

Met Ser Ile Leu Asp Phe Pro Arg Ile His Phe Arg Gly Trp Ala Arg
1               5                   10                  15

Val Asn Ala Pro Thr Ala Asn Arg Asp Pro His Gly His Ile Asp Met
            20                  25                  30

Ala Ser Asn Thr Val Ala Met Ala Gly Glu Pro Phe Asp Leu Ala Arg
            35                  40                  45

His Pro Thr Glu Phe His Arg His Leu Arg Ser Leu Gly Pro Arg Phe
        50                  55                  60

Gly Leu Asp Gly Arg Ala Asp Pro Glu Gly Pro Phe Ser Leu Ala Glu
65                  70                  75                  80

Gly Tyr Asn Ala Ala Gly Asn Asn His Phe Ser Trp Glu Ser Ala Thr
            85                  90                  95

Val Ser His Val Gln Trp Asp Gly Gly Glu Ala Asp Arg Gly Asp Gly
            100                 105                 110

Leu Val Gly Ala Arg Leu Ala Leu Trp Gly His Tyr Asn Asp Tyr Leu
            115                 120                 125

Arg Thr Thr Phe Asn Arg Ala Arg Trp Val Asp Ser Asp Pro Thr Arg
        130                 135                 140
```

-continued

```
Arg Asp Ala Ala Gln Ile Tyr Ala Gly Gln Phe Thr Ile Ser Pro Ala
145                 150                 155                 160

Gly Ala Gly Pro Gly Thr Pro Trp Leu Phe Thr Ala Asp Ile Asp Asp
                165                 170                 175

Ser His Gly Ala Arg Trp Thr Arg Gly Gly His Ile Ala Glu Arg Gly
            180                 185                 190

Gly His Phe Leu Asp Glu Glu Phe Gly Leu Ala Arg Leu Phe Gln Phe
        195                 200                 205

Ser Val Pro Lys Asp His Pro His Phe Leu Phe His Pro Gly Pro Phe
    210                 215                 220

Asp Ser Glu Ala Trp Arg Arg Leu Gln Leu Ala Leu Glu Asp Asp Asp
225                 230                 235                 240

Val Leu Gly Leu Thr Val Gln Tyr Ala Leu Phe Asn Met Ser Thr Pro
                245                 250                 255

Pro Gln Pro Asn Ser Pro Val Phe His Asp Met Val Gly Val Val Gly
                260                 265                 270

Leu Trp Arg Arg Gly Glu Leu Ala Ser Tyr Pro Ala Gly Arg Leu Leu
            275                 280                 285

Arg Pro Arg Gln Pro Gly Leu Gly Asp Leu Thr Leu Arg Val Ser Gly
        290                 295                 300

Gly Arg Val Ala Leu Asn Leu Ala Cys Ala Ile Pro Phe Ser Thr Arg
305                 310                 315                 320

Ala Ala Gln Pro Ser Ala Pro Asp Arg Leu Thr Pro Asp Leu Gly Ala
                325                 330                 335

Lys Leu Pro Leu Gly Asp Leu Leu Arg Asp Glu Asp Gly Ala Leu
                340                 345                 350

Leu Ala Arg Val Pro Gln Ala Leu Tyr Gln Asp Tyr Trp Thr Asn His
            355                 360                 365

Gly Ile Val Asp Leu Pro Leu Leu Arg Glu Pro Arg Gly Ser Leu Thr
        370                 375                 380

Leu Ser Ser Glu Leu Ala Glu Trp Arg Glu Gln Asp Trp Val Thr Gln
385                 390                 395                 400

Ser Asp Ala Ser Asn Leu Tyr Leu Glu Ala Pro Asp Arg Arg His Gly
                405                 410                 415

Arg Phe Phe Pro Glu Ser Ile Ala Leu Arg Ser Tyr Phe Arg Gly Glu
            420                 425                 430

Ala Arg Ala Arg Pro Asp Ile Pro His Arg Ile Glu Gly Met Gly Leu
        435                 440                 445

Val Gly Val Glu Ser Arg Gln Asp Gly Asp Ala Ala Glu Trp Arg Leu
    450                 455                 460

Thr Gly Leu Arg Pro Gly Pro Ala Arg Ile Val Leu Asp Asp Gly Ala
465                 470                 475                 480

Glu Ala Ile Pro Leu Arg Val Leu Pro Asp Asp Trp Ala Leu Asp Asp
                485                 490                 495

Ala Thr Val Glu Glu Val Asp Tyr Ala Phe Leu Tyr Arg His Val Met
                500                 505                 510

Ala Tyr Tyr Glu Leu Val Tyr Pro Phe Met Ser Asp Lys Val Phe Ser
            515                 520                 525

Leu Ala Asp Arg Cys Lys Cys Glu Thr Tyr Ala Arg Leu Met Trp Gln
        530                 535                 540

Met Cys Asp Pro Gln Asn Arg Asn Lys Ser Tyr Tyr Met Pro Ser Thr
545                 550                 555                 560
```

Arg Glu Leu Ser Ala Pro Lys Ala Arg Leu Phe Leu Lys Tyr Leu Ala
            565                 570                 575
His Val Glu Gly Gln Ala Arg Leu Gln Ala Pro Pro Ala Gly Pro
            580                 585                 590
Ala Arg Ile Glu Ser Lys Ala Gln Leu Ala Ala Glu Leu Arg Lys Ala
            595                 600                 605
Val Asp Leu Glu Leu Ser Val Met Leu Gln Tyr Leu Tyr Ala Ala Tyr
            610                 615                 620
Ser Ile Pro Asn Tyr Ala Gln Gly Gln Gln Arg Val Arg Asp Gly Ala
625                 630                 635                 640
Trp Thr Ala Glu Gln Leu Gln Leu Ala Cys Gly Ser Gly Asp Arg Arg
            645                 650                 655
Arg Asp Gly Gly Ile Arg Ala Ala Leu Leu Glu Ile Ala His Glu Glu
            660                 665                 670
Met Ile His Tyr Leu Val Val Asn Asn Leu Leu Met Ala Leu Gly Glu
            675                 680                 685
Pro Phe Tyr Ala Gly Val Pro Leu Met Gly Glu Ala Ala Arg Gln Ala
            690                 695                 700
Phe Gly Leu Asp Thr Glu Phe Ala Leu Glu Pro Phe Ser Glu Ser Thr
705                 710                 715                 720
Leu Ala Arg Phe Val Arg Leu Glu Trp Pro His Phe Ile Pro Ala Pro
            725                 730                 735
Gly Lys Ser Ile Ala Asp Cys Tyr Ala Ala Ile Arg Gln Ala Phe Leu
            740                 745                 750
Asp Leu Pro Asp Leu Phe Gly Gly Glu Ala Gly Lys Arg Gly Gly Glu
            755                 760                 765
His His Leu Phe Leu Asn Glu Leu Thr Asn Arg Ala His Pro Gly Tyr
            770                 775                 780
Gln Leu Glu Val Phe Asp Arg Asp Ser Ala Leu Phe Gly Ile Ala Phe
785                 790                 795                 800
Val Thr Asp Gln Gly Glu Gly Gly Ala Leu Asp Ser Pro His Tyr Glu
            805                 810                 815
His Ser His Phe Gln Arg Leu Arg Glu Met Ser Ala Arg Ile Met Ala
            820                 825                 830
Gln Ser Ala Pro Phe Glu Pro Ala Leu Pro Ala Leu Arg Asn Pro Val
            835                 840                 845
Leu Asp Glu Ser Pro Gly Cys Gln Arg Val Ala Asp Gly Arg Ala Arg
            850                 855                 860
Ala Leu Met Ala Leu Tyr Gln Gly Val Tyr Glu Leu Met Phe Ala Met
865                 870                 875                 880
Met Ala Gln His Phe Ala Val Lys Pro Leu Gly Ser Leu Arg Arg Ser
            885                 890                 895
Arg Leu Met Asn Ala Ala Ile Asp Leu Met Thr Gly Leu Leu Arg Pro
            900                 905                 910
Leu Ser Cys Ala Leu Met Asn Leu Pro Ser Gly Ile Ala Gly Arg Thr
            915                 920                 925
Ala Gly Pro Pro Leu Pro Gly Pro Val Asp Thr Arg Ser Tyr Asp Asp
            930                 935                 940
Tyr Ala Leu Gly Cys Arg Met Leu Ala Arg Arg Cys Glu Arg Leu Leu
945                 950                 955                 960
Glu Gln Ala Ser Met Leu Glu Pro Gly Trp Leu Pro Asp Ala Gln Met
            965                 970                 975
Glu Leu Leu Asp Phe Tyr Arg Arg Gln Met Leu Asp Leu Ala Cys Gly

-continued

```
                980             985             990
Lys Leu Ser Arg Glu Ala
            995

<210> SEQ ID NO 3
<211> LENGTH: 529
<212> TYPE: PRT
<213> ORGANISM: Lechevalieria aerocolonigenes

<400> SEQUENCE: 3

Met Asn Ala Pro Ile Glu Thr Asp Val Leu Ile Leu Gly Gly Gly Pro
1               5                   10                  15

Val Gly Met Ala Leu Ala Leu Asp Leu Ala His Arg Gln Val Gly His
            20                  25                  30

Leu Val Val Glu Gln Thr Asp Gly Thr Ile Thr His Pro Arg Val Gly
        35                  40                  45

Thr Ile Gly Pro Arg Ser Met Glu Leu Phe Arg Arg Trp Gly Val Ala
    50                  55                  60

Lys Gln Ile Arg Thr Ala Gly Trp Pro Gly Asp His Pro Leu Asp Ala
65                  70                  75                  80

Ala Trp Val Thr Arg Val Gly Gly His Glu Val Tyr Arg Ile Pro Leu
                85                  90                  95

Gly Thr Ala Asp Thr Arg Ala Thr Pro Glu His Thr Pro Glu Pro Asp
            100                 105                 110

Ala Ile Cys Pro Gln His Trp Leu Ala Pro Leu Leu Ala Glu Ala Val
        115                 120                 125

Gly Glu Arg Leu Arg Thr Arg Ser Arg Leu Asp Ser Phe Glu Gln Arg
    130                 135                 140

Asp Asp His Val Arg Ala Thr Ile Thr Asp Leu Arg Thr Gly Ala Thr
145                 150                 155                 160

Arg Ala Val His Ala Arg Tyr Leu Val Ala Cys Asp Gly Ala Ser Ser
                165                 170                 175

Pro Thr Arg Lys Ala Leu Gly Ile Asp Ala Pro Pro Arg His Arg Thr
            180                 185                 190

Gln Val Phe Arg Asn Ile Leu Phe Arg Ala Pro Glu Leu Arg Ser Leu
        195                 200                 205

Leu Gly Glu Arg Ala Ala Leu Phe Phe Phe Leu Met Leu Ser Ser Ser
    210                 215                 220

Leu Arg Phe Pro Leu Arg Ala Leu Asp Gly Arg Gly Leu Tyr Arg Leu
225                 230                 235                 240

Thr Val Gly Val Asp Asp Ala Ser Lys Ser Thr Met Asp Ser Phe Glu
                245                 250                 255

Leu Val Arg Arg Ala Val Ala Phe Asp Thr Glu Ile Glu Val Leu Ser
            260                 265                 270

Asp Ser Glu Trp His Leu Thr His Arg Val Ala Asp Ser Phe Ser Ala
        275                 280                 285

Gly Arg Val Phe Leu Thr Gly Asp Ala Ala His Thr Leu Ser Pro Ser
    290                 295                 300

Gly Gly Phe Gly Met Asn Thr Gly Ile Gly Ser Ala Ala Asp Leu Gly
305                 310                 315                 320

Trp Lys Leu Ala Ala Thr Leu Arg Gly Trp Ala Gly Pro Gly Leu Leu
                325                 330                 335

Ala Thr Tyr Glu Glu Glu Arg Arg Pro Val Ala Ile Thr Ser Leu Glu
            340                 345                 350
```

-continued

```
Glu Ala Asn Val Asn Leu Arg Arg Thr Met Asp Arg Glu Leu Pro Pro
            355                 360                 365

Gly Leu His Asp Asp Gly Pro Arg Gly Glu Arg Ile Arg Ala Ala Val
    370                 375                 380

Ala Glu Lys Leu Glu Arg Ser Gly Ala Arg Arg Glu Phe Asp Ala Pro
385                 390                 395                 400

Gly Ile His Phe Gly His Thr Tyr Arg Ser Ser Ile Val Cys Gly Glu
                405                 410                 415

Pro Glu Thr Glu Val Ala Thr Gly Gly Trp Arg Pro Ser Ala Arg Pro
                420                 425                 430

Gly Ala Arg Ala Pro His Ala Trp Leu Thr Pro Thr Thr Ser Thr Leu
            435                 440                 445

Asp Leu Phe Gly Arg Gly Phe Val Leu Leu Ser Phe Gly Thr Thr Asp
    450                 455                 460

Gly Val Glu Ala Val Thr Arg Ala Phe Ala Asp Arg His Val Pro Leu
465                 470                 475                 480

Glu Thr Val Thr Cys His Ala Pro Glu Ile His Ala Leu Tyr Glu Arg
                485                 490                 495

Ala His Val Leu Val Arg Pro Asp Gly His Val Ala Trp Arg Gly Asp
            500                 505                 510

His Leu Pro Ala Glu Leu Gly Gly Leu Val Asp Lys Val Arg Gly Ala
    515                 520                 525

Ala

<210> SEQ ID NO 4
<211> LENGTH: 397
<212> TYPE: PRT
<213> ORGANISM: Lechevalieria aerocolonigenes

<400> SEQUENCE: 4

Met Lys Pro Phe Asp Leu Lys Ala Phe Thr Gly Ala Asp Leu Ala Asp
1               5                   10                  15

Pro Tyr Pro Val Tyr Arg Glu Tyr Leu Thr Gly Asp Pro Val His His
                20                  25                  30

Asn Gly Glu Ala Trp Tyr Val Phe Gly Tyr Asp Gly Val Ala His Val
            35                  40                  45

Leu Thr Ser Arg Asp Tyr Gly Arg Arg Gly Pro Gly Gly Arg Ala Thr
    50                  55                  60

Pro Ile Pro Pro Ser His Asp Thr Leu Ser Arg Ile Val Glu Asn Trp
65                  70                  75                  80

Leu Val Phe Leu Asp Pro Pro Arg His Thr Ala Leu Arg Ser Leu Leu
                85                  90                  95

Ala Lys Glu Phe Ser Pro Ala Val Val Thr Gly Leu Arg Glu Arg Val
                100                 105                 110

Arg Lys Ile Ala Gly Glu Leu Leu Ala Gly Leu Gly Asp Ala Gly Glu
            115                 120                 125

Ile Asp Leu Val Glu Asp Phe Ala Ala Pro Leu Pro Ile Leu Val Ile
    130                 135                 140

Ser Glu Leu Leu Gly Val Pro Ala Arg Leu Arg Ser Trp Phe Arg Arg
145                 150                 155                 160

Cys Ala Val Asp Leu Gln Glu Ala Ser Thr Ala Arg Ala Thr Arg Asn
                165                 170                 175

Pro Gly Ala Leu Ala Arg Ala Asp Gly Ala Ala Ser Glu Leu Val Glu
                180                 185                 190
```

-continued

```
Phe Phe Gly Gly Glu Leu Gly Thr Arg Lys Pro Asp Glu Asp Leu
            195                 200                 205

Val Ala Leu Leu Val Asn Ala Gln Arg Arg Gly Glu Ala Leu Thr Asp
    210                 215                 220

Glu Glu Ile Val Ser Thr Cys Val His Leu Leu Thr Ala Gly His Glu
225                 230                 235                 240

Thr Thr Thr Asn Leu Ile Ser Lys Ser Val Leu Ala Leu Leu Ala Asn
                245                 250                 255

Pro Ala Ala Ala Glu Pro Leu Ala Gly Leu Asp Val Thr Pro Gln
            260                 265                 270

Val Val Glu Glu Leu Asn Arg Phe Asp Thr Pro Val Gln Met Val Thr
    275                 280                 285

Arg Trp Ala His Gln Asp Thr Ala Leu Gly Gly Lys Pro Ile Arg Arg
290                 295                 300

Gly Asp Lys Val Val Leu Val Leu Gly Ser Ala Asn Arg Asp Pro Ala
305                 310                 315                 320

Ala Phe Ala Glu Pro Asp Arg Leu Asp Leu Arg Arg Asp Ser Arg Arg
                325                 330                 335

His Cys Gly Phe Gly Leu Gly Ile His Tyr Cys Leu Gly Ala Ala Leu
            340                 345                 350

Ala Arg Thr Glu Ala Glu Ile Gly Leu Ser Val Leu Phe Thr Asn Phe
    355                 360                 365

Pro Gly Leu Arg Leu Gly Gly Glu Pro Val Arg Tyr Ala Asp Asp Leu
    370                 375                 380

Val Phe His Gly Pro Ala Arg Leu Pro Met Leu Thr Arg
385                 390                 395
```

<210> SEQ ID NO 5
<211> LENGTH: 426
<212> TYPE: PRT
<213> ORGANISM: Streptomyces longisporoflavus DSM 10189

<400> SEQUENCE: 5

```
Met Pro Ser Ala Thr Leu Pro Arg Phe Asp Leu Met Gly Trp Asp Lys
1               5                   10                  15

Glu Asp Ile Ala His Pro Tyr Pro Val Tyr Arg Arg Tyr Arg Glu Ala
                20                  25                  30

Ala Pro Val His Arg Thr Ala Gly Pro Gly Lys Pro Asp Thr Tyr
            35                  40                  45

Tyr Val Phe Thr Tyr Asp Asp Val Val Arg Val Leu Ser Asn Arg Arg
    50                  55                  60

Phe Gly Arg Asn Ala Arg Val Ala Ser Gly Asp Thr Gly Pro Asp Thr
65                  70                  75                  80

Ala Pro Val Pro Ile Pro Ala Glu His Arg Ala Leu Arg Thr Val Val
                85                  90                  95

Glu Asn Trp Leu Val Phe Leu Asp Pro Pro Arg His Thr Glu Leu Arg
            100                 105                 110

Ser Leu Leu Thr Gly Glu Phe Ser Pro Ser Ile Val Thr Gly Leu Arg
    115                 120                 125

Pro Arg Ile Ala Glu Leu Ala Ser Glu Leu Leu Asp Arg Leu Arg Ala
    130                 135                 140

His Arg Arg Pro Asp Leu Val Glu Gly Phe Ala Ala Pro Leu Pro Ile
145                 150                 155                 160

Leu Val Ile Ser Ala Leu Leu Gly Ile Pro Ala Glu Asp His Thr Trp
                165                 170                 175
```

-continued

Leu Arg Ala Asn Ala Val Ala Leu Gln Glu Ala Gly Thr Thr Arg Ser
            180                 185                 190

Arg Gly Gly His Gly Tyr Ala Arg Ala Glu Ala Ala Ser Gln Glu Phe
        195                 200                 205

Thr Arg Tyr Phe Arg Arg Glu Val Asp Arg Gly Gly Asp Asp Arg
    210                 215                 220

Asp Asp Leu Leu Thr Leu Leu Val Arg Ala Arg Asp Thr Gly Ser Pro
225                 230                 235                 240

Leu Ser Val Asp Gly Ile Val Gly Thr Cys Val His Leu Leu Thr Ala
                245                 250                 255

Gly His Glu Thr Thr Thr Asn Phe Leu Ala Lys Ala Val Leu Thr Leu
            260                 265                 270

Arg Ala His Pro Asp Val Leu Asp Glu Leu Arg Thr Thr Pro Glu Ser
        275                 280                 285

Thr Pro Ala Ala Val Glu Glu Leu Met Arg Tyr Asp Pro Pro Val Gln
    290                 295                 300

Ala Val Thr Arg Trp Ala Tyr Glu Asp Ile Arg Leu Gly Asp His Asp
305                 310                 315                 320

Ile Pro Arg Gly Ser Arg Val Val Ala Leu Leu Gly Ser Ala Asn Arg
                325                 330                 335

Asp Pro Ala Arg Phe Pro Ala Pro Asp Val Leu Asp Val His Arg Ala
            340                 345                 350

Ala Glu Arg Gln Val Gly Phe Gly Leu Gly Ile His Tyr Cys Leu Gly
        355                 360                 365

Ala Thr Leu Ala Arg Ala Glu Ala Glu Ile Gly Leu Arg Ala Leu Leu
    370                 375                 380

Asp Gly Ile Pro Ala Leu Gly Arg Gly Ala His Glu Val Glu Tyr Ala
385                 390                 395                 400

Asp Asp Met Val Phe His Gly Pro Thr Arg Leu Leu Leu Asp Leu Pro
                405                 410                 415

Asp Ala Thr Cys Pro Ser Ala Ser His Pro
            420                 425

<210> SEQ ID NO 6
<211> LENGTH: 545
<212> TYPE: PRT
<213> ORGANISM: Streptomyces longisporoflavus DSM 10189

<400> SEQUENCE: 6

Met Thr His Ser Gly Glu Arg Thr Asp Val Leu Ile Val Gly Gly Gly
1               5                   10                  15

Pro Val Gly Met Ala Leu Ala Leu Asp Leu Arg Tyr Arg Gly Ile Asp
            20                  25                  30

Cys Leu Val Val Asp Ala Gly Asp Gly Thr Val Arg His Pro Lys Val
        35                  40                  45

Ser Thr Ile Gly Pro Arg Ser Met Glu Leu Phe Arg Arg Trp Gly Ala
    50                  55                  60

Ala Asp Ala Ile Arg Asn Ala Gly Trp Pro Ala Asp His Pro Leu Asp
65                  70                  75                  80

Ile Ala Trp Val Thr Lys Val Gly Gly His Glu Ile Tyr Arg Tyr Arg
                85                  90                  95

Arg Gly Thr Ala Ala Asn Arg Pro Ala Phe Val His Thr Pro Glu Pro
            100                 105                 110

Asp Gln Ile Cys Pro Ala His Trp Leu Asn Pro Val Leu Ile Glu Ala

```
             115                 120                 125
Val Gly Val His Pro Asp Gly Pro Leu Leu Ser Thr Thr Val Asp
    130                 135                 140

Gly Val Val Gln Thr Asp Asp His Val Glu Ala Thr Leu Thr Asp His
145                 150                 155                 160

Ala Thr Gly Thr Thr Gly Thr Val Arg Ala Arg Phe Leu Val Ala Cys
                165                 170                 175

Asp Gly Ala Ser Ser Pro Val Arg Arg Ala Cys Gly Ile Glu Ala Pro
            180                 185                 190

Ala Arg His Arg Thr Gln Val Phe Arg Asn Ile Leu Phe Arg Ala Pro
        195                 200                 205

Glu Leu Lys Asp Arg Leu Gly Glu Arg Ala Ala Leu Val His Phe Leu
    210                 215                 220

Met Leu Ser Ser Thr Leu Arg Phe Pro Leu Arg Ser Leu Asn Gly Ser
225                 230                 235                 240

Asp Leu Tyr Asn Leu Val Val Gly Ala Asp Asp Thr Gly Ala Arg
                245                 250                 255

Pro Asp Ala Leu Ala Leu Ile Lys Asp Ala Leu Ala Leu Asp Thr Pro
            260                 265                 270

Val Glu Leu Leu Gly Asp Ser Ala Trp Arg Leu Thr His Arg Val Ala
        275                 280                 285

Asp Arg Tyr Arg Ala Gly Arg Ile Phe Leu Ala Gly Asp Ala Ala His
    290                 295                 300

Thr Leu Ser Pro Ser Gly Gly Phe Gly Leu Asn Thr Gly Ile Gly Asp
305                 310                 315                 320

Ala Ala Asp Leu Gly Trp Lys Leu Ala Ala Thr Leu Asp Gly Trp Ala
                325                 330                 335

Gly Arg His Leu Leu Asp Thr Tyr Asp Ser Glu Arg Arg Pro Ile Ala
            340                 345                 350

Glu Glu Ser Leu Asn Glu Ala His Asp Asn Leu Arg Arg Thr Met Lys
        355                 360                 365

Arg Glu Val Pro Pro Glu Ile His Leu Asp Gly Pro Glu Gly Glu Arg
    370                 375                 380

Ala Arg Ala Val Met Ala Arg Arg Leu Glu Asn Ser Gly Ala Arg Arg
385                 390                 395                 400

Glu Phe Asp Ala Pro Gln Ile His Phe Gly Leu Arg Tyr Arg Ser Ser
                405                 410                 415

Ala Ile Val Asp Asp Pro Asp Val Pro Val Arg Gln Gly Gln Pro Asp
            420                 425                 430

Ala Asp Trp Arg Pro Gly Ser Glu Pro Gly Tyr Arg Ala Ala His Ala
        435                 440                 445

Trp Trp Asp Ser Thr Thr Ser Thr Leu Asp Leu Phe Gly Arg Gly Phe
    450                 455                 460

Val Leu Leu Arg Phe Ala Asp His Asp Gly Leu Pro Ala Ile Glu Arg
465                 470                 475                 480

Ala Phe Ala Glu Arg Gly Val Pro Leu Thr Val His Gln Gly His Asp
                485                 490                 495

Thr Glu Ile Ala Lys Leu Tyr Ala Arg Ser Phe Val Leu Val Arg Pro
            500                 505                 510

Asp Gly His Val Ala Trp Arg Gly Asp Asp Leu Pro Gly Asp Pro Thr
        515                 520                 525

Ala Leu Val Asp Thr Val Arg Gly Glu Ala Ala Pro Arg Glu Pro Arg
    530                 535                 540
```

Gly
545

<210> SEQ ID NO 7
<211> LENGTH: 445
<212> TYPE: PRT
<213> ORGANISM: Uncultured bacterium

<400> SEQUENCE: 7

Met Leu Ser Ala Glu Asp Asn Lys Leu Leu Thr Glu Val Ala Ala Asp
1               5                   10                  15

Thr Arg Met Gly Gln Leu Leu Arg Arg Tyr Trp His Pro Ile Ala Ala
            20                  25                  30

Ser Ser Gln Leu Asp Asp Lys His Pro Thr Arg Leu Val His Leu Leu
        35                  40                  45

Gly Glu Lys Leu Val Leu Tyr Lys Asp Lys Gln Gly Arg Leu Gly Leu
    50                  55                  60

Ile Asp Glu Arg Cys Pro His Arg Arg Ala Ser Met Leu Tyr Gly Ile
65                  70                  75                  80

Pro Glu Gln Glu Gly Leu Arg Cys Ser Tyr His Gly Trp Leu Phe Asn
                85                  90                  95

Asn Ala Gly Arg Cys Leu Ala Gln Pro Tyr Glu Gln Met Glu Asp Pro
            100                 105                 110

Cys Ser Asn Phe Lys Asp His Val Arg Ile Lys Ser Tyr Pro Val Arg
        115                 120                 125

Glu Leu Gly Gly Leu Val Phe Ala Tyr Leu Gly Pro Ala Pro Ala Pro
    130                 135                 140

Glu Leu Pro Ala Trp Asp Leu Val Thr Glu Asn Leu His Arg Asp
145                 150                 155                 160

Ile Gly Phe Ala Val Val Pro Cys Asn Trp Leu Gln Ile Met Glu Asn
                165                 170                 175

Ala Ala Asp Pro Val His Ala Glu Trp Leu His Gly His Phe Ala Asn
            180                 185                 190

Tyr Val Trp Glu Arg Leu Gly Lys Pro Glu Arg Ile Lys Pro Phe Pro
        195                 200                 205

Thr His Lys Lys Ile Gly Phe Asp Leu Ser Glu Tyr Gly Ile Ile Lys
    210                 215                 220

Arg Arg Val Leu Glu Gly Glu Thr Glu Glu His Glu Asn Trp Lys Phe
225                 230                 235                 240

Gly His Ser Leu Val Phe Pro Asn Leu Gln Lys Gly Gly Leu Gln
                245                 250                 255

Trp Arg Val Pro Met Asp Glu Thr Arg Thr Leu His Val Trp Tyr Tyr
            260                 265                 270

Thr Tyr Thr Pro Ala Glu Gly Thr Val Val Pro Lys Asp Ala Pro Ile
        275                 280                 285

Pro Val Phe Asp Val Pro Val Pro Ala Leu Asp Glu His Gly His Pro
    290                 295                 300

Arg Trp Asp Val Leu Asp Phe Thr Ala Gly Gln Asp Met Val Met Trp
305                 310                 315                 320

Tyr Thr Gln Gly Ala Val Ala Glu Arg Trp Lys Glu Thr Leu Gly Arg
                325                 330                 335

Ser Asp Arg Gly Val Ile Met Tyr Arg Asn Leu Leu Lys Ala Asn Leu
            340                 345                 350

Glu Lys Leu Ala Arg Gly Glu Glu Pro Met Asn Val Phe Arg Asp Pro

-continued

```
            355                 360                 365
Ala Lys Ala Ala Phe Ile Gln Leu Asp Thr Glu Glu Ser Ser Gly Arg
    370                 375                 380

Arg Leu Tyr Ser Asp Arg Ala Arg Gln Tyr Gly Pro Ser Ser Ser Asn
385                 390                 395                 400

Gly Pro Gly Gly Gly Ala Thr Lys Tyr Ser Pro Val Leu Asn Leu His
                405                 410                 415

Lys Gly Ala Glu Thr Val Ser Ala Lys Glu Val Met Pro Glu Thr Ala
                420                 425                 430

Leu Pro Ala Ala Pro Pro Ala Ala Arg Lys Glu Thr Ala
            435                 440                 445
```